(12) United States Patent
DeShazo et al.

(10) Patent No.: US 12,417,690 B2
(45) Date of Patent: Sep. 16, 2025

(54) IMPLANTABLE MEDICAL DEVICE (IMD) WITH CODE PATH METRICS

(71) Applicant: Advanced Neuromodulation Systems, Inc., Plano, TX (US)

(72) Inventors: Daran DeShazo, Lewisville, TX (US); Edward Lundberg, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 96 days.

(21) Appl. No.: 18/540,792

(22) Filed: Dec. 14, 2023

(65) Prior Publication Data

US 2024/0221483 A1 Jul. 4, 2024

Related U.S. Application Data

(60) Provisional application No. 63/436,178, filed on Dec. 30, 2022, provisional application No. 63/436,185, (Continued)

(51) Int. Cl.
| | |
|---|---|
| G08B 21/00 | (2006.01) |
| A61B 5/07 | (2006.01) |
| A61N 1/02 | (2006.01) |
| A61N 1/08 | (2006.01) |
| A61N 1/372 | (2006.01) |

(Continued)

(52) U.S. Cl.
CPC ............ *G08B 21/182* (2013.01); *A61B 5/076* (2013.01); *A61N 1/025* (2013.01); *A61N 1/08* (2013.01); *A61N 1/37217* (2013.01); *A61N 1/378* (2013.01); *G06F 11/302* (2013.01); *G06F 11/3466* (2013.01); *G16H 40/40* (2018.01); *G16H 40/67* (2018.01); *G16H 50/20* (2018.01)

(58) Field of Classification Search
USPC ........... 340/540, 539.3, 539.12, 539.22, 588, 340/686.6, 691.3, 3.3, 3.31, 3.32, 3.44, 340/825.27, 5.22, 5.6, 7.52, 10.52
See application file for complete search history.

(56) References Cited

U.S. PATENT DOCUMENTS

| | | | |
|---|---|---|---|
| 11,494,295 B1 | 11/2022 | Sirianni et al. | |
| 2004/0167587 A1* | 8/2004 | Thompson | G16H 20/30 607/60 |

(Continued)

OTHER PUBLICATIONS

Patent Cooperation Treaty, International Search Report and Written Opinion issued for PCT Application No. PCT/US2023/084100, dated May 7, 2024, 9 pages.

(Continued)

*Primary Examiner* — Daniel Previl
(74) *Attorney, Agent, or Firm* — Norton Rose Fulbright US LLP

(57) ABSTRACT

A system and method of quantifying, maintaining and managing the functional status and/or therapy settings of an IMD based on code path metrics is disclosed. The codebase of device firmware modules may be instrumented to obtain tracing data and timing metrics data corresponding to different code paths that may be taken when a device subsystem or associated functionality is accessed or activated. Code path metrics of actual code paths may be analyzed to detect a deviation from baseline code path metrics and generate a corresponding graduated response.

27 Claims, 20 Drawing Sheets

Related U.S. Application Data filed on Dec. 30, 2022, provisional application No. 63/436,173, filed on Dec. 30, 2022, provisional application No. 63/436,192, filed on Dec. 30, 2022.

(51) Int. Cl.
| | |
|---|---|
| *A61N 1/378* | (2006.01) |
| *G06F 11/30* | (2006.01) |
| *G06F 11/34* | (2006.01) |
| *G08B 21/18* | (2006.01) |
| *G16H 40/40* | (2018.01) |
| *G16H 40/67* | (2018.01) |
| *G16H 50/20* | (2018.01) |

(56) References Cited

U.S. PATENT DOCUMENTS

| | | | | |
|---|---|---|---|---|
| 2005/0061336 | A1* | 3/2005 | Goetz | A61B 90/00 128/903 |
| 2005/0085863 | A1* | 4/2005 | Brodnick | A61B 5/308 607/27 |
| 2006/0224204 | A1* | 10/2006 | Hettrick | A61N 1/36564 607/23 |
| 2009/0182517 | A1 | 7/2009 | Gandhi et al. | |
| 2009/0259269 | A1* | 10/2009 | Brown | A61B 5/363 607/14 |
| 2009/0270933 | A1* | 10/2009 | Hettrick | A61B 5/0538 607/6 |
| 2013/0006333 | A1* | 1/2013 | Kaula | A61N 1/04 365/189.011 |
| 2015/0190646 | A1 | 7/2015 | Matos | |
| 2017/0220404 | A1 | 8/2017 | Polar Seminario | |
| 2019/0266070 | A1 | 8/2019 | Bhandarkar et al. | |
| 2019/0384699 | A1 | 12/2019 | Arbon et al. | |
| 2020/0089893 | A1 | 3/2020 | Davidi et al. | |
| 2020/0357513 | A1 | 11/2020 | Katra et al. | |
| 2021/0098124 | A1 | 4/2021 | Crook et al. | |
| 2021/0260366 | A1 | 8/2021 | Cheeran et al. | |
| 2022/0164218 | A1 | 5/2022 | Sankaran et al. | |
| 2022/0323766 | A1 | 10/2022 | Hughes et al. | |

OTHER PUBLICATIONS

Patent Cooperation Treaty, International Search Report and Written Opinion issued for PCT Application No. PCT/US2023/084104, dated May 7, 2024, 12 pages.

Patent Cooperation Treaty, International Search Report and Written Opinion issued for PCT Application No. PCT/US2023/084106, dated May 8, 2024, 10 pages.

Patent Cooperation Treaty, International Search Report and Written Opinion issued for PCT Application No. PCT/US2023/084112, dated May 8, 2024, 8 pages.

* cited by examiner

IMPLANTABLE MEDICAL DEVICE (IMD) WITH CODE PATH METRICS

PRIORITY AND CROSS-REFERENCE TO RELATED APPLICATION(S)

This nonprovisional application claims priority based upon the following prior United States provisional patent application(s): (i) "IMPLANTABLE MEDICAL DEVICE (IMD) WITH CODE PATH METRICS," Application No.: 63/436,173, filed Dec. 30, 2022; (ii) "IMPLANTABLE MEDICAL DEVICE (IMD) WITH CODE PATH METRICS FOR CHARACTERIZING SUBSYSTEM POWER CONSUMPTION," Application No.: 63/436,178, filed Dec. 30, 2022; (iii) "IMPLANTABLE MEDICAL DEVICE (IMD) WITH CODE PATH METRICS FOR CHARACTERIZING DEVIATION FROM BASELINE PATHS," Application No.: 63/436,185, filed Dec. 30, 2022; and (iv) "IMPLANTABLE MEDICAL DEVICE (IMD) WITH CODE PATH METRICS FOR CATEGORIZATION OF CODE PATHS," Application No.: 63/436,192, filed Dec. 30, 2022; each of which is hereby incorporated by reference in its entirety.

TECHNICAL FIELD

The present application is generally directed to implantable medical devices configured to operate and/or provide therapy or medical diagnostic operations using code path metrics.

BACKGROUND

Implantable medical devices have changed how medical care is provided to patients having a variety of chronic illnesses and disorders. For example, implantable cardiac devices improve cardiac function in patients with heart disease by improving quality of life and reducing mortality rates. Respective types of implantable neurostimulators provide a reduction in pain for chronic pain patients and reduce motor difficulties in patients with Parkinson's disease and other movement disorders. A variety of other medical devices are proposed and are in development to treat other disorders in a wide range of patients.

Implantable medical devices have become more complex than earlier generation devices and provide a variety of potentially complex features for therapeutic and/or diagnostic operations. As the power and functionality of the implantable and other personal medical devices deployed in various types of therapy settings increases, the firmware code complexity to support therapeutic and/or diagnostic features of the devices also increases.

SUMMARY

Representative embodiments are directed to a system and method for quantifying, maintaining and/or otherwise managing the functional status and/or therapy mode of an IMD based on code flow data (e.g., tracing and timing metrics) obtained via suitable code tracing operations. In some aspects, the codebase of device firmware modules may be designated with unique identifiers to obtain tracing data and timing metrics data corresponding to different code paths that may be taken when a device subsystem is accessed or activated during operations after the device is implanted in a patient. In some embodiments, code path metrics of actual code paths may be compared against baseline code path metrics to detect a deviation and generate a corresponding error state notification. In response, a graduated response protocol may be performed to control further operations of the respective device subsystem.

In an aspect, a method for conducting diagnostic analysis of firmware code of an IMD of a patient is disclosed. The method includes storing, by one or more processors of the IMD, firmware for execution by the one or more processors at a memory, where the firmware includes a plurality of firmware modules controlling one or more corresponding hardware components of the IMD configured to support respective IMD functions. Each of the plurality of firmware modules is associated with multiple code paths traversing respective firmware code instructions. The method also includes receiving, by the one or more processors, an artificial intelligence (AI) model from a remote device via wireless communication circuitry. The AI model is trained based on a training dataset including code paths, code path metrics, or both associated with IMDs corresponding to a population of patients. The method further includes generating, by the one or more processors, code path information associated with one or more code paths executed during operation of the IMD. The code path information is generated based on the firmware code instructions and indicates execution of code corresponding to one or more code paths of the plurality of code paths. The method includes storing, by the one or more processors, the code path information in the memory. The method also includes quantifying, by the one or more processors, performance of the IMD based on the code path information using the AI model.

In an aspect, an IMD for implantation in a patient is disclosed. The IMD includes: one or more processors for controlling IMD operations; a battery for powering IMD operations; circuitry for controlling provision of a medical therapy to the patient or for conducting medical diagnostic operations; wireless communication circuitry for conducting communication with one or more devices external to the patient after implantation; and persistent memory for storing firmware for execution by the one or more processors. The firmware includes a plurality of firmware modules controlling one or more corresponding hardware components of the IMD for respective IMD functions. In an aspect, multiple identified code paths traversing respective firmware code instructions are identified for each of the plurality of firmware modules. The one or more processors, when executing firmware code for the plurality of firmware modules, may be configured to: store identifiers corresponding to respective code paths of the multiple identified code paths in one or more memory buffers to indicate execution of code of each respective code path; process stored code path identifiers stored in the one or more buffers to generate respective code path metrics; calculate at least one power consumption metric using one or more respective calculated code path metrics; and reset at least one of the plurality of firmware modules upon determining that the power consumption metric indicates improper IMD operations.

In an aspect, a method for quantifying, managing, and maintaining performance of an IMD providing a medical therapy to a patient is disclosed. The method includes receiving, by at least one processor, code path information from the IMD. The code path information may include one or more identifiers corresponding to a code path executed by at least one firmware module of a plurality of firmware modules of the IMD to control one or more corresponding hardware components for respective IMD functions. Multiple identified code paths traversing respective firmware code instructions may be identified for each of the plurality of firmware modules. The method includes processing, by the at least one processor, the code path information to generate respective code path metrics. The method includes calculating, by the at least one processor, at least one power consumption metric using one or more respective calculated code path metrics and generating, by the at least one processor, instructions to reset at least one of the plurality of firmware modules upon determining that the power consumption metric indicates improper IMD operations. The method may include transmitting, by the at least one processor, the instructions to the IMD via a wireless communication link.

In an aspect, an implantable pulse generator (IPG) for providing electrical pulses to neural tissue of a patient is disclosed. The IPG includes: at least one processor for controlling IPG operations; a battery for powering IPG operations; circuitry for generating electrical pulses to stimulate the neural tissue of the patient; wireless communication circuitry for conducting communication with one or more devices external to the patient after implantation; and persistent memory for storing firmware for execution by the at least one processor. The firmware may include a plurality of firmware modules for controlling corresponding subsystems of the IPG, where each subsystem may be controlled by multiple identified code paths traversing firmware code for implementing each respective subsystem. The at least one processor, when executing firmware code for the IPG subsystems, may be configured to receive code path information from the IMD. The code path information may include one or more identifiers corresponding to a code path executed by at least one firmware module of the plurality of firmware modules of the IMD to control one or more corresponding hardware components for respective IMD functions. The at least one processor may be configured to process the code path information to generate respective code path metrics; calculate at least one power consumption metric using one or more respective calculated code path metrics; and generate instructions to reset at least one of the plurality of firmware modules upon determining that the power consumption metric indicates improper IMD operations.

In an aspect, an IMD for implantation in a patient is disclosed. The IMD includes: one or more processors for controlling IMD operations; a battery for powering IMD operations; circuitry for controlling provision of a medical therapy to the patient or for conducting medical diagnostic operations; wireless communication circuitry for conducting communication with one or more devices external to the patient after implantation; and persistent memory for storing firmware for execution by the one or more processors. The firmware includes a plurality of firmware modules controlling one or more corresponding hardware components of the IMD for respective IMD functions. In an aspect, multiple identified code paths traversing respective firmware code instructions may be identified for each of the plurality of firmware modules. The one or more processors, when executing firmware code for the plurality of firmware modules, may be configured to: store identifiers corresponding to respective code paths of the multiple identified code paths in one or more memory buffers to indicate execution of code of each respective code path; process stored code path identifiers stored in the one or more buffers to generate respective code path metrics; calculate at least one power consumption metric using one or more respective calculated code path metrics; and generate a power overconsumption flag upon determining that the power consumption metric indicates improper IMD operations.

In an aspect, a method for controlling an IMD for implantation in a patient is disclosed. The method includes storing, in a persistent memory of the IMD, firmware for execution by one or more processors of the IMD. The firmware may include a plurality of firmware modules controlling one or more corresponding hardware components of the IMD for respective IMD functions. In an aspect, multiple identified code paths traversing respective firmware code instructions may be identified for each of the plurality of firmware modules. The method includes storing, by the one or more processors, when executing firmware code for the plurality of firmware modules, code path identifiers in one or more memory buffers. The code path identifiers may correspond to respective code paths of the multiple identified code paths stored in the one or more memory buffers to indicate execution of code of each respective code path. The method includes processing, by the one or more processors, stored code path identifiers stored in the one or more buffers to generate respective code path metrics. The method includes calculating, by the one or more processors, at least one power consumption metric using one or more respective calculated code path metrics, and generating, by the one or more processors, a power overconsumption flag upon determining that the power consumption metric indicates improper IMD operations.

In an aspect, an IPG for providing electrical pulses to neural tissue of a patient is disclosed. The IPG includes: at least one processor for controlling IPG operations; a battery for powering the IPG operations; circuitry for generating electrical pulses to stimulate the neural tissue of the patient; wireless communication circuitry for conducting communication with one or more devices external to the patient after implantation; and persistent memory for storing firmware for execution by the at least one processor. The firmware includes a plurality of firmware modules for controlling corresponding subsystems of the IPG. Each subsystem may be controlled by multiple identified code paths traversing firmware code for implementing each respective subsystem. The at least one processor, when executing firmware code for the IPG subsystems, may be configured to: store code path identifiers corresponding to respective code paths of the multiple identified code paths in one or more memory buffers to indicate execution of code of each respective code path; process stored code path identifiers stored in the one or more buffers to generate respective code path metrics; calculate at least one power consumption metric using one or more respective calculated code path metrics; and generate a power overconsumption flag upon determining that the power consumption metric indicates improper IMD operations.

In an aspect, an IMD for implantation in a patient is disclosed. The IMD may include: one or more processors for controlling IMD operations; a battery for powering the IMD operations; circuitry for controlling provision of a medical therapy to the patient or for conducting medical diagnostic operations; wireless communication circuitry for conducting communication with one or more devices external to the patient after implantation; and persistent memory for storing firmware for execution by the one or more processors. The firmware includes a plurality of firmware modules controlling one or more corresponding hardware components of the IMD for respective IMD functions. In an aspect, multiple identified code paths traversing respective firmware code instructions may be identified for each of the plurality of firmware modules. The one or more processors, when executing firmware code for the IMD subsystems, may be configured to: store an identifier corresponding to a respective code path of the multiple identified code paths in one or more memory buffers to indicate execution of code of the respective code path; calculate a deviation metric representing a difference between an observed firmware execution for a respective firmware module and baseline code execution defined for the respective firmware module; and responsive to determining that the deviation metric is greater than or equal to a threshold value, generate an error state notification with respect to the respective firmware module.

In an aspect, a system for managing an IMD is disclosed. The system includes: a memory; and one or more processors communicatively coupled to the memory. The one or more processors may be configured to receive an identifier corresponding to a respective code path of multiple identified code paths. Each of the identified code paths corresponding to execution of one or more firmware modules a plurality of firmware modules of the IMD configured to control respective IMD functions for providing a therapy to a patient. The one or more processors may be configured to calculate a deviation metric representing a difference between an observed firmware execution for a respective firmware module and baseline code execution defined for a firmware module of the one or more firmware modules corresponding to the respective code path. Responsive to determining that the deviation metric is greater than or equal to a threshold value, the one or more processors may be configured to generate an error state notification with respect to the respective firmware module.

In an aspect, a method for monitoring an implantable pulse generator (IPG) for delivering a medical therapy to a patient is described. The method includes storing, by one or more processors, firmware for execution by the one or more processors. The firmware includes a plurality of firmware modules controlling one or more corresponding hardware components of the IPG for respective IPG functions. In an aspect, multiple identified code paths traversing respective firmware code instructions may be identified for each of the plurality of firmware modules. The method includes storing, by the one or more processors when executing firmware code for the IPG subsystems, an identifier corresponding to a respective code path of multiple identified code paths in one or more memory buffers to indicate execution of code of the respective code path. The method includes calculating, by the one or more processors, a deviation metric representing a difference between an observed firmware execution for a respective firmware module and baseline code execution defined for the respective firmware module. The method includes generating, by the one or more processors, an error state notification with respect to the respective firmware module responsive to determining that the deviation metric is greater than or equal to a threshold value.

In an aspect, a method for conducting diagnostic analysis of firmware code of an IMD of a patient is described. The method includes storing, by one or more processors of the IMD, firmware for execution by the one or more processors at a memory. The firmware may include a plurality of firmware modules for controlling one or more corresponding hardware components of the IMD configured to support respective IMD functions. Each of the plurality of firmware modules may be associated with multiple code paths traversing respective firmware code instructions. The method includes receiving, by the one or more processors, an artificial intelligence (AI) model from a remote device via wireless communication circuitry. The AI model may be trained based on a training dataset comprising code paths, code path metrics, or both associated with IMDs corresponding to a population of patients. The method includes generating, by the one or more processors, code path information associated with one or more code paths executed during operation of the IMD. The code path information may be generated based on the firmware code instructions and indicates execution of code corresponding to one or more code paths of the plurality of code paths. The method includes storing, by the one or more processors, the code path information in the memory. The method includes quantifying, by the one or more processors, performance of the IMD based on the code path information using the AI model.

In an aspect, a method for conducting diagnostic analysis of firmware code of an implantable medical device (IMD) of a patient is described. The method includes training, by one or more processors, an AI model configured to quantify performance of an IMD to produce a trained AI model. The training of the AI model may be based on a training dataset that includes information associated with code paths, code path metrics, or both associated with IMDs corresponding to a population of patients. The method includes transmitting, by the one or more processors, the trained AI model to at least one IMD. The at least one IMD includes firmware for execution by one or more processors of the IMD. The firmware of the IMD may include a plurality of firmware modules controlling one or more corresponding hardware components of the IMD configured to support respective IMD functions. Each of the plurality of firmware modules is associated with multiple code paths traversing respective firmware code instructions. The method includes receiving, by the one or more processors, feedback from the at least one IMD. The feedback may include code path metrics generated based on execution of one or more code paths traversed during operations of the at least on IMD, information identifying one or more stimulation programs of the at least one IMD, information identifying one or more stimulation parameters of the one or more stimulation programs, information identifying one or more component states for the at least one IMD, or a combination thereof. The method includes updating, by the one or more processors, the trained AI model based on the feedback to produce an updated trained AI model, and transmitting, by the one or more processors, the updated trained AI model to the at least one IMD.

In an aspect, a method of controlling operations of IMDs using an AI model of IMD operation based on firmware code path execution in respective IMDs is described. The method includes receiving, by one or more servers for IMD management, code path data from a plurality of IMDs after implantation in respective patients. The code path data may represent firmware code instructions executed by one or more firmware modules of a plurality of firmware modules corresponding to firmware executable by one or more processors of each of the plurality of IMDs to control corresponding hardware components of the IMDs for respective IMD functions. In an aspect, multiple identified code paths traversing respective firmware code instructions may be identified for each of the plurality of firmware modules. The method includes training, using one or more servers, the AI model using the received code path data to generate a model of IMD operations representing proper operation of an IMD. The method includes distributing the trained AI model from one or more servers for IMD management to a set of IMDs. The method includes operating IMDs of the set of IMDs to perform IMD-diagnostic operations based on the distributed, trained AI model to control IMD operations.

DETAILED DESCRIPTION

Figure 1:
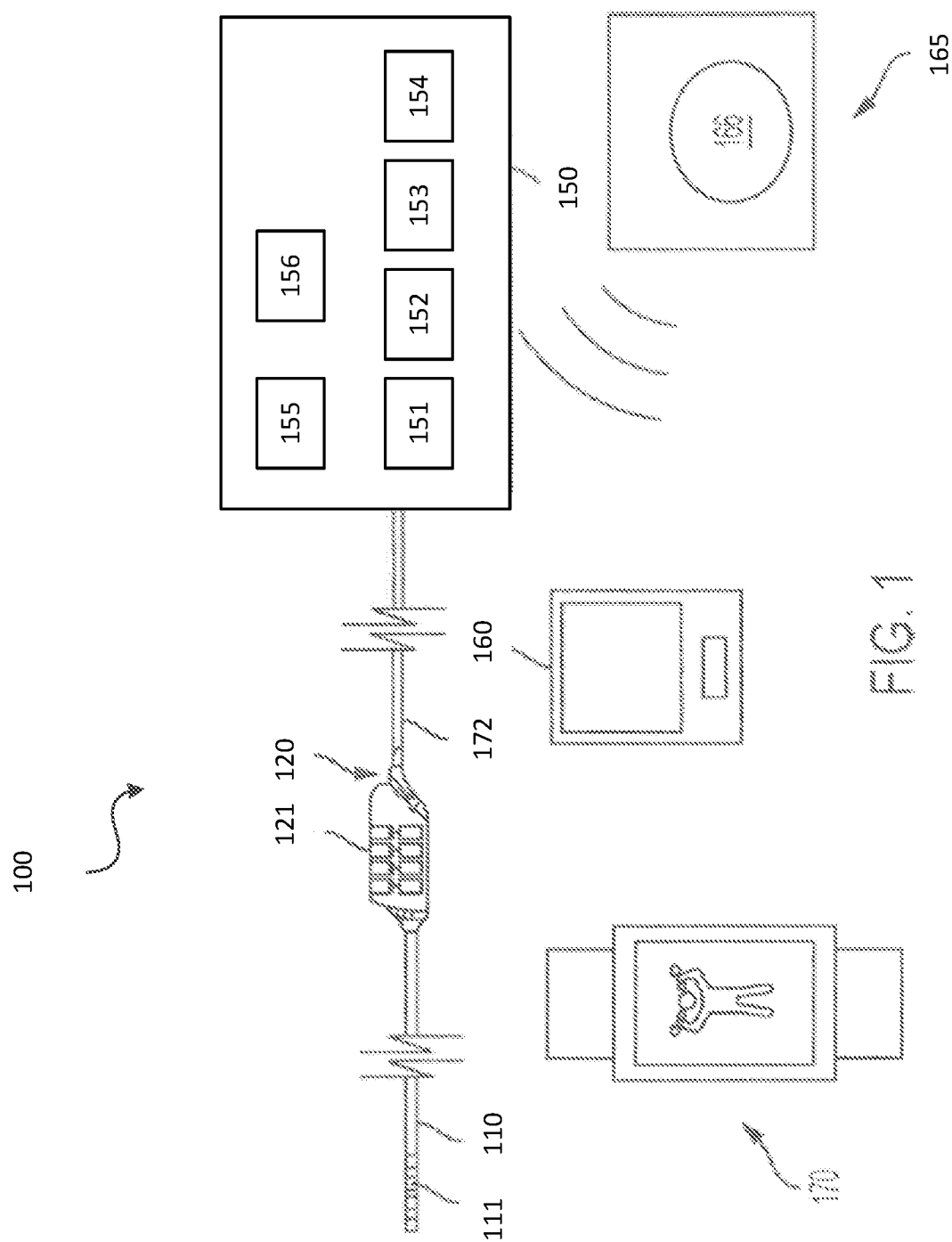
FIG. 1 depicts an example implantable medical device (IMD) including a plurality of subsystems and associated functions that may be effectuated using one or more firmware modules having code path instrumentation and metrics according to some representative embodiments of the present disclosure.

In the description herein for embodiments of the present disclosure, numerous specific details are provided, such as examples of devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like set forth in reference to other embodiments herein. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Example embodiments described herein relate to quantifying, maintaining, and managing the operational and functional status of an IMD based on suitable code path flow metrics. Some example embodiments may be configured to utilize code path metrics for effectuating graduated responses and appropriate error status notifications in managing an IMD subsystem's operation. Regardless of the deployment scenarios, example embodiments of the present disclosure may be configured to support a code instrumentation scheme for obtaining code path metrics (also referred to as code flow metrics, execution coverage data, code execution metrics, or terms of similar import) with respect to one or more firmware modules of an IMD device based on various techniques such as, without limitation, code execution tracing, timing, breakpoint insertion, etc. Further, some example embodiments herein may be configured to utilize respective code flow metrics associated with the IMD's subsystems for detecting potential error states of operation relative to the code flow metrics of baseline code paths known or predicted to yield acceptable modes of operation. As used herein, instrumentation refers to the process of adding code to firmware instructions so that its inner state during operation may be monitor, measured, and/or analyzed. Instrumented firmware code may measure what respective code is doing by collecting data such as metrics, events, logs, and traces (MELT). Any suitable technique of instrumentation may be employed including source instrumentation and binary instrumentation as examples.

In some embodiments, code flow metrics are employed in a neurostimulation system. Neurostimulation systems are devices that generate electrical pulses and deliver the pulses to neural tissue of a patient to treat a variety of disorders. One category of neurostimulation systems is deep brain stimulation (DBS). In DBS, pulses of electrical current are delivered to target regions of a subject's brain, for example, for the treatment of movement and effective disorders, such as Parkinson's Disease (PD) and essential tremor. Another category of neurostimulation systems is spinal cord stimulation (SCS) systems, which may be used to treat chronic pain of a patient, such as to treat Failed Back Surgery Syndrome (FBSS), Complex Regional Pain Syndrome (CRPS), or other conditions resulting in chronic patient pain. SCS devices may also treat a number of other disorders in addition to chronic pain. Dorsal root ganglion (DRG) stimulation is another example of a neurostimulation therapy in which electrical stimulation is provided to the DRG structure that is just outside of the epidural space. DRG stimulation is also generally used to treat chronic pain but may treat other disorders. Neurostimulation therapies including SCS stimulation and DRG stimulation are also known to effect other physiological processes such as cardiac, respiratory, and digestive processes as examples.

Neurostimulation systems generally include an implantable medical device (IMD) having an implantable pulse generator (IPG) and one or more stimulation leads. A stimulation lead may include a lead body of insulative material that encloses one or more wire conductors. The distal end of the stimulation lead may include multiple electrodes, or contacts, that intimately impinge upon patient tissue and are electrically coupled to the wire conductors. The proximal end of the lead body includes multiple terminals (also electrically coupled to the wire conductors) that are adapted to receive electrical pulses. In DBS systems, the distal end of the stimulation lead is implanted within the brain tissue to deliver the electrical pulses. The stimulation leads are then tunneled to another location within the patient's body to be electrically connected with a pulse generator or, alternatively, to an "extension" electrically connected with the pulse generator. The pulse generator is typically implanted in the patient within a subcutaneous pocket created during the implantation procedure.

The pulse generator is typically implemented using a metallic housing (or "can") that encloses circuitry for generating the electrical stimulation pulses, control circuitry, communication circuitry, a rechargeable or primary cell battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on the proximal end of a stimulation lead. Additional components may be located in the header such as one or more antennas for wireless communication and/or an inductive coil to receive power to recharge the IPG battery, as examples.

Referring to FIG. 1, a stimulation system according to some embodiments is shown as a stimulation system 100. Stimulation system 100 provides a therapy to the patient and/or conducts medical diagnostic operations (e.g., cardiac sensing, neural sensing, respiratory sensing, glucose sensing, and/or the like). In some embodiments, system 100 generates electrical pulses for application to tissue of a patient to treat one or more symptoms of the patient, such as symptoms associated with movement disorders, chronic pain, and the like. System 100 includes an implantable medical device (IMD) 150 including an implantable pulse generator (IPG). Examples of commercially available IPGs include the ETERNA™, PROCLAIM XR™ and INFINITY™ implantable pulse generators (available from ABBOTT, PLANO TX) which could be modified as described herein. It is noted that IMD 150 typically includes a metallic housing (or can) that encloses a controller 151, therapeutic (e.g., pulse generating) circuitry 152, a battery 153, far-field and/or near field communication circuitry 154 (e.g., BLUETOOTH communication circuitry), and other appropriate circuitry and components of the device. Controller 151 typically includes one or more microcontrollers or other suitable processors for controlling the various other components of the IMD 150. It should be noted that all operations described herein need not be performed on the same processor or same processor core (distributed execution of applicable instructions may be employed as deemed appropriate for any specific implementation). Firmware (software) code is typically stored in memory 156 of IMD 150 for execution by the microcontroller or processor to control the various components of the device.

IMD 150 may comprise one or more attached extension components 120 or be connected to one or more separate extension components 120 which, in turn, may be connected to one or more stimulation leads 110. Alternatively, one or more stimulation leads 110 may be connected directly to IMD 150. Within IMD 150, electrical pulses are generated by pulse generating circuitry 152 and are provided to switching circuitry. The switching circuit connects to output wires, metal ribbons, traces, lines, or the like (not shown) from the internal circuitry of IMD 150 to output connectors (not shown) of IMD 150 which are typically contained in the "header" structure of IMD 150. Commercially available ring/spring electrical connectors are frequently employed for output connectors of pulse generators (e.g., "Bal-Seal" connectors). The terminals of one or more stimulation leads 110 are inserted within connector portion 121 for electrical connection with respective connectors or directly within the header structure of pulse generator 150. Thereby, the pulses originating from IMD 150 are conducted to electrodes 111 through wires contained within the lead body of lead 110. The electrical pulses are applied to tissue of a patient via electrodes 111.

For implementation of the components within IMD 150 as an implantable pulse generator, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IMD 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Stimulation lead 110 may include any suitable number and type of electrodes 111, terminals, and internal conductors. Additionally or alternatively, various sensors (not shown) may be located near the distal end of stimulation lead 110 and electrically coupled to terminals through conductors within the lead body 172. In an aspect, the plurality of electrodes 111 may also include electrodes used for both stimulation and sensing, sensing only, or stimulation only. Such sensors may also be deployed separately from leads 110 if deemed appropriate for a specific medical purpose. Sensing or medical diagnostic circuitry 155 may be included within IMD 150 to sense, sample, and/or process signals indicative of patient physical activity, physiological activity, a patient condition and/or the like, as non-limiting examples. For example, IMD 150 may employ circuitry 155 to assist measurement, identification, and/or analysis of neurological activity, cardiac activity, respiratory activity, glucose levels, drug or pharmaceutical concentration levels, patient physical activity, and/or the like.

External controller device 160 is a device that permits the operations of IMD 150 to be controlled after IMD 150 is implanted within a patient and/or permits communication with IMD 150. Also, multiple controller devices may be provided for different types of users (e.g., a patient controller device may be provided to the patient and/or a clinician controller device, also referred to as a clinician programmer, may be provided to a clinician). Controller device 160 can be implemented by utilizing a suitable handheld processor-based system that possesses wireless communication capabilities. Software is typically stored in memory of controller device 160 and may be executed by one or more processors of the controller device 160 to control the various operations of controller device 160. The interface functionality of controller device 160 is implemented using suitable software code for interacting with the user and using the wireless communication capabilities to conduct communications with IMD 150. One or more user interface screens may be provided by software stored in the memory of the controller device 160 to allow the patient and/or the patient's clinician to control operations of IMD 150 using controller device 160. In some embodiments, commercially available devices such as APPLE IOS devices are adapted for use as controller device 160 and may include one or more "apps" that communicate with IMD 150 using, for example, BLUETOOTH communication.

In some embodiments, controller device 160 may preferably conduct communications with IMD 150 to retrieve patient and/or device data. For example, controller device 160 may obtain cardiac activity data, respiratory data, glucose level data, and/or the like from IMD 150, such as may be obtained by one or more of the sensors described above. Additionally, controller device 160 may obtain battery level data or other device data from IMD 150. In some embodiments, controller device 160 receives code path data from IMD 150.

In some embodiments, controller device 160 may provide one or more user interfaces to allow the user to operate IMD 150 according to one or more therapy programs to treat the patient's disorder(s). For neurostimulation therapies, each therapy program may include one or more sets of stimulation parameters, which may include parameters to configure pulse amplitude, pulse width, pulse frequency or inter-pulse period, pulse repetition (e.g., number of times for a given pulse to be repeated for respective stimset during execution of program), other parameters, or a combination thereof.

Controller device 160 may permit programming of IMD 150 to provide a number of different stimulation patterns or therapies to the patient as appropriate for a given patient and/or disorder. Examples of different stimulation therapies include conventional tonic stimulation (e.g., continuous train of stimulation pulses at a fixed rate), burst stimulation (e.g., bursts of multiple high frequency pulses, bursts of pulses repeated at a high rate interspersed with quiescent periods with or without duty cycling, and the like), "high frequency" stimulation (e.g., a continuous train of stimulation pulses at 10,000 Hz), multi-frequency stimulation, noise stimulation (e.g., a series of stimulation pulses with randomized pulse characteristics such as pulse amplitude to achieve a desired frequency domain profile), other types of stimulation therapies, or a combination thereof. Any suitable stimulation pattern or combination thereof can be provided by IMD 150 according to some embodiments. Controller device 160 communicates the stimulation parameters and/or a series of pulse characteristics defining the pulse series to be applied to the patient to IMD 150 to generate the desired stimulation therapy.

Descriptions of respective neurostimulation therapies are provided in the following publications: (1) Schu S., Slotty P. J., Bara G., von Knop M., Edgar D., Vesper J. A Prospective, Randomised, Double-blind, Placebo-controlled Study to Examine the Effectiveness of Burst Spinal Cord Stimulation Patterns for the Treatment of Failed Back Surgery Syndrome. Neuromodulation 2014; 17: 443-450; (2) Al-Kaisy A1, Van Buyten J P, Smet I, Palmisani S, Pang D, Smith T. 2014. Sustained effectiveness of 10 kHz high-frequency spinal cord stimulation for patients with chronic, low back pain: 24-month results of a prospective multicenter study. Pain Med. 2014 March; 15(3):347-54; and (3) Sweet, Badjatiya, Tan D1, Miller. Paresthesia-Free High-Density Spinal Cord Stimulation for Postlaminectomy Syndrome in a Prescreened Population: A Prospective Case Series. Neuromodulation. 2016 April; 19(3):260-7. Noise stimulation is described in U.S. Pat. No. 8,682,441B2. Burst stimulation is described in U.S. Pat. No. 8,224,453 and U.S. Published Application No. 20060095088. A "coordinated reset" pulse pattern is applied to neuronal subpopulation/target sites to desynchronize neural activity in the subpopulations. Coordinated reset stimulation is described, for example, by Peter A. Tass et al in COORDINATED RESET HAS SUSTAINED AFTER EFFECTS IN PARKINSONIAN MONKEYS, Annals of Neurology, Volume 72, Issue 5, pages 816-820, November 2012, which is incorporated herein by reference. The electrical pulses in a coordinated reset pattern are generated in bursts of pulses with respective bursts being applied to tissue of the patient using different electrodes in a time-offset manner. The time-offset is selected such that the phase of the neural-subpopulations are reset in a substantially equidistant phase-offset manner. By resetting neuronal subpopulations in this manner, the population will transition to a desynchronized state by the interconnectivity between the neurons in the overall neuronal population. All of these references are incorporated herein by reference.

For implementation of the components within IMD 150, a processor and associated charge control circuitry for an exemplary implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION" which is incorporated herein by reference.

When implemented as an implantable pulse generator, IMD 150 modifies its internal parameters in response to the control signals (e.g., programming information specifying stimulation parameters for one or more therapy programs) from controller device 160 to vary the stimulation characteristics of stimulation pulses transmitted through stimulation lead 110 to the tissue of the patient. Exemplary neurostimulation systems, stimsets, and multi-stimset programs are described in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," the contents of which are incorporated herein by reference.

External charger device 165 may be provided to recharge battery 153 of IMD 150 according to some embodiments, such as when IMD 150 includes a rechargeable battery. External charger device 165 may include a power source and electrical circuitry (not shown) to drive current through primary coil 166. The patient places the primary coil 166 against or proximate to the patient's body immediately above or within the vicinity of a secondary coil (not shown), where the secondary coil may be incorporated into IMD 150. Preferably, the primary coil 166 and the secondary coil are aligned in a coaxial manner by the patient for efficiency of the coupling between the primary and secondary coils. In operation during a charging session, external charger device 165 generates an AC-signal to drive current through coil 166 at a suitable frequency. Assuming that primary coil 166 and secondary coil are suitably positioned relative to each other, the secondary coil is disposed within the magnetic field generated by the current driven through primary coil 166. Current is then induced by a magnetic field in the secondary coil. The current induced in the secondary coil of IMD 150 is rectified and regulated to recharge battery 153 of IMD 150. IMD 150 may also communicate status messages to external charging device 165 during charging operations to control charging operations. For example, IMD 150 may communicate the coupling status, charging status, charge completion status, etc.

System 100 may include external wearable device 170 such as a smartwatch or health monitoring device. Wearable device 170 may be implemented using commercially available devices such as FITBIT VERSA SMARTWATCH™, SAMSUNG GALAXY SMARTWATCH™, and APPLE WATCH™ devices with one or more apps or appropriate software to interact with IMD 150 and/or controller device 160. In some embodiments, wearable device 170, controller device 160, and IMD 150 conduct communications using BLUETOOTH communications. However, it is noted that other communication techniques may be utilized.

Wearable device 170 may be utilized to monitor activities of the patient and/or sense physiological signals of the patient. Wearable device 170 may track physical activity and/or patient movement through various types of sensors, such as accelerometers, gyroscopes, and the like. It is noted that wearable device 170 may also be configured with other types of sensors, such as to monitor body temperature, heart rate, electrocardiogram activity, blood oxygen saturation, and/or the like. Wearable device 170 may also be utilized to monitor sleep quality or any other relevant health related activity.

Wearable device 170 may provide one or more user interface screens to permit the patient to control or otherwise interact with IMD 150. For example, the patient may utilized the user interface screen(s) provided by wearable device 170 to adjust or modify one or more stimulation parameters, such as to increase or decrease stimulation amplitude, change stimulation programs, turn stimulation on or off, and/or the like. Also, the patient may use the user interface(s) and applications configured for wearable device 170 to check a status of a battery (e.g., current charge level, a duration of time a current stimulation program may be run based on the current battery level, etc.) or other status information related to IMD 150.

The one or more user interface screens of wearable device 170 may include one or more interface screens to receive patient input. In some embodiments, wearable device 170 and/or controller device 160 are implemented (individually or in combination) to provide an electronic patient diary function. The patient diary function permits the patient to record on an ongoing basis the health status of the patient and the effectiveness of the therapy for the patient. In some embodiments as discussed herein, wearable device 170 and/or controller device 160 enable the user to indicate the current activity of the patient, the beginning of an activity, the completion of an activity, the ease or quality of patient's experience with a specific activity, the patient's experience of pain, the patient's experience of relief from pain by the stimulation, or any other relevant indication of patient health by the patient.

Whereas some example embodiments may be particularly set forth with respect to an IMDs or neuromodulation systems for providing therapy to a desired area of a body or tissue based on a suitable stimulation therapy application, it should be understood that example embodiments disclosed herein are not limited thereto. Some examples herein may therefore involve different types of implantable devices such as cochlear implants, retinal implants, implantable cardiac rhythm management devices, implantable cardioverter defibrillators, pacemakers, and the like, as well as implantable drug delivery/infusion systems, implantable devices configured to effectuate measurement/monitoring of one or more physiological functions of a patient's body, including various implantable biomedical sensors and sensing systems such as cardiac monitors and glucose monitoring devices. Accordingly, all such devices may be broadly referred to as "implantable medical devices", "personal medical devices," "personal biomedical instrumentation," or terms of similar import, which may be controlled by an external controller device (e.g., operated by a patient, a clinician and/or their respective authorized agents) for controlling, effectuating, or launching a variety of IMD functions and operations by executing associated firmware modules instrumented according to some example embodiments of the present disclosure. Additionally, all of the components shown in FIG. 1 are not required and it should be understood that components may be added or omitted for a specific implantable medical device as appropriate for a given patient indication or application.

Referring to FIG. 1, IMD 150 may store a plurality of firmware modules in memory 156, which may be executed to perform one or more functions of the IPG. The firmware modules are adapted to generate code path data during real-time execution of the firmware instructions after implantation of the device in the patient according to some representative embodiments of the present disclosure. In some embodiments, the firmware code is instrumented appropriately for generating quantitative code flow data. That is, as the firmware instructions are executed on one or more processors of IMD 150, data is generated that reflects the specific execution of an identified code path of a respective firmware module. The code path data is stored (preferably sequentially) in one or more queues or buffers. The code path data is further processed to characterize the real-time operation of the respective firmware modules and one or more corrective actions may be performed or error messages generated in response thereto.

Figure 2:
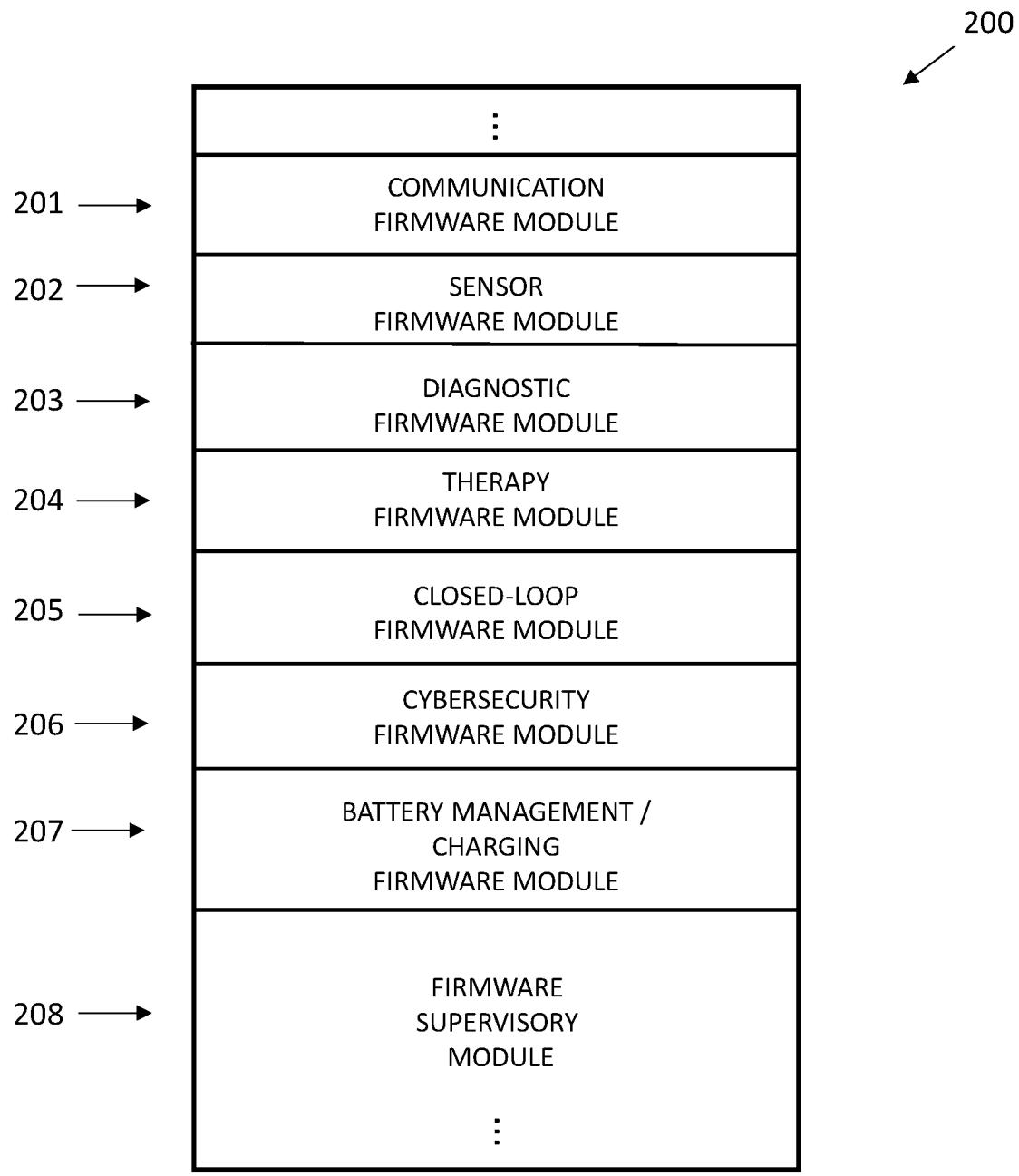
FIG. 2 depicts firmware modules having code path analytics for an IMD according to some representative embodiments.

Referring to FIG. 2, a diagram illustrating firmware having exemplary firmware modules having code path analytics for an IMD according to some representative embodiments is shown as firmware 200. As used herein, "firmware" means computer software programmed on a hardware device (i.e., an IMD) that provides low-level control for a device's specific hardware. Firmware 200 may be stored on the IMD's non-volatile memory (e.g., flash memory). As shown in FIG. 2, firmware 200 includes firmware modules 201-207. Firmware modules 201-207 are provided herein by way of example. An implantable medical device may include any specific number and organization of firmware modules as suitable for a given device and patient application.

As shown in FIG. 2, firmware 200 may include communication firmware module 201 to provide functional processor-executable instructions to conduct wireless communications with one or more external devices (e.g., a patient controller device and/or a clinician programmer device). Firmware module 201 may include instructions to control operations of communication circuitry of a given IMD, such as communication circuitry enabling the IMD to communicate with an external device (e.g., external device 160 of FIG. 1, wearable device 170 of FIG. 1, External charger device 165 of FIG. 1, or other devices).

As shown in FIG. 2, firmware 200 may include sensor module 202 to control sensing hardware of the IMD and diagnostic module 203 to conduct medical diagnostic operations (e.g., processing of sensor data). Diagnostic module 203, for example, may include executable instructions for calibration of sensor data, identification of relevant physiological events or features in the sensor data, and the like. Sensor module 202 may include executable instructions to control when sensor data is captured, a type of sensor data that is captured (e.g., from one or more specific sensors of the IMD), other types of control functions, or a combination thereof.

As shown in FIG. 2, firmware 200 may include therapy module 204. Therapy module 204 may include executable instructions to interact with one or more hardware components of the IMD to provide a medical therapy to the patient. For example, therapy module 204 may control pulse generating circuitry (e.g., of an IPG of the IMD) to generate and output electrical pulses to stimulate neural tissue or cardiac tissue of the patient. As another example, therapy module 204 may control the release or administration of insulin, pharmaceuticals, biologic medications, and/or other suitable compounds or substances. Firmware 200 may include closed-loop module 205 which may be configured to utilize suitable signals to modify the therapy provided to the patient according to therapy module 204. For example, closed-loop module 205 may modify the pulse characteristics (amplitude, pulse width, pulse frequency, electrode configuration, etc.) in response to detection of various physiological features or events.

Firmware 200 may include additional firmware modules to control other operations of the IMD. For example, firmware 200 may include cyber security firmware module 206 which may implement various cybersecurity operations (e.g., authentication, encryption, digital certificate processing, enforcement of device-related permissions, etc.) to ensure to security and safety of the IMD. Firmware 200 may also include battery management/charging firmware module 207 having executable instructions to control the operations of the IMD battery and recharging operations for the battery (if applicable to the specific IMD). It is noted that battery recharging operations may be performed via an external charging device (e.g., external charging device 165 of FIG. 1), as described above.

In some representative embodiments, multiple ones of firmware modules 200-207 include executable-instructions to generate code path data. The code path data is data indicative of execution of specific code that may permit examination of the path of execution through one or more firmware modules and/or the timing of such execution. In some embodiments, as firmware instructions are executed, code identifiers are placed into one or more queues, stacks, buffers, or other suitable memory structures that identify execution of a specific portion of a firmware module. For example, an address or other location identifier may be placed into a given buffer when execution of a respective firmware module reaches a specific point in the instructions of the respective firmware module. In some embodiments, timing information (e.g., from a system/device clock) may be included with in the code path identifier data to facilitate subsequent analysis of the order and/or timing of execution of specific code paths. The stored code identifiers may be maintained in volatile memory or non-volatile memory until retrieved, such as via communication to an external device (e.g., a patient controller device, a clinician programmer device, a manufacture diagnostic service or device, such as a central therapy management platform provided by a manufacturer of an IMD, or other external devices). It is noted that when stored in non-volatile memory, the code identifiers may be transferred to non-volatile memory if the IMD enters a low power state (i.e., when the current charge level of a batter of the IMD falls below a threshold charge level).

In some embodiments, tracing code may be embedded in the firmware code to place the code path identifiers into the respective buffer or other memory structure. The tracing code may call a function or subroutine that places the data into the appropriate buffer or memory structure or passes the code path data to another process for subsequent processing. The function or subroutine call may include the respective identifier of the code location or address as a parameter. Alternatively, the called function or subroutine may obtain such information automatically by retrieving a return address from an applicable processor-stack or register. However implemented, during execution of the respective firmware modules (as executed in real-time in operation of the IMD after implantation in the patient), data indicative of execution of firmware code at specific firmware locations and/or addresses is generated or provided for subsequent/additional processing. It is possible to generate data indicative of execution of specific firmware code paths without embedding in-line executable code in the firmware modules themselves. For example, firmware modules may be executed in one or more virtual machines and executable-instructions or code external to the firmware module(s) may examine execution at the virtual machine level to generate the code path data. However, such an implementation imposes additional processing-overhead and may not be suitable given the processing capability of certain IMDs. Accordingly, for some IMDs, it may be preferred to limit or reduce the overhead associated with the code path tracing operations.

In FIG. 2, firmware 200 is also shown to include firmware supervisory module 208. Firmware supervisory module 208 may include executable instructions to monitor the operations of the various other firmware modules. For example, if a firmware supervisory module 208 detects that a respective firmware module ceases properly working, firmware supervisory module 208 may include executable-instructions for corrective operations such as restarting the firmware module. Additionally, in some representative embodiments, firmware supervisory module 208 may be configured to process code path information to monitor the state of the respective firmware modules. Exemplary aspects of processing the code path information and responses to the processing of the code path information are described in more detail below.

Although various firmware modules are shown as discrete modules in FIG. 2, it is to be understood that firmware modules may be combined, organized in a hierarchical manner, omitted, and/or supplemented as appropriate for a given device. Additionally, functionality of the IMD may be supported by a single firmware module or may be supported by multiple firmware modules. For example, delivery of therapy to a patient may be controlled, in some implementations, by therapy firmware module 204, while in other implementations delivery of therapy to the patient may be controlled by a combination of modules (e.g., therapy module 204 may control generation of electrical pulses, sensor firmware module 202 may capture sensor data before, during or after delivery of the electrical pulses, and closed-loop module 205 may determine whether to modify one or more stimulation parameters based on the sensor data).

Figure 3:
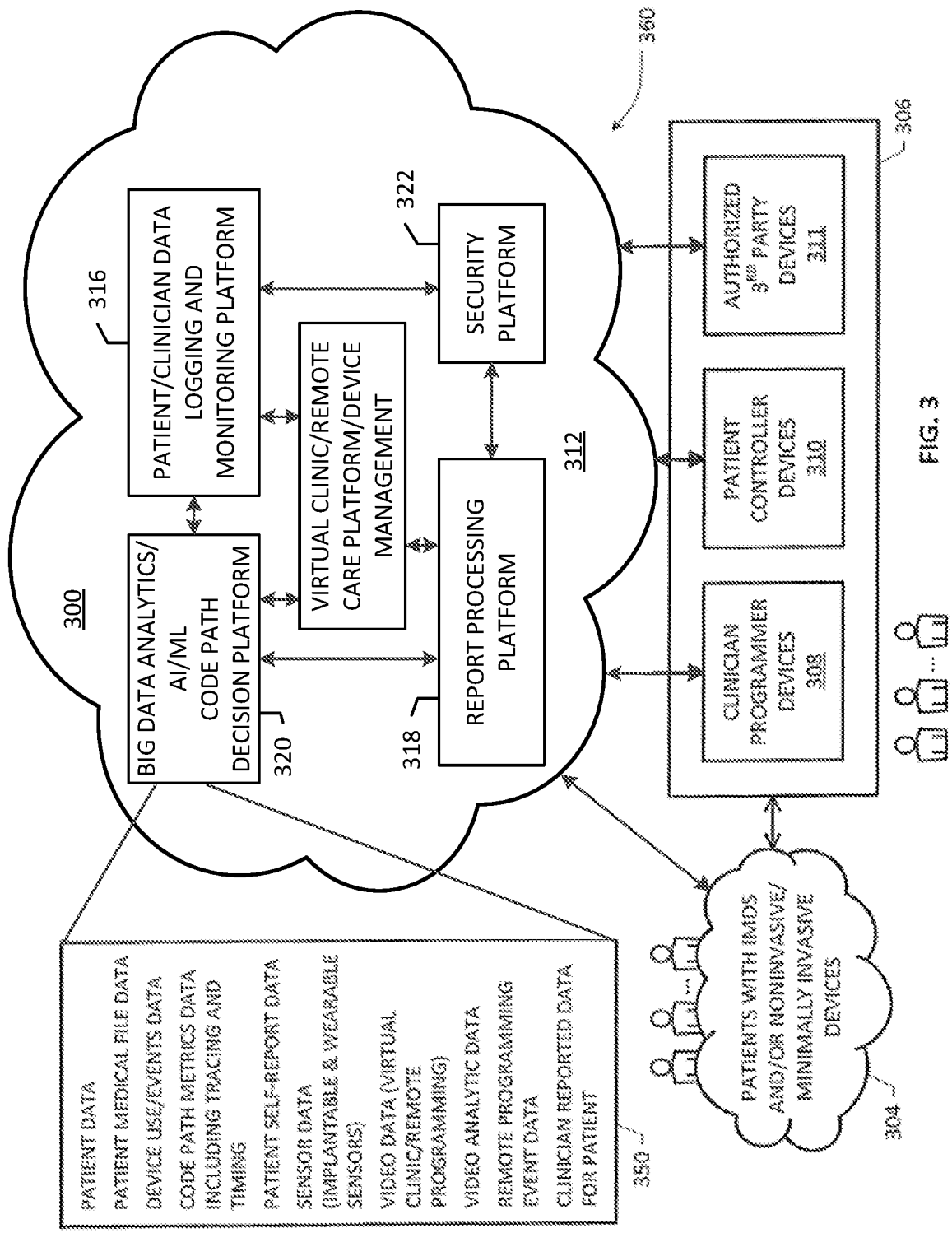
FIG. 3 depicts an example network deployment scenario with respect to managing multiple IMDs and other user equipment (UE) devices wherein code path metrics from multiple IMDs may be applied for purposes of some embodiments of the present disclosure.

FIG. 3 depicts an example network deployment scenario with respect to managing multiple IMDs and other user equipment (UE) devices where code path metrics from multiple IMDs may be processed using artificial intelligence (AI) and machine learning (ML) modeling techniques for purposes of IMD management and code path selection/optimization according to some embodiments of the present disclosure. In an example arrangement, a digital healthcare network architecture may involve various network-based components, subsystems, service nodes etc., as well as myriad of end user deployments concerning patients, clinicians and authorized third-party agents as illustrated in FIG. 3, where one or more embodiments of the present patent disclosure may be practiced for providing AI/ML-based code path analytics and decision-making functionality with respect to managing individual IMDs according to some implementations. In one arrangement, example architecture or network environment 360 may include one or more virtual clinic platforms 314, which may include device management nodes, remote data logging platforms 316, patient/clinician report processing platforms 318, data analytics platform 320 operative to receive various pieces of data, including IMD code path tracing, code path timing data, code path metrics, and/or firmware power-consumption or other firmware operational data, and security/authentication platforms 322, each of which will be described in detail further below.

It should be appreciated that at least some of the foregoing platforms, nodes, network components, etc., may be configured and/or deployed as an integrated digital health infrastructure 312 that may be configured as a distributed datacenter or cloud-based service infrastructure (e.g., disposed in a public cloud, a private cloud, or a hybrid cloud, involving at least a portion of the Internet, other cloud-based deployments, or combinations thereof). One or more pools of patients having a myriad of health conditions and/or receiving assorted treatments, including neurostimulation therapies such as DBS, SCS, DRG, etc., who may be geographically distributed in various locations, areas, regions, and the like, are collectively shown at reference numeral 304, where individual patients may be provided with one or more suitable IMDs/IPGs, other personal biomedical devices, etc., depending on respective patients' health conditions and/or treatments and the respective firmware code of each patient's IMD may be instrumented for providing tracing and timing data metrics to a network node, such as data analytics platform(s) 320.

A plurality of clinician programmer (CP) devices 308, patient controller (PC) devices 310, and authorized third-party devices 311 associated with respective users (e.g., clinicians, medical professionals, patients and authorized agents thereof) may be deployed as external devices 306 that may be configured to interact with patients' IMDs/IPGs for effectuating therapy, monitoring, data logging, secure file access and transfer, etc., via local communication paths or over network-based remote communication paths established in conjunction with the digital health infrastructure network 312 upon executing suitable authentication protocols that may be implemented in association with one or more components of integrated digital health infrastructure 312.

Example CP device 308 may permit programming of an IMD/IPG (e.g., IMD 150 of FIG. 1) to provide a number of different stimulation patterns or therapies to the patient as appropriate for a given patient and/or disorder. For purposes of the present disclosure, reference to and description of a particular IPG depicted in the Figures may generally apply to other IPGs/IMDs illustrated in other drawing Figures, mutatis mutandis, unless otherwise stated. In general, examples of different stimulation therapies may include conventional tonic stimulation (e.g., continuous train of stimulation pulses at a fixed rate), BURSTDR™ stimulation (e.g., bursts of pulses repeated at a high rate interspersed with quiescent periods with or without duty cycling) or other types of burst stimulation, "high frequency" stimulation (e.g., a continuous train of stimulation pulses at 10,000 Hz), noise stimulation (e.g., series of stimulation pulses with randomized pulse characteristics such as pulse amplitude to achieve a desired frequency domain profile). It is noted that the exemplary types of stimulation described above have been provided for purposes of illustration, rather than by way of limitation and that any suitable stimulation pattern or combination thereof can be provided by an IPG that may be effectuated based on the execution of a plurality of instrumented firmware modules according to some embodiments.

Appropriate code path metrics data from individual IMD/IPG devices may be provided as part of patient data 350, which may be aggregated by data analytics platform 320 for purposes of generating appropriately trained code path decision engines configured to effectuate code path categorization, etc., for purposes of some embodiments of the present patent disclosure.

In one arrangement, example architecture 360 may encompass a hierarchical/heterogeneous network arrangement comprised of one or more fronthaul radio access network (RAN) portions or layers, one or more backhaul portions or layers, and one or more core network portions or layers, each of which may in turn include appropriate telecommunications infrastructure elements, components, etc., cooperatively configured for effectuating a digital healthcare ecosystem involving patients' IMDs and/or devices 304, external devices 306, and one or more components of the digital health infrastructure network 312. In an aspect, at least a portion of the components of the infrastructure network 312 may be operative as a cloud-based system for purposes of some embodiments herein as noted above. Further, at least a portion of the components of the digital health infrastructure network 312, one or more patients' IMDs and/or devices 304, and one or more external devices 306 may be configured as a code path analytics system 300 that may be interfaced with other network systems configured to execute suitable medical/health software applications in a cooperative fashion (e.g., in a server-client relationship) including various aspects of device management, remote patient monitoring, telemedicine/telehealth applications, remote care therapy, etc.

Although not specifically shown in FIG. 3, example PC devices 304 may be configured to interoperate with smart wearable devices, e.g., for various purposes relating to therapy, data monitoring, data logging, code path metrics data storage/transfer, etc., as previously noted.

Figure 4:
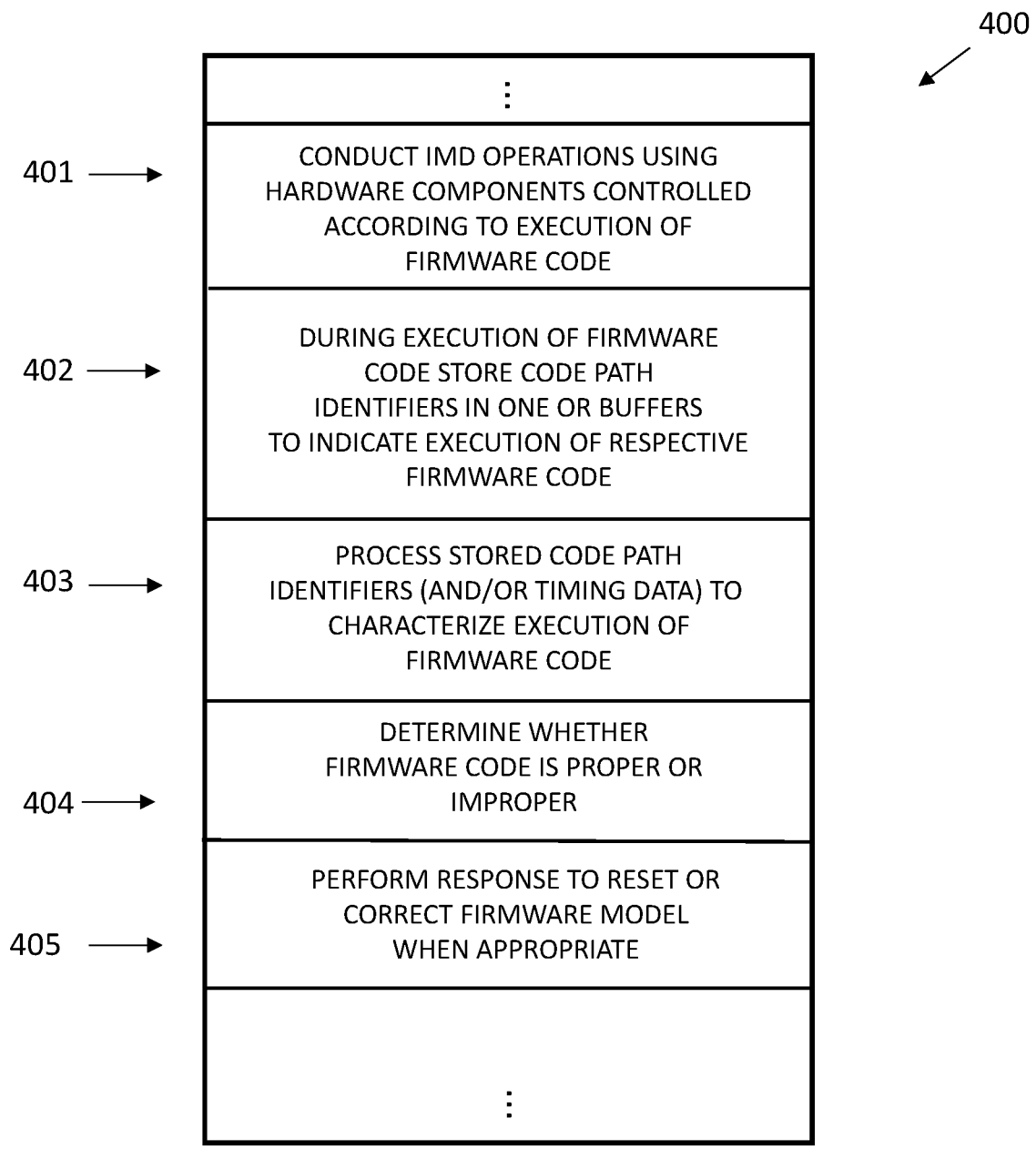
FIG. 4 depicts a flowchart of example IMD operations according to some representative embodiments.

Referring to FIG. 4, a flowchart of exemplary IMD operations according to some representative embodiments is shown as a method 400. As explained above with reference to FIG. 2, IMDs operating in accordance with the present disclosure may include one or more firmware modules having executable code to control various operations of the IMDs. As shown at 401, method 400 includes conducting IMD operations using hardware components controlled according to execution of firmware code. The firmware code may correspond to executable instructions to control various operations of the IMDs, as explained above with reference to FIG. 2.

At 402, the method 400 includes storing code path identifiers in one or more buffers to indicate execution of respective firmware code. For example, and as explained above with reference to FIG. 2, during execution of firmware code by a particular firmware module code identifiers may be stored in memory (e.g., one or more buffers, registers, and the like) to log the sequence of firmware code executed by each firmware module of an IMD.

At 403, the method includes processing the stored code path identifiers to characterize execution of firmware code. As explained above with reference to FIG. 2, in some aspects the code identifiers generated during execution of the firmware code may be stored with timing information (e.g., timestamps, etc.) to facilitate analysis of timing information with respect to execution of firmware code. For example, the timing information may be used to arrange the code identifiers in order over time, evaluate an amount of time required to execute one or more pieces of firmware code, or other types of temporal analysis.

At 404, the method 400 includes determining whether firmware code is proper or improper. By way of non-limiting example, determining whether the firmware code is proper or improper may include calculating a deviation metric representing a difference between an observed firmware execution for a respective firmware module and baseline code execution defined for the respective firmware module. If the deviation metric satisfies a threshold tolerance (i.e., the deviation metric is less than or equal to the threshold tolerance, or less than the threshold tolerance) then the firmware code may be determined to be proper, but if the deviation metric does not satisfy the threshold tolerance (i.e., the deviation metric is greater than the threshold tolerance, or greater than or equal to the threshold tolerance). As another non-limiting example, determining whether the firmware code is proper or improper may include calculating at least one power consumption metric using one or more respective calculated code path metrics. It is noted that the exemplary determinations described above have been provided for purposes of illustration, rather than by way of limitation and that other factors and logic may be used to determine whether firmware code is proper or improper.

At 405, the method 400 includes initiating one or more actions based on the outcome of the determining performed at 404. For example, if the firmware code is determined to be improper, a reset or correct firmware model may be initialized to reset or correct one or more errors in the firmware of a particular IMD. For example, at least one of the firmware modules (e.g., the firmware modules of FIG. 2) may be reset or a power overconsumption flag may be generated upon determining that the power consumption metric indicates improper IMD operations. As another example, the one or more actions may include generating an error state notification with respect to a firmware module if the deviation metric does not satisfy the threshold tolerance. Additionally or alternatively, if the firmware code is determined to be proper no action may be performed (i.e., because the IMD is operating properly). In an aspect, a record may be recorded to a database to indicate the outcome of the determining at 404 and/or any actions taken at 405. It is noted that the exemplary actions described above have been provided for purposes of illustration, rather than by way of limitation and that other actions may be performed based on whether firmware code is determined to be proper or improper. Exemplary aspects of the various operations of the method 400 are described in more detail below.

Figure 5:
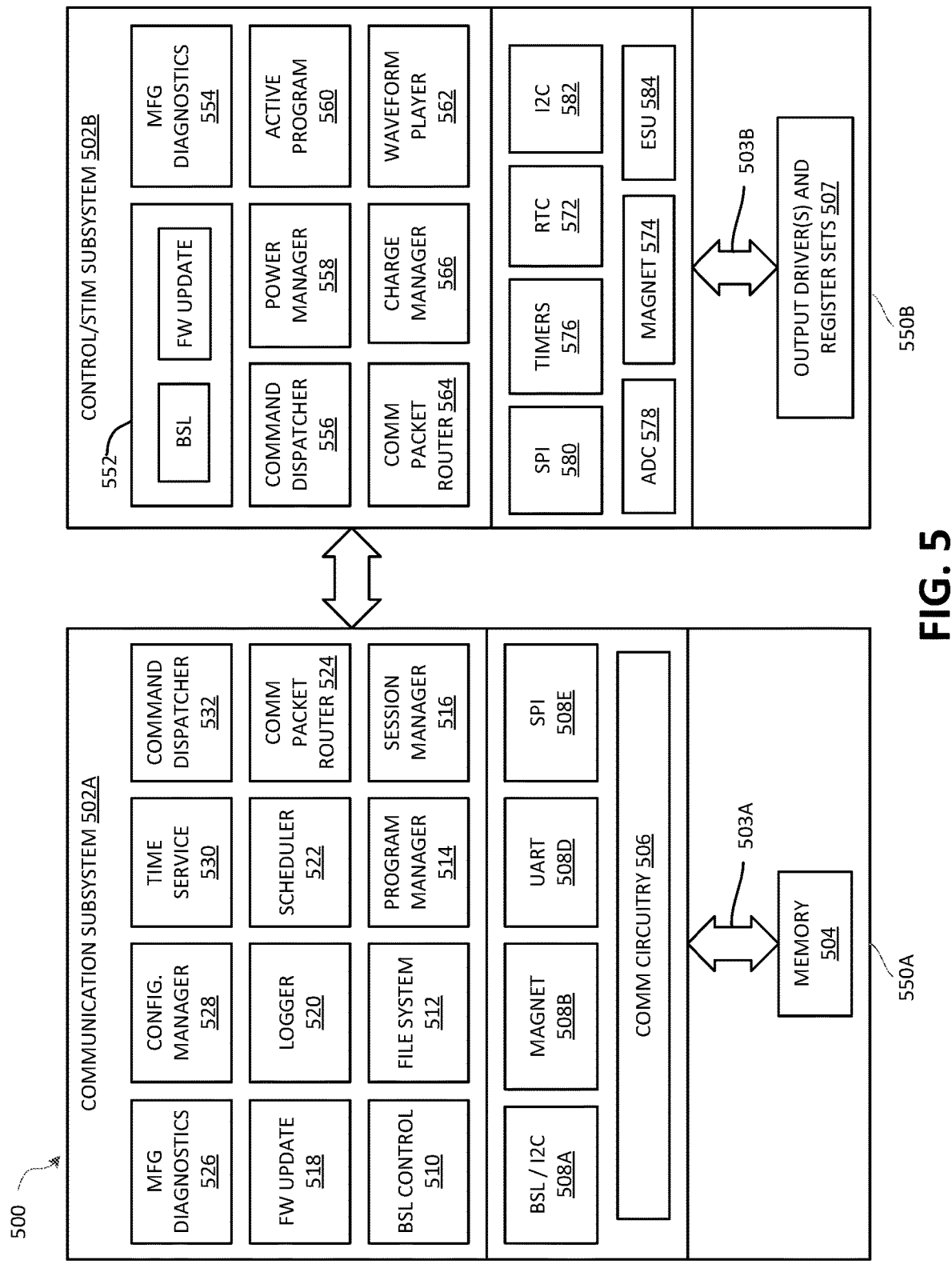
FIG. 5 depicts a block diagram of an IMD having a segregated functional architecture including multiple subsystems according to some representative embodiments of the present disclosure.

In some further examples, organizational structure of respective firmware modules may correspond to hardware components of a given IMD. For example, groups of firmware modules may be organized for specific device functionality that operate with related hardware components. For example, FIG. 5 depicts a block diagram of an IMD 500 having a segregated functional architecture including multiple subsystems and related firmware modules according to some representative embodiments of the present disclosure. Broadly, the hardware/software functionalities of IMD 500 may be partitioned into a communication portion 502A and a control/stimulation portion 502B, where each portion may be implemented to be controlled by respective processors/microcontrollers (not shown). Although multiple processors are described, other embodiments may operate with a single processor component as appropriate for a given device. In some arrangements, each respective processor/microcontroller of IMD 500 may execute an independent real-time operating system (not shown) and may execute respective firmware modules to implement the various device operations using the applicable hardware components.

Further, for IMD 500, sets 550A and 550B of circuitry/hardware components may be provided. The respective circuitry/hardware components need not be physically separated in the device or implemented in any specific manner. Sets 550A and 550B are depicted in FIG. 5 in a manner that corresponds to the various firmware modulates controlling device operations for clarity of discussion. However, one or more of the circuitry/hardware components of sets 550A and 550B may be integrated together (functionally or physically) in any suitable manner (e.g., one or more integrated circuit components).

Serial peripheral interfaces (SPIs) 508E and SPI 580 provide respective interfaces 503A, 503B, respectively, to memory 504 and output drivers/register sets 507. Memory 504 may store a plurality of therapy program records received from an authorized external device or a medical/healthcare provider network node. Output driver(s) circuit 507 may be configured to generate electrical pulses to select electrodes depending on respective stimulation parameters corresponding to an active therapy program being delivered to a patient associated with IMD 150.

Communication circuitry 506 may be configured to interface with a suitable antenna (not shown) to communicate with one or more external devices (e.g., a patient controller device, a clinician programmer device, etc.). The communication with one or more external devices may include conducting communications for securing the operations of device 500 (e.g., pairing with authorized devices, verification of permitted programming, authenticating external device identity and permissions, verifying digital signatures, encrypting/decrypting data, etc.). The communication with one or more external devices may include conducting communications for controlling therapy provided to the patient (e.g., receiving one or more program instructions specifying stimulation parameters for a therapy program, receiving or updating stimulation programs, etc.). The communication with one or more external devices may provide patient data (e.g., sensed physiological data) or device data to one or more external devices. In one arrangement, communication circuitry may be conducted using BLUETOOTH™ communications (e.g., using the BLE 5.0 standard).

Various communication interface and other subsystem components may be provided: bootstrap or boot loader (BSL) and inter-integrated circuit ($I^2C$) manager 508A, magnet communications interface manager 508B, Universal Asynchronous Receiver/Transmitter (UART) manager 508D, and SPI manager 508E.

In one arrangement, a plurality of firmware modules of communication subsystem 502A may include: BSL control 510, file system 512, program record manager 514, session manager 516, firmware (FW) update module 518, code path metrics data logger 520, task/event scheduler 522, packet router 524, manufacturer diagnostics 526, configuration manager 528, time service module 530, and command dispatcher module 532. In some examples, program record manager 514 may be configured to utilize at least some aspects of one or more of the foregoing modules to effectuate a program record transfer from memory 504 to control subsystem 502B via a suitable communication interface.

In some embodiments, IMD 500 may be adapted for inter-subsystem communication between subsystems 502A and 502B, e.g., including data and signaling/control communications. For example, inter-subsystem reset communications, BSL/$I^2C$ communications, SPI communications, etc. may be effectuated between communication subsystem 502A and control subsystem 502B.

In some embodiments, control subsystem 502B may therefore include, without limitation, the following: BSL/FW update firmware module 552, manufacturer firmware diagnostics 554, command dispatcher firmware module 556, power manager firmware module 558, active program firmware module 560, waveform player firmware module 562, charge manager firmware module 566, and packet router firmware module 564.

Further, various communication interface components may be provided for operations of control subsystem 502B, such as: magnet communications interface component 574, SPI manager component 580, and $I^2C$ component 582. Control subsystem 502B may also include various hardware components such as: real-time clock (RTC) modules 572, timers 576, analog to digital (A/D) converters 578, and electrosurgical unit (ESU) 584. In some embodiments, certain components may be shared for respective subsystem operations (although a logical separation is shown in FIG. 5) between the respective subsystems 502A and 502B. Some of the timing modules may be used to generate code path data and/or code path flow metrics according to some embodiments.

In one arrangement, waveform player 562 may be configured as a driver to output driver circuitry 507 operative under control of firmware based on a selected program record provided to the active program module 560, where appropriate stimulation may be provided by output driver circuitry 507 to select electrodes according to the pulse definitions in the program record. Although waveform player 562 is described in this manner, any suitable code to manage or transfer stimulation parameters to control pulse generating circuitry may be employed according to some embodiments. Output driver circuitry 507 may be provided with a leads interface (not specifically shown in FIG. 5) that may be configured as a lead-agnostic interface regardless of which specific electrodes are selected for use. In some embodiments, characteristics such as contact surface area and lead impedance due to length and materials may be accounted for and handled at application software level.

In some example embodiments, magnet communication interface(s) 508B and/or 574 may be utilized in a scenario where a magnet may be used as an additional or alternative control or triggering device based on sensing a magnetic field such that different modes may be accomplished by detecting magnetic events of varying encoded durations. For example, the magnet may be brought within the proximity or vicinity of IMD 500 for a particular time duration (e.g., a number of seconds) and then removed. The duration and state of the device may then be used to interpret this event as a specific action. Depending on implementation, magnet interface(s) may be configured to provide one or more of the following functionalities: alternative method of ON/OFF control of stimulation; acknowledgement of physical presence for security challenges required by operations such as bonding and firmware download; and restore/disable BLE communications. Additional details regarding the initiation and control of a bi-directional communication link between two devices using a proximate triggering device may be found in U.S. Pat. No. 9,288,614, entitled "SYSTEMS AND METHODS FOR INITIATING A COMMUNICATION LINK BETWEEN AN IMPLANTABLE MEDICAL DEVICE AND AN EXTERNAL DEVICE", the content of which is incorporated by reference herein.

Functionally, data may be transmitted and/or received over BLE or UART interfaces of communication subsystem 502A, which may be processed by a routing protocol executed by communications packet router 524 for determining the destination and delivering the packets to the appropriate endpoint for further processing (e.g., in association with command dispatcher 532). Inter-processor or inter-module communications may be effectuated over SPI or using other techniques, as previously noted.

Configuration manager 528 may be responsible for transitioning between IMD states, such as between a firmware update mode, a surgery mode, a magnetic resonance imaging (MRI) mode, a local/remote therapy mode, a standby mode, a trial setting mode, a diagnostics mode, an airplane ready mode, and the like. Depending on implementation, such transitions may cause playback of a select program record or a default program record by waveform player 562, which may be effectuated by the execution of corresponding set(s) of instrumented firmware modules, that may give rise to different code paths and associated code path metrics in some arrangements, as described in more detail below.

In one example embodiment, file system module 512 may be configured to provide access and data management of persistent data stored in memory 504, which may be partitioned into multiple virtual drives to maintain control of resource allocation. In an aspect, the entire storage space of memory 504 may be treated as a virtual disk drive. A fixed number of bytes may be allocated to each partition such that when a partition reaches capacity it may not be allowed to consume additional space from other partitions. In one arrangement, provisioning of the file system may provide individual partitions for diagnostic files, code path metrics data and analytics, program records, and space allocated for use by the therapy/remote application(s) as needed.

In one arrangement, programs manager or program records manager 514 is responsible for maintaining and managing the program records stored on memory 504 according to file system module 512. In one arrangement, select programs or program records may be loaded from the data store (e.g., memory 504) to the active program area 560 in control subsystem 502B through the operation of program records manager/module 514. Further, program records manager/module 514 is operative to facilitate saving and/or downloading of programs to the data store in addition to performing operations such as delete, copy, and read with respect to stimulation program records.

Figure 12:
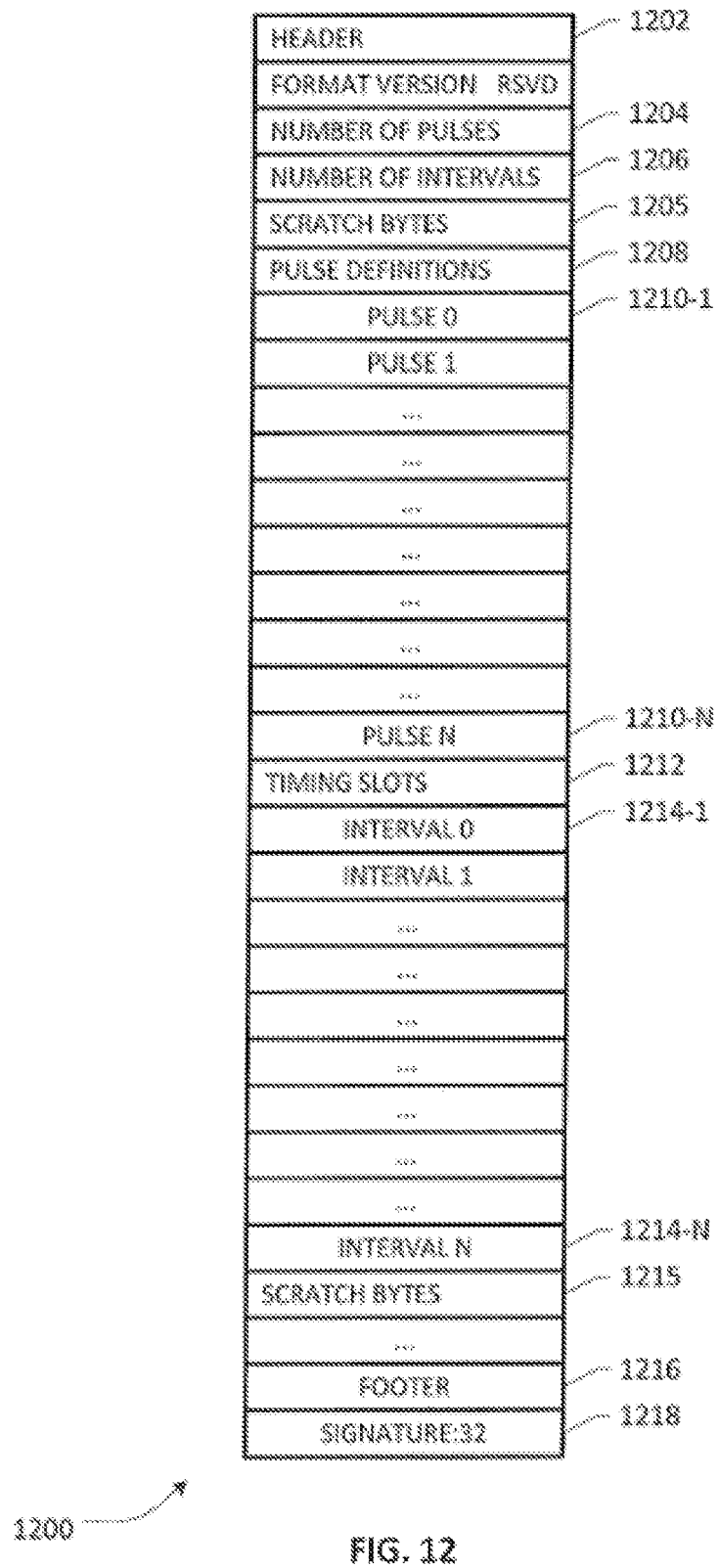
FIG. 12 depicts an example program record including variable pulse definitions and time intervals for use by a waveform player for energizing a select set of electrodes that may be managed by different code paths based on respective metrics.

Turning to FIG. 12, depicted therein is an example program record and associated format including variable pulse definitions and time intervals for use by a waveform player for energizing a select set of electrodes that may be managed by different code paths based on respective metrics according to an embodiment of the present patent disclosure. In one arrangement, a program or program record 1200 may include a header 1202 which identifies the version of the program record, any global conditions to be used in playing the record, the number of pulses 1204, and number of intervals 1206, followed by the pulse definitions 1208, interval/time slot definitions 1212, meta-data storage, and then followed by a footer 1216 and appended by a digital signature 1218. A pulse definition is a set of pulse characteristics that may be applied by or during an interval. In one arrangement, an interval defines the time until the next pulse. In some arrangements, example program record format 1200 may also optionally contain one or several scratch areas, which may include or provide for a certain amount of memory space to be set aside for any application data related to the program. By way of illustration, scratch areas 1205 and 1215 are exemplified in program record 1200. In one arrangement, signature 1218 comprises a digital signature operative to ensure data integrity with a Secure Hash Algorithm (SHA) hash (e.g., SHA256).

In one implementation, each time a program record is loaded from memory 504 into the active program module 560, the signature 1218 is checked, followed by a verification of the pulse and interval definitions to determine that the selected program record meets minimum/safe criteria for use as the active program by waveform player 562. In one arrangement, each interval indicates which pulse definition is to be output in that time interval. In general, record sizes may be configured to be variable with up to a certain number of pulse definitions (e.g., pulse definitions 1210-1 to 1210-N) and a certain number of timing intervals (e.g., 1214-1 to 1214-N), each of which may be independently determined or applied in some arrangements. As will be set forth below, the pulse definition parameters and/or timing intervals may be varied based on the code path metrics analysis in some embodiments. Additionally, combinations of the pulse definition parameters and/or associated timing intervals may be used as performance metrics for assessing whether an observed code path (e.g., for effectuating stimulation according to a selected stim set) is an acceptable code path or not (e.g., based on whether the observed pulse parametrics are within a threshold range of the desired settings), which may be used in predictive/adaptive code path categorization schemes according to some examples herein.

In one arrangement, programs manager module 514 of IMD 500 may be configured to provide support for overwriting default programming for certain types of modes (e.g., MRI mode, surgery mode, diagnostics and system impedance, trial mode, etc). For example, this may be accomplished through providing a process to specify a particular program record that will overwrite the system default method at initialization.

It will be appreciated that as the power and functionality of microcontrollers and processors used in IMDs/IPGs increases (whereby the devices may also be referred to as active implantable medical devices or AIMDs in some example implementations), so does the complexity of the code associated with the IMD subsystems. As code complexity grows, the number of unique code paths traversing respective sequences of firmware segments or modules for effectuating a functional subsystem also grows (e.g., in an exponential manner in some IMD implementations). This growth in complexity can lead to an increased probability of firmware bugs, misunderstood corner cases, customer misuse cases, and unexpected environmental input reactions. Whereas many of these code paths may allow the IMD device (or the particular subsystem or function involved) to continue to run, there is a possibility that unexpected and/or often undesirable outcomes for the patient or user may result, including, for example, diminished/unresponsive therapy, unresponsive controls, reduced device longevity or charging interval, reduced usability, or other undesired or unanticipated effects.

Due to the subtle nature of such impacts, sometimes the issue may not be identified until much later, or it can be confused with other root causes. For instance, if therapy is impacted without the user being aware, the patient and/or the clinician may interpret the issue as an inability of the device or an incompatibility of the patient's physiology with the device, which may lead to taking potentially drastic responses such as having the therapy altered in a significant or suboptimal way and/or having the IMD removed altogether.

Existing techniques such as deploying watchdog timers and brownout detectors to address issues found in firmware for IMDs are not effective, however, because of the increased code complexity. As such, these techniques are prone to misidentifying and/or being unaware of the underlying causes. Watchdog timers expect input from the firmware at periodic intervals, so that if the firmware stops or gets stuck and can't get back to the primary paths, it will reset the device. Brownout detectors monitor the voltage input to the device and hold it in reset while the voltage is below a certain threshold. Both these techniques have multiple issues, thereby rendering them undesirable in a variety of IMD deployment scenarios. For watchdog timers, they are unable to detect any issue that causes the execution flow to continue to traverse so-called "normal" paths that send the periodic update(s) to the watchdog. This means that many issues that may be associated with such flows are not identified (i.e., false negative identification). On the other hand, brownout detectors only react to issues that significantly impact the power usage, which also does not address most device issues that may require a more graduated response.

Furthermore, the foregoing methods only have one response to an issue and that is a full reset of the device. In general, this is invasive and/or inconvenient to the user due to the user interface not communicating, in addition to the therapy being stopped or suspended. Additionally, such a response can also lead to the device being put into an undesired state that needs clinical or user intervention to regain the original therapy. Moreover, if a reset does not solve the problem, the device may continue in a loop of continual resets making it non-functional for the user as well as for failure analysis. Existing solutions cannot therefore quantify the state of the device and autonomously and/or automatically correct issues or avoid nuisance alarms.

Examples described herein recognize the foregoing challenges and accordingly provide a scheme for obtaining and analyzing code path metrics to facilitate quantifying the current state of operation of an IMD.

Figure 6:
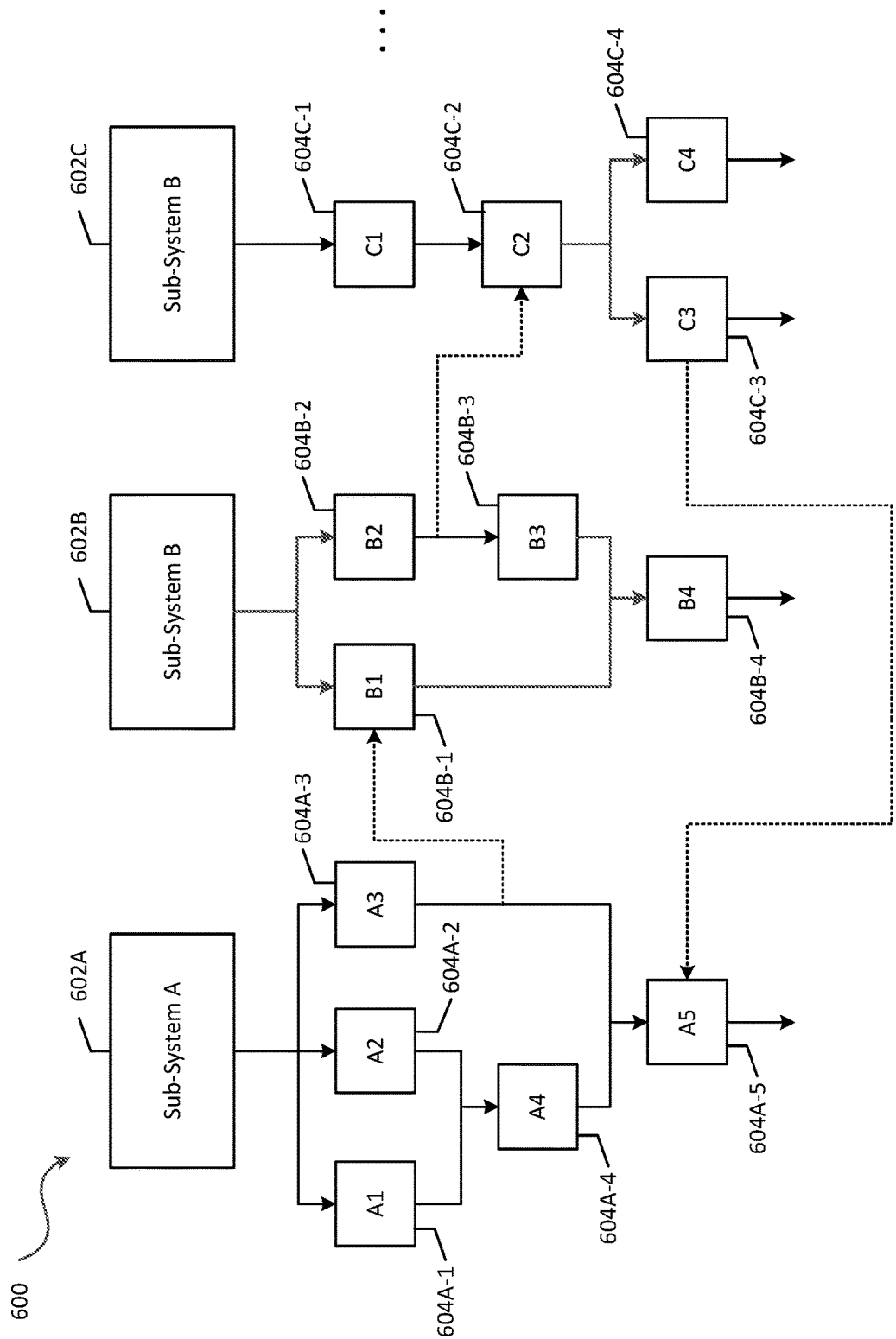
FIG. 6 depicts an example arrangement of a plurality of IMD subsystems and associated firmware modules in some representative embodiments of the present disclosure.
Figure 7:
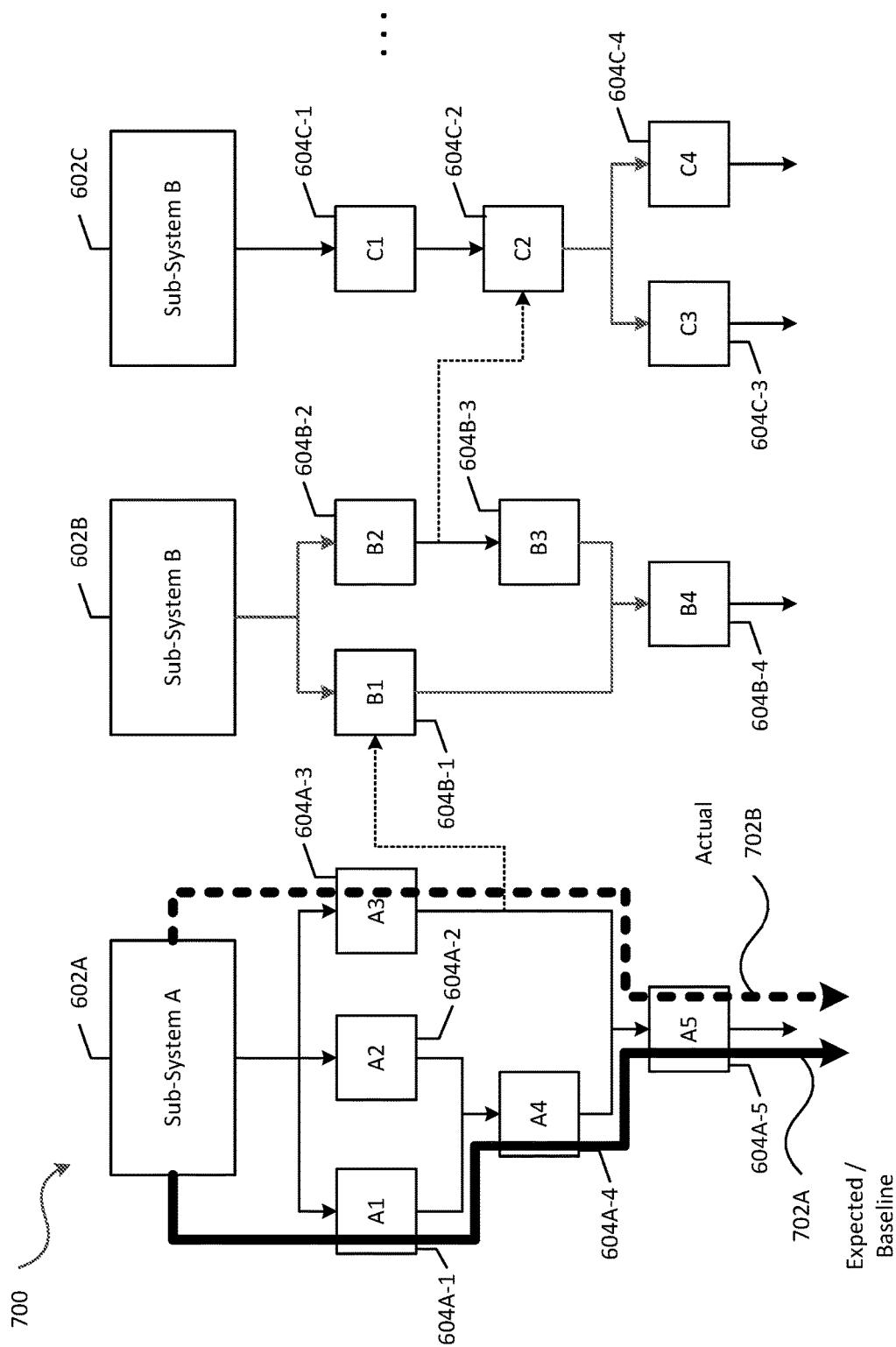
FIG. 7 depicts an example arrangement of a plurality of IMD subsystems wherein different firmware code paths may be undertaken for effectuating a device function in some representative embodiments of the present disclosure.
Figure 8:
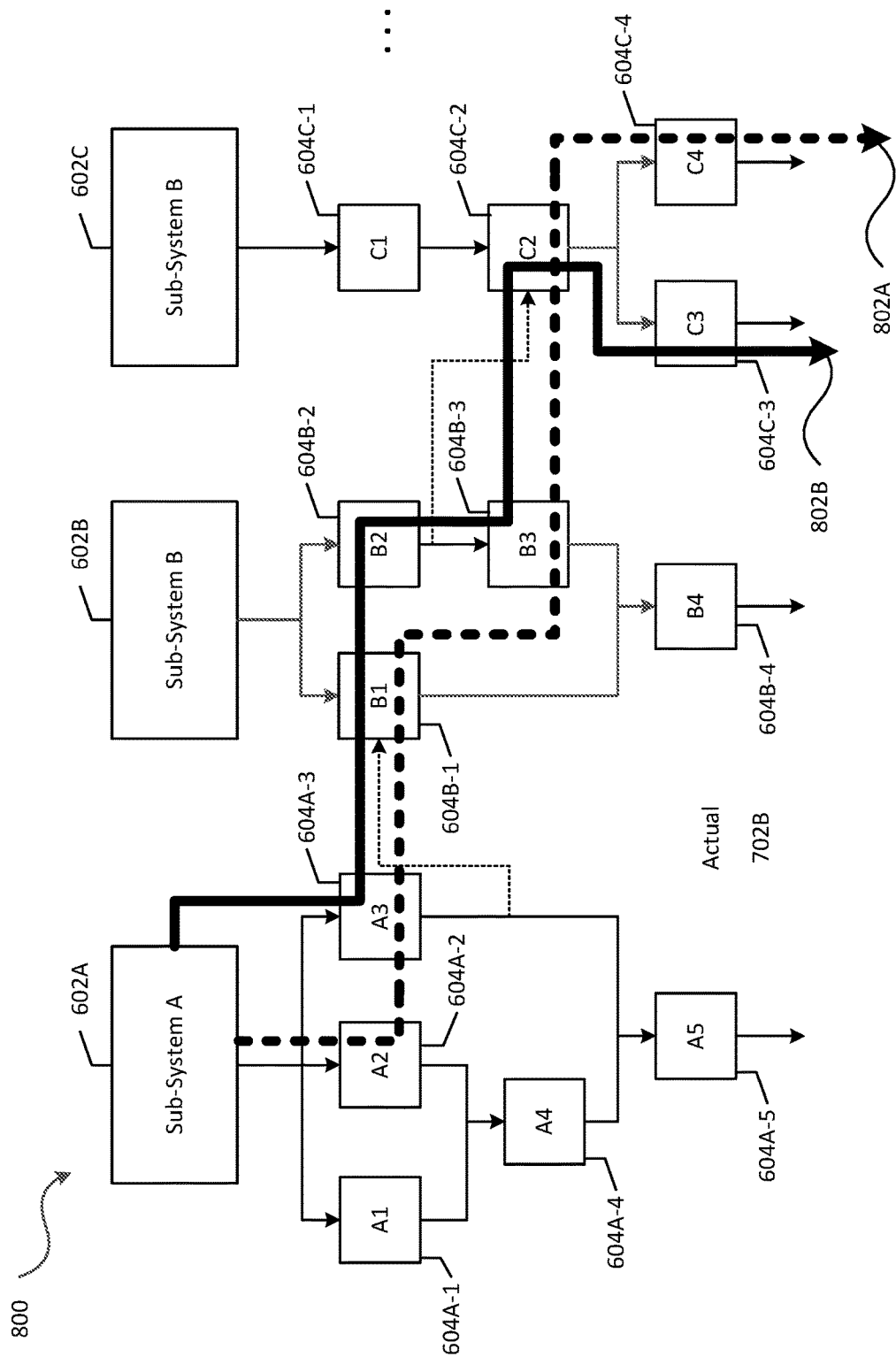
FIG. 8 depicts another example arrangement of a plurality of IMD subsystems wherein different firmware code paths may be undertaken for effectuating a device function in some representative embodiments of the present disclosure.

By way of generalization, FIGS. 6-8 illustrate example arrangements of IMD firmware subsystems managed by one or more firmware modules. Different code paths may be traversed during device operations following respective sets or sequences of firmware instructions. For example, the exemplary firmware subsystems shown in FIGS. 6-8 may be representative of any of the above-described or other IMD firmware subsystems. As will be seen further below, example embodiments may utilize code path/flow metrics corresponding to respective code path data generated during device operations to quantify the state of an IMD. In some embodiments, device operations are modified to react to code path data according to customized responses tailored to each subsystem or function of the IMD in various deployment scenarios.

Example arrangement 600 shown in FIG. 6 is illustrative of a plurality of firmware subsystems 602A-602C, each of which may be implemented with various sets of firmware instructions (i.e., executable code). The respective firmware subsystems may be involved in effectuating one or more corresponding device functions. Depending on implementation, example firmware modules or submodules may comprise one or more subroutines, internal function calls, system calls, procedures, subprograms, as well as calls to codebase segments that may be operative for the functionalities of other subsystems.

By way of illustration, firmware subsystem 602A may have a firmware codebase associated therewith that may have five segments of code, exemplified in FIGS. 6-8 as: A1 604A-1 through A5 604A-5, wherein the indices {1, 2, 3, 4, 5} represent code locations identified with appropriate code markers or unique identifiers as will be set forth in detail further below.

Likewise, firmware subsystem 602B may have a codebase that may be instrumented at four locations, shown in FIGS. 6-8 as: B1 604B-1 through B4 604B-4 identified with respective code markers or identifiers; and subsystem 604C may have a codebase that may be instrumented at four locations, shown in FIGS. 6-8 as: C1 604C-1 through C4 604C-4 identified with respective code markers or identifiers. Each subsystem's codebase may be organized into multiple modules or submodules as the case may be.

It should be appreciated that the codebase associated with a firmware subsystem may be organized into one or more modules, submodules, code segments, and/or code portions, without limitation. Accordingly, the markers or identifiers associated with the firmware code may be distributed among multiple such firmware modules, submodules, and/or portions. In some cases, the markers or identifiers may be disposed within a single module, submodule, or portion depending on implementation and/or application. Regardless of how a codebase is organized, a code path represents a series of instructions that are traversed during the execution of the functionality effectuated by the respective firmware code.

Further, during operation of an implantable device, the functionality of a subsystem may occur by executing one or more portions or segments of the associated codebase, as noted previously, thus traversing different code sequences or paths. Accordingly, at any given time, the functionality of subsystem 602A may be effectuated via any one of a plurality of separate code paths as exemplified in the example arrangement of FIG. 7.

By way of illustration, example code path 702A may comprise executing the codebase segments/modules in a sequence of markers comprising A1 604A-1, A4 604A-4 and A5 604A-5. In similar fashion, code path 702B may comprise a sequence of markers including A3 604A-3 and A5 604A-5. As will be described further below, one of the paths (e.g., path 702A) may be determined as an expected code path or a baseline code path based on historical data analytics, statistical analysis, AI/ML-based predictive modeling, supervised/non-supervised/semi-supervised learning, etc., whereas code path 702B may be an actual or observed code path (also sometimes referred to as a candidate path). Some example embodiments may be configured to evaluate the difference or deviation between the expected/baseline code path 702A and the actual/observed code path 702B and generate a graduated response depending on the function/subsystem involved, which may further include adjustments to therapy mode(s), stimulation settings, etc.

It shall be appreciated that this specific example considers one progression through the respective firmware code. In operation, execution of firmware will frequently proceed through multiple loops, iterations, or code flow logic and possibly proceed through different code paths during such loops, iterations, or code flow logic and the pattern of such progression may be analyzed according to some embodiments. However, for solely the purpose of discussing embodiments, a single progression through firmware code paths for multiple possible paths is discussed but embodiments are not limited to such single pass implementations.

Whereas some functions may involve invoking a single subsystem of the IMD, respectively, other functions may require the operation of multiple subsystems and may therefore involve executing code segments or modules from different codebases across the subsystems. In such execution scenarios, unique code paths for effectuating the functionality may traverse modules from different subsystems. Referring to FIG. 8, example arrangement 800 shows a code path 802A traversing markers A3 604A-3, B1 604B-1, B2 604B-2, B3 604B-3, C2 604C-2 and C3 604C-3 and a code path 802B traversing markers A2 604A-2, A3 604A-3, B1 604B-1, B3 604B-3, C2 604C-2 and C4 604C-4, wherein code path 802A may be determined, designated or otherwise obtained as a baseline or expected path and code path 802B may be an actual or observed code path.

For purposes of some examples herein, one or more device firmware codebase(s) may be instrumented to generate code path data and by analysis thereof to obtain tracing metrics and timing metrics (collectively referred to as code path metrics). This code path data may be used for determining or quantifying the IMD/subsystem state and generating suitable graduated response(s) with respect to the functionality of one or more device subsystems.

In view of the example IMD implementations and/or deployment discussed herein, set forth below is a non-exhaustive list of device subsystems for purposes of at least some examples herein: power-up routines (e.g., relating to initialization, reset and diagnostic subroutines), programming controllers and bootloaders, therapy output drivers (e.g., output drivers for stimulation as well as audio/video and other biological drivers), wireless communication controllers (e.g., for effectuating Bluetooth, BLE, WiFi, Zigbee, or more generally all applicable IEEE 802.11 and IEEE 802.15 communications, as well as NFC, inductive communications, etc.), internal device communication controllers (e.g., SPI, I²C, One-Wire, UART, etc.), test bus controllers, sensor drivers, analog-to-digital converter (ADC) controllers, general purpose input/output (GPIO) controllers, power management and fuel gauge controllers, user input handlers (e.g., near field communication (NFC), magnet detection, etc.), memory and file system management controllers, real-time and embedded operating systems, logging controllers, cybersecurity engines, machine learning engine drivers, wireless charging controllers, and any subsystem controlled by one or more firmware modules (e.g., that can be characterized by timing and/or code execution paths).

In some arrangements, code tracing may involve keeping a running log of unique firmware location markers or identifiers as the respective firmware instructions are executed. In some arrangements, the log may be configured to keep track of the most recent sequential paths executed by the device. In some arrangements, an actual path, paths, or pattern or paths traversed for a given subsystem may be checked against a known good path, paths or pattern of paths that the device is expected to run through.

In some arrangements, timing metrics may involve using onboard timers with configurable start and stop locations in the firmware that can be activated as necessary to measure the amount of time between key events or code locations associated with the codebase of a subsystem. Similar to the trace log, the timing information (also referred to as a timing interval log) may be checked against a known good range of timing for each subsystem's key event intervals.

In some configurations, the expected paths and timing metrics may be developed during the initial testing and development of the device, which may involve nonpatient, out-of-patient and/or in-patient trial mode operations of the device. Accordingly, the operation of the device after deployment in the field (e.g., after implanting in a patient) may be tested against the expected usage metrics (i.e., code paths involving location markers and/or the timing metrics) in order to ensure that the field operation stays within the bounds, thresholds, or ranges of the expected metrics data defined during the formal verification of the device. In some arrangements, detection of any device/subsystem behavior beyond or outside the expected usage thresholds with respect to a particular functionality may be flagged with suitable alarms and error state notifications that may be addressed in the field according to some embodiments.

As these usage metrics are quantifiable, they can also be used to numerically or quantitatively assess the status of the IMD in some embodiments. Accordingly, one or more graduated response protocols may be established with respect to any detected issues in the field, which may be customizable to each subsystem and/or function. For instance, a subsystem that is critical to safety or usage may have tighter restrictions and more stringent response protocols. Where a subsystem is focused on less critical functionalities (e.g., communications), the device may be configured to continue to operate with more errant behavior (e.g., out-of-bounds operation) in order to support device usage and failure analysis. In still further arrangements, as the usage metrics with respect to a given IMD device is going to be unique to each user/patient, the quantifiable metrics may be provided to an AI/ML-based expert system (e.g., the data analytics platform 320 of FIG. 3) to self-adapt the acceptable ranges of tracing and timing metrics by using suitable machine learning algorithms as will be set forth below.

Figure 9:
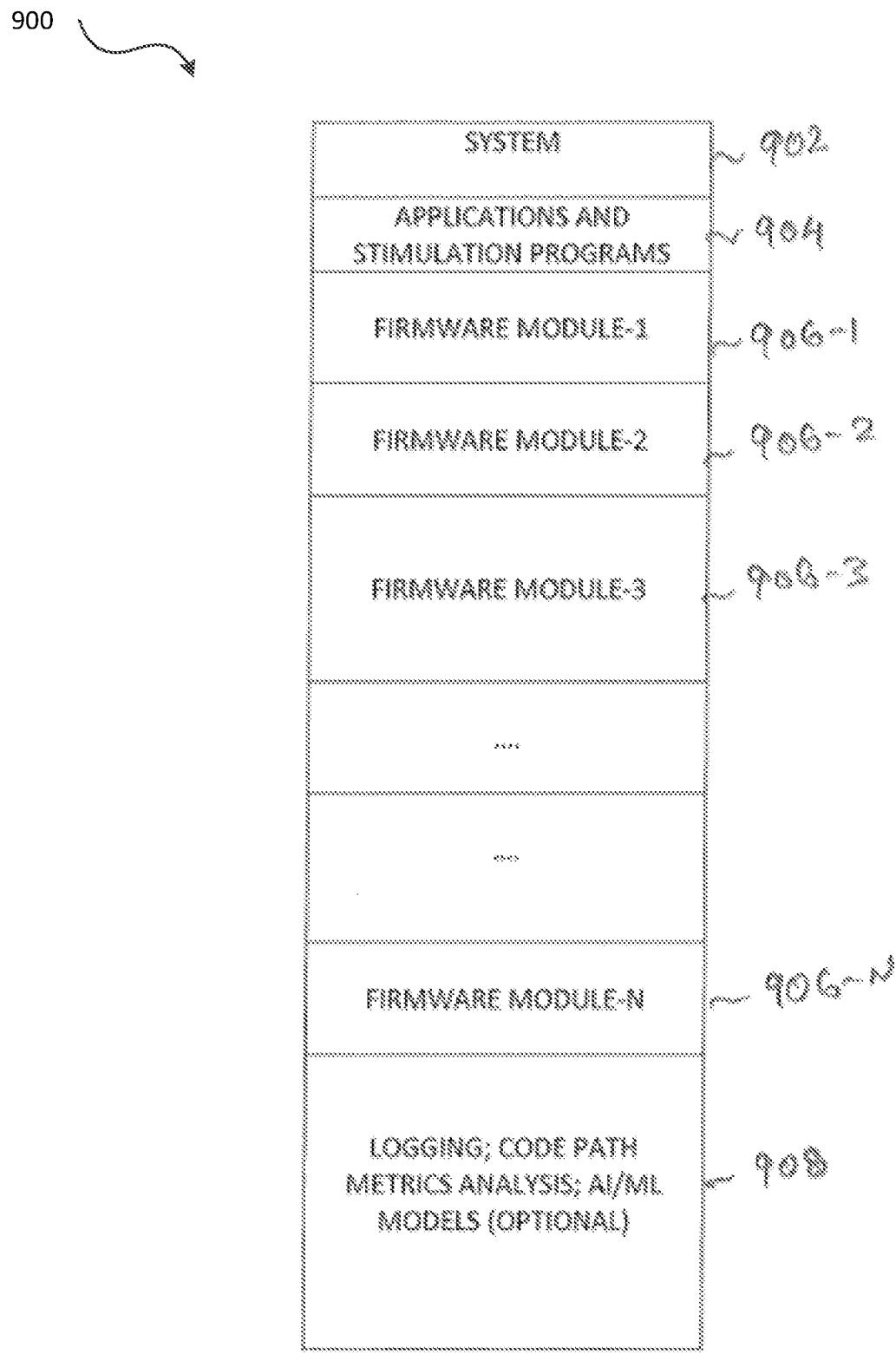
FIG. 9 depicts an example memory space arrangement of an IMD including a plurality of firmware modules according to some representative embodiments.

FIG. 9 depicts an example memory space arrangement of an IMD according to some representative embodiments. Example memory space or map 900 may include code and data, including a system code portion 902 and therapy applications/programs 904, wherein the therapy programs may comprise one or program records having pulse definition settings as described above. Further, a plurality of firmware modules 906-1 to 906-N may be provided, where one or more firmware modules may be executed to control one or more hardware components in order to effectuate one or more functions or functionalities of an IMD device. During execution of certain code paths of firmware modules 906-1 to 906-N, code path markers or identifiers are stored in one more arrays, queues, or other suitable data structures. Code diagnostics and logging portion 908 may comprise executable code for calculating code path metrics analytics from code path data stored in memory and/or AI/ML-based predictive/adaptive modeling (e.g., in a local, device-hosted analysis scenario) according to some implementations.

Figure 10:
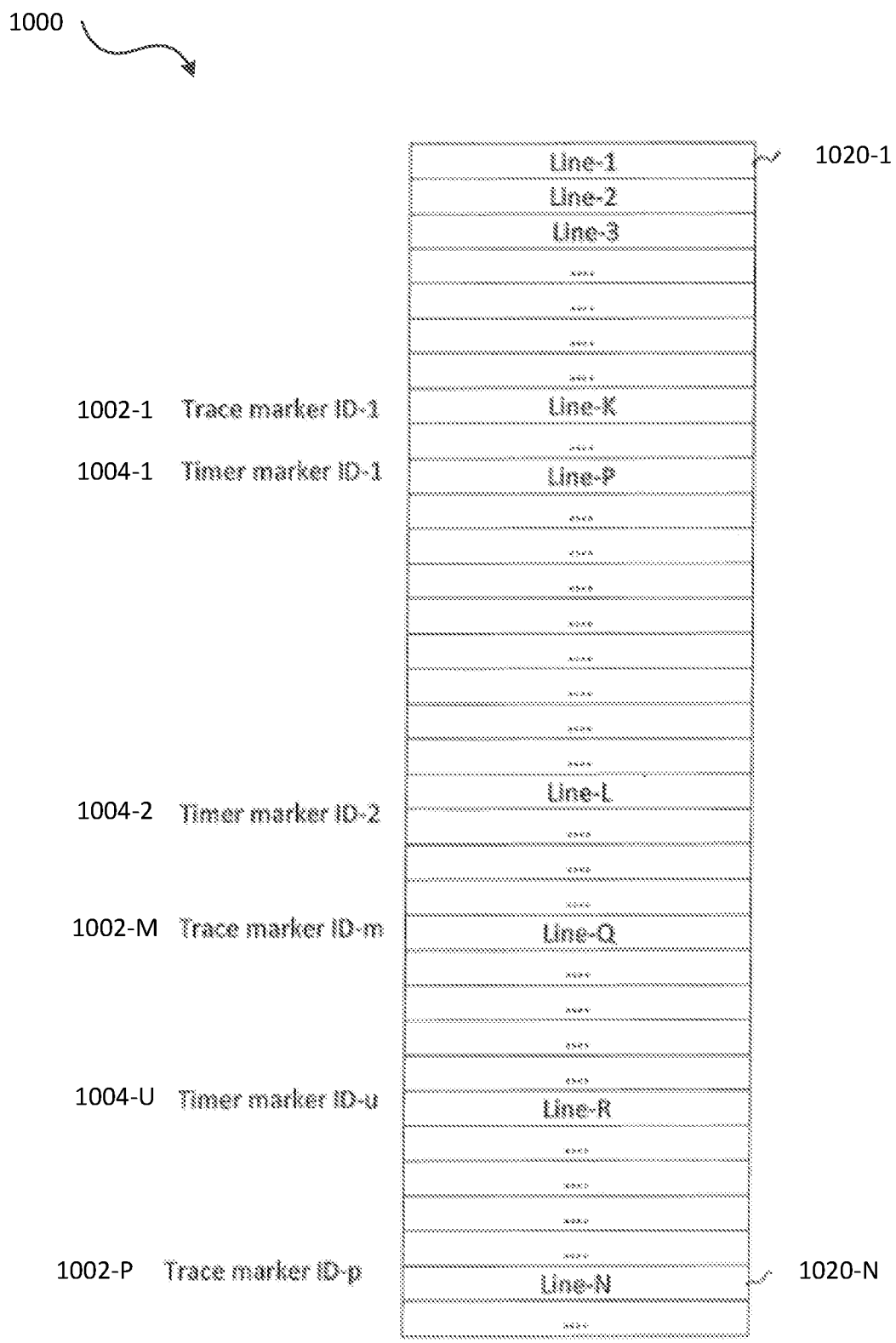
FIG. 10 depicts an example firmware codebase having tracing and timing instrumentation markers for obtaining code path flow metrics according to some representative embodiments.

FIG. 10 depicts an example firmware codebase having tracing and timing instrumentation markers according to some representative embodiments. By way of illustration, example codebase portion 1000 may be representative of one or more firmware segments corresponding to a single device subsystem and/or function in some arrangements. Alternatively, the codebase portion 1000 may be representative of firmware segments operative for effectuating multiple subsystems/functions. It will be realized that example codebase portion 1000 may be implemented in a variety of configurations based on the memory architecture and software control hierarchy of an IMD device.

As noted previously, code tracing involves instrumenting the code by defining unique identifiers or markers for appropriate components or locations of the firmware codebase, where the unique identifiers and/or locations may be customizable or selectable based on the objectives of instrumentation. When the code reaches any of these locations during execution, the corresponding custom/unique identifier(s) may be added to a memory buffer (or respective buffers corresponding to different code paths) or other suitable data structure in memory. The markers or identifiers may be added in sequential order for processing and analysis.

The number of locations utilized for tracking can be tailored to optimize the key resource needs of the design. For instance, a memory-constrained device may have less granular coverage with only a few markers per subsystem/function. A tracing metrics analytics module may be configured to utilize device level tracing to confirm that code coverage of a subsystem access is within the expected range. In another arrangement, a system may be configured to have a large number of markers (e.g., on the order of hundreds or more) per subsystem/function, thereby allowing for in-depth issue identification and custom control over responses.

Furthermore, the number of markers for code locations can be customized by subsystem/function, with more critical or error-prone subsystems/functions having more markers and less critical subsystems/functions having fewer markers in some example embodiments. Additionally, the depth of an example trace buffer and/or timing interval buffer (or more generally, a metrics buffer) may be configured for longer history or less memory usage depending on the needs of the design (e.g., as a code path metrics buffer optimization scheme). Still further, depending on implementation, code instrumentation can be source code instrumentation, binary code instrumentation, or both.

By way of illustration, example codebase portion 1000 of FIG. 10 is exemplified as a group of lines of code 1020-1 to 1020-N, where a plurality of trace markers or identifiers are provided with respect to a corresponding number of code locations. As shown, Line-K is identified with a trace marker ID-1 1002-1, Line-Q is identified with a trace marker ID-m 1002-M and Line-N is identified with a trace marker ID-p 1002-P. When the execution of the firmware code reaches each one of these locations, the respective trace marker or identifier of markers/identifiers 1002-1 through 1002-P is added to the relevant buffer. This may occur using tracing code embedded in the firmware code according to some embodiments. For example, a function call may be executed to pass a respective marker/identifier to a code tracing function. The code tracing function may then place the maker/identifier in the appropriate buffer (optionally, with a time-stamp using a system clock or timer). Upon completion of the function, the code control returns to the firmware location and resumes execution thereof. Although such in-line code tracing may be performed, any suitable executable code may be employed to place the code markers/identifiers into memory for additional processing and/or analysis.

In one arrangement, at the firmware subsystem level, a particular firmware subsystem may be configured to keep its own trace of the paths through the corresponding codebase portion(s). As noted previously, the set of code paths or patterns thereof may be checked periodically in some customizable configuration against a set of code paths or patterns known, determined, or otherwise characterized as appropriate for that firmware subsystem (e.g., baseline paths of the firmware subsystem), preferably based on a corresponding performance metrics associated with the executed functionality. If actual code path data or metrics deviates from the expected or known good path data or metrics, a firmware monitoring code may be configured to respond appropriately.

As shown in FIG. 7, the representative arrangement 700 therein illustrates an example of when the expected/baseline path 702A and the actual path 702B through the firmware deviate from each other. The markers associated with the expected path 702A illustratively comprise the sequence of markers corresponding to the respective codebase locations, e.g., [A1, A4, A5]. Likewise, the markers for the actual code path 702B comprise the marker sequence [A3, A5]. In an example arrangement, the deviation between the two paths 702A and 702B may be determined by a distance between the two ordered marker lists or sets. In an example arrangement, the deviation between the paths may be detectable by comparing the two marker lists at runtime (e.g., of the actual path), wherein an analytics module may be configured to flag any difference greater than a threshold (e.g., a delta or difference threshold level). Depending on implementation, the code path comparisons may be performed periodically for repetitive tasks (e.g., once for every predetermined number of accesses) in order to reduce the power and memory burden on the device. In additional or alternative arrangements, code path comparisons may be performed for every execution of the subsystem for high criticality functions. In such an example, the device may be configured to check the path step by step and respond prior to allowing the code to complete the path, e.g., similar to executing a codebase instrumented with breakpoints.

With respect to obtaining operating timing metrics, example embodiments may be configured to utilize one or more onboard clocks of the processor(s) or timers of an IMD in order to determine the timing intervals between various points in the execution of a codebase associated with a firmware subsystem or function. In some example embodiments, the timers may comprise hardware timer circuits associated with the device. In some embodiments, the code points or locations used in determining the operating timing intervals may be configurable (e.g., by providing timer flags associated with the respective code locations that can be enabled or disabled).

In some embodiments, timing metrics may be calculated from time data (e.g., from a system clock) that is stored in the code path data buffer(s) with the code path markers/identifiers. In other embodiments, when execution of firmware code reaches an identified location (if the corresponding access flag is enabled), a timer will be started and/or stopped at that location based on how the device or the subsystem is configured in an example implementation. In some example arrangements, the timer flags or markers may be enabled and disabled by an external user configuration device (e.g., a patient controller device, a clinician programmer device and/or an authorized third-party device such as external devices 160 of FIGS. 1 and/or 306 of FIG. 3 described hereinabove) and/or based on the mode that the IMD device is in.

Code path instrumentation and/or local analytics module may be provided for operation with an example external device. By way of illustration, if an IMD is providing electrical pulses according to a therapy program, such as in a therapy mode configured to output a waveform based on the program record 1200 set forth in reference to FIG. 12, a plurality of key timing statistics may be logged on the output electrical pulses (e.g., pulse widths, inter-pulse intervals, etc.), which may be checked against a timing interval log in some arrangements.

On the other hand, if the device is in standby mode, it may be more important to measure CPU awake time. Accordingly, an example embodiment may be configured such that a CPU monitoring subsystem or routine is appropriately instrumented for measuring the processor activity. Skilled artisans will recognize upon reference hereto that multiple concurrent timers may be configured in some arrangements using a combination of one or more system hardware components (e.g., a hardware clock) and firmware/software logic.

In some arrangements, similar to the location marker data of the code path metrics, timing flags can be configured to measure timing intervals within a firmware subsystem or across multiple firmware subsystems (e.g., at a higher functional/hierarchical level such as at the device level or at some partition level in a segregated architecture), essentially depending on the needs of a particular design. In an example configuration, once a particular timer is stopped based on reaching a corresponding code location, the final measurement or a relative time period (e.g., based on a starting timer) can be compared against the expected range of timing for that task, routine or code segment, etc., as may be predefined during formal testing.

Returning to FIG. 10, a plurality of timer flags or markers may be exemplified with respect to the representative instrumented codebase portion 1000. As shown in FIG. 10, timer flag 1004-1 may be defined to start timer when execution of the respective firmware instructions reaches Line-P. In a manner similar to storing code path markers or identifiers in buffers, the timing data may be generated by executing in-line code in the firmware that calls a function which, in turn, controls timer management. Upon starting (or stopping) the respective timer, the function then returns execution of firmware code back to appropriate location in codebase 1000. Any suitable set of instructions for starting and/or stopping respective timers may be employed within the firmware code according to other embodiments.

Timer flag 1004-U (associated with Line-R of the codebase 1000) may be defined to stop the timer previously started upon reaching Line-P. Likewise, timer flag 1004-2 may be defined to start another timer when execution reaches Line-L location of codebase 1000 with timer flag 1004-U defined for Line-R to stop that timer. As one skilled in the art will appreciate, the foregoing timer instrumentation examples are purely illustrative and in no way limiting as to how many timer flags and/or inter-event timing intervals may be concurrently set up in a representative embodiment of the present disclosure.

Using the start and stop operations described herein, the timing intervals defined by these timers may be stored in one or more buffers or other suitable data structures in memory for further processing and/or analysis. For example, for a given timer sequence, the start and stop locations in the code and the timing interval between execution of the firmware instructions between those locations may be stored in one or more suitable data structures for subsequent processing and/or analysis according to some embodiments.

In some examples, processing of the stored code path data and/or timing data may involve performing similarity or dissimilarity analyses with respect to different marker/identifier sequences corresponding to respective code paths/code locations and quantifying differences accordingly. In some examples, processing of the identifiers may involve extracting execution time data between two locations for comparing timing data between baseline/expected code paths and observed code paths in order to assess the device status, code path classification/categorization, etc. In some examples, different weights may be assigned to the identifiers depending on the effect(s) of the corresponding code paths on various performance indicators (e.g., power consumption, therapy effectiveness/efficacy, general computational efficiency of the IMD, and the like). In some examples, the weighted identifiers may be analyzed using appropriate statistical techniques, AI/ML engines, etc., for purposes of additional embodiments of the present disclosure as will be set forth further below.

In some example embodiments, code paths determined to be optimal, acceptable or otherwise characterized as good paths with respect to various pieces of firmware code (e.g., based on the metrics obtained pursuant to analyses of associated markers, such as tracing and timing markers) may be developed during initial development and formal testing of the IMD device, as previously noted. For example, initial code paths and timings may be defined by the theoretical/intended operation of the device and then revised based on actual operating conditions encountered in normal as well as unexpected scenarios performed during formal testing (e.g., corner case scenarios). Once the code path metrics baselines are defined, they can be stored as arrays of unique identifiers for each subsystem or function in an example arrangement. It should be apparent that the memory space needed for such storage may depend on the granularity of code instrumentation (e.g., total number of tracing/timing markers). For instance, a 16-bit word can hold 256 markers for 256 subsystems each (i.e., 65,536 unique combinations). If the markers are only used at the individual subsystem level, then the storage requirement may be reduced to an 8-bit byte for the same granularity of coverage in an example implementation.

In an example arrangement, timing metrics baselines may be stored as threshold windows comprising a high threshold (e.g., operative as a ceiling) and a low threshold (operative as a floor) of the allowed range with respect to a particular inter-event interval of a given subsystem. As set forth previously, multiple inter-event intervals may be monitored with respect to a subsystem based on its codebase instrumentation. Depending on implementation, the memory or timing buffer size may generally depend on the resolution of the timer used. In one arrangement, a code path metrics analytics module may be configured to check an actual timing measurement against the baseline threshold window for diagnostics and code path assessment. Because the baseline data and the actual measurements are both measured by the same onboard timer(s), the timing data can be compared in processor-friendly timer counts and therefore do not need to be converted to actual time units (e.g., microseconds, etc.) in some embodiments. Accordingly, storage of timing data in processor counts, cycle counts, etc., may be advantageously utilized in an example embodiment for reducing the storage/buffer space and processing time necessary to perform the described functionality.

With reference to quantification of the code path metrics data, various techniques and methodologies may be provided depending on implementation. In some arrangements, once an actual and expected path/patterns are compared based on the metrics data, suitable comparison results and associated statistics may be determined or otherwise obtained, which can be quantified by various means depending on the type of metrics. For instance, with respect to tracing, the number of different markers between the actual and expected paths/patterns may be used as a quality metric.

In additional and/or alternative embodiments, each individual path or function and/or associated markers may be given a weighting of how undesirable and/or likely that the path should be executed. In an example implementation, each code identifier/marker may be accorded a weight (e.g., based on domain knowledge experts during a development phase and/or in the field based on adaptive learning or artificial intelligence (AI) systems, etc.). For each code path traversed, a cumulative weight may therefore be determined, which may be aggregated and/or averaged over a number of the occurrences/observations of the code path in a time period.

In similar fashion, firmware modules of different code paths may also be accorded appropriate weights, priorities, etc., which may be gathered and analyzed statistically for purposes of path categorization (e.g., establishing baseline paths) and classification of observed/measured paths (i.e., candidate paths), and the like with respect to the execution of a device function and/or associated subsystem(s) in some additional and/or alternative embodiments. In an example implementation, for example, the weights for each marker in a path may be summed across the full execution of a subsystem or path and/or associated function and compared to an overall threshold of response, which may be determined based on domain knowledge as set forth previously. Such arrangements may be advantageously configured to allow for the detection of rare but low impact excursions (which may be tolerated), while providing for a triggering mechanism that only trips a response limit if the excursions happen too fast within a configurable time window and/or in combination with other undesired paths. Examples of such embodiments will be set forth further below in reference to illustrative use case scenarios, e.g., excess power consumption in a subsystem operation, etc.

For timing metrics data, the actual delta in timer counts between the expected and the actual measurement may be used in an example embodiment to quantify the amount of error at a given time. In some additional and/or alternative arrangements, the delta time may also be integrated or aggregated over time and compared against a known good average value to determine if the overall behavior with respect to the subsystem or function is erratic in a statistically determinable way, thereby necessitating a suitably graduated response. Such example arrangements may be further configured to ignore rare excursions, which may be determined based on suitable statistical process control (SPC) or statistical quality control (SQC) charts, having appropriate control limits, etc.

In still further arrangements, depending on implementation, both types of code path metrics data (e.g., tracing data and timing data) may be used in combination (e.g., in some proportion) to provide further levels of code path categorization and discrimination in order that a system (e.g., either onboard an IMD or off-board at a network node, or a combination thereof) is more adaptive to identify device firmware subsystem issues, quantify their severity and execute a suitable graduated response protocol. On the other hand, some example embodiments may be configured to use the metrics data separately, especially where code complexity, resource utilization and the instrumentation overhead issues may be relevant.

Because some example embodiments may be configured to provide quantified metrics data that may be utilized in obtaining an error value (e.g., in a static analysis configuration), the error values can be either compared against a fixed baseline value/range as described above, or they can be input into an AI/ML-based modeling system (e.g., the bid data analytics platform 320 of FIG. 3) to adaptively predict the expected values relative to the particular usage, inputs, and environments of each individual user, as will be set forth further below. Once the values for a given subsystem are measured, various characteristics such as notable results, failures, near-misses, or erratic behavior, etc., may be quantified and stored and sent to an external device or to a cloud server in order to process the results and perform the categorization and severity calculations for the IMD. It should be appreciated that whereas an external node implementation may lower the responsiveness, such an implementation may increase the processing capability, thereby allowing for subtler issues to be identified and/or require less computational resources onboard the IMD. Furthermore, such external node implementations may be configured so as to allow for more confidence to be developed in issue identification (e.g., in uncertain operational scenarios) prior to acting on them. In some arrangements where long-term impacts on the device are considered (e.g., subtle therapy variations or drift issues, increased power usage, etc.) periodic code path verifications may be effectuated (e.g., daily, weekly, or monthly checks) according to examples herein. As will be seen further below, code path metrics data from multiple IMDs (and patients) may be aggregated in a network environment (e.g., digital healthcare network environment 360 shown in FIG. 3) in order to obtain or provide further levels of subtility and complexity to code path categorization and discrimination within an AI/ML-based Big Data analytics framework.

Alternatively, onboard processing may be provided within an IMD, where a code path metrics analytics module may be configured for purposes of some embodiments herein as noted previously. In such onboard arrangements, the code path metrics analytics module in the firmware of the IMD may be used categorize code paths, associated operational issues, etc., and assess their severity in real-time as the metrics are acquired. It should be appreciated that example onboard arrangements may be particularly advantageous in some deployments as they may increase the responsiveness of the response, which could be important for safety or timing critical issues. However, the advantages of such arrangements may need to be balanced against the cost of additional device power usage and hardware/software complexity.

In example embodiments of the present disclosure, unique identifiers (e.g., tracing and timing markers) may be provided with respect to one or more code locations of a subsystem's firmware as previously noted (e.g., codebase 1000 illustrated in FIG. 10). In an example implementation, the capability to track the firmware's unique identifiers may be built into the firmware itself. For instance, there may be a separate code portion in the firmware (e.g., similar in functionality to the logging module 908 illustrated in FIG. 9) that may be configured to extract and store the identifiers in a memory buffer (e.g., according to a sequential order), which may be processed and analyzed for facilitating appropriate action including alarm notifications, graduated responses, etc., depending on implementation and the functionality of the subsystem. In some arrangements, a function call configured to pass control to a logging function may be executed at the instrumented code locations for storing the respective identifiers (possibly with a time stamp) during the execution of a code path of the firmware as the corresponding code locations are traversed. For example, an extracted identifier sequence corresponding to a code path of the firmware may comprise a sequence [Id1, Id3, Id5, Id9], whereas an extracted identifier sequence corresponding to another code path of the firmware may comprise a sequence [Id1, Id2, Id4, Id7, Id9], which may be stored in the same memory buffer or in a different buffer. In some arrangements, the logging function may be provided as part of the subsystem's firmware, e.g., as a submodule, although other implementations (e.g., a centralized logger for multiple subsystems) are also within the scope of the present disclosure.

In some example arrangements, stored identifiers with respect to different code paths may be processed for generating respective code path metrics, which may be analyzed for modulating the behavior of the subsystem accordingly, as noted previously. In some representative embodiments, separate analysis code may be provided that may be configured to operate at a higher level in a software control hierarchy of the device. For example, the analysis code may be implemented as part of a code diagnostics portion (e.g., portion 908 set forth in FIG. 9) such that it has the capability of controlling the execution of the subsystem's firmware to effectuate a graduated response if needed.

With respect to providing graduated responses, some example embodiments may be further configured with additional functionality beyond identifying and quantifying an issue based on code path metrics. As noted previously, whereas existing solutions typically provide a reset response, it is often suboptimal in that it can be particularly excessive in relation to a more localized and/or less critical issue. Because the example embodiments herein are configured to utilize the quantified metrics based on more granularity as described above, which broadens a decision space with additional dimensions and ranges of outcomes for each potential scenario, a graduated response may be applied based on the results from the onboard and/or offboard code path metrics analytics. As such, granular analytics with respect to subsystem operations, performance, and functionality according to the embodiments herein provide a more adaptive and agile methodology to describe observed functional anomalies in addition to effectuating suitable adjustments to therapy mode(s), stimulation settings, and the like in a more dynamic manner.

Furthermore, because an example IMD may be configured to run through a control loop, most paths and timings may be traversed many times a day if not per second, where many repetitions can be aggregated in an example arrangement to reduce noise and build confidence in a conclusion or categorization decision according to the teachings herein. Some embodiments may therefore be configured with a database of one or more predefined lists of graduated responses that increase in severity or impact to the user as needed, where the database may be queried responsive to the inputs or outputs from a code path metrics analytics module.

By way of example, in one arrangement, a logging subsystem error may be identified and instead of impacting therapy output (e.g., while the device is in therapy mode), the device may be configured to re-initialize only the logging subsystem and restart it (e.g., in isolation as a separate process). If the re-initialization of the logging subsystem is determined to be unsuccessful, an escalated response may then be provided (e.g., a reset). In another variation, the logging subsystem issue may be flagged as an issue to be addressed the next time an authorized agent (e.g., the clinician, the patient, or a technician, etc.) interacts with the IMD. It will be appreciated that such a graduated response protocol is advantageous in that a full system reset, which is often resource-intensive, may be avoided for an issue that is not critical to device operation. Set forth below are some examples of graduated response generation scenarios, without limitation, that are illustrative of response modulation depending on the criticality of the subsystem (e.g., low vs. high), which highlight the customization possibilities with respect to each individual device and any subsystems thereof.

Case Scenario A: Low Criticality Subsystem (i.e., logging): perform the following steps in any ((pre)configured) order: (A1) Re-initialize the subsystem; (A2) Modify the mode of the subsystem; (A3) Disable the subsystem and flag for future troubleshooting; and (A4) Notify user to reset at a convenient time.

Case Scenario B: High Criticality Subsystem (i.e., therapy output): perform the following steps in any (preconfigured) order: (B1) Re-initialize the subsystem; (B2) Modify the mode of the subsystem; (B3) Reset the device; and (B4) Reprogram the subsystem.

As shown in the foregoing examples, responses are not merely limited to a full device reset and can be scaled up as needed depending on implementation and the type of subsystem involved. Further, the response options can go beyond resetting the device to even reprogramming a specific subsystem or a corresponding memory region. Additionally, because some example IMDs comprise healthcare devices regulated by governmental agencies, it is desirable for such devices to operate in a known good state in accordance with some implementations. Accordingly, additional and/or alternative embodiments herein may be configured to identify or establish a plurality of known good states that are verified and validated by the device developers and/or other stakeholders to be used as the operational bounds of a device (e.g., a safe operating area). By comparing the actual functional performance in the field against the baseline performance (which may be obtained in a development phase, or redefined in the field based on adaptive learning, for example), the device can be ensured to stay within that performance space. Additionally and/or alternatively, the device can be put in a known safe backup state if the device cannot be maintained within that performance space.

In still further examples, a device response may also include adjusting or modifying therapy being applied to a patient (e.g., therapy mode), which may include changing/updating different lead/electrode combinations used for therapy, stimulation parameters such as pulse amplitude, pulse width or duty cycle, pulse frequency or inter-pulse period, pulse repetition parameter, etc., as well as stimulation type, such as tonic stimulation, burst stimulation, noise-perturbed stimulation, high frequency stimulation, constant voltage or constant current stimulation, biphasic stimulation, monophasic stimulation, stimulation with or without discharge cycling, and the like.

Set forth below are example use case scenarios for illustrative purposes with respect to some aspects of the embodiments of the invention. It should be appreciated that the below examples are not intended to be an exhaustive list of the applications based on code path metrics.

In one example scenario, an excess power usage condition may be encountered while operating an IMD. By way of illustration, an IMD may be receiving continuous BLE connection requests from an external device, which cause the device to wake up often and incur the high-power usage of the onboard BLE subsystem to receive and transmit responses to the connection requests. In one example embodiment, a combination of timing and tracing metrics data may be utilized, whereby the code path analytics module of the device can identify that BLE connections are happening too often by either summing the weighted path of the high power BLE paths or by aggregating the short and repeated connection request intervals, as will be described in an example code path execution scenario set forth further below. In either situation, a flag may be tripped based on a threshold value, which can cause the subsystem to react. Because the excess power usage condition is due the interaction with an external device, a graduated response protocol may involve, without limitation: (i) temporary disablement of the BLE subsystem, and/or (ii) filtering out the external device from the list of allowable external devices for communication provided with the IMD. Skilled artisans will recognize that the embodiments herein identify and characterize the power overconsumption issue appropriately and provide response options that can address the power overconsumption issue and save power while maintaining the device deployment in the field. In contrast, a conventional system would identify the issue as a device that uses higher power than expected, thereby leading to customer service calls and possible replacement of the device as being "defective".

In another example scenario, a device therapy program changes its output based on an unexpected code path being traversed or encountering an issue with the device driver, thereby leading to a change in the output settings. Such changes can lead to unintended therapy settings, loss of therapy, and/or exceeding an allowable threshold such as charge balance. According to one example embodiment, code path tracing may be employed for debugging, whereby the system identifies that a program memory access occurs in a prohibited/restricted memory location(s). After identification, a flag may be set up for the memory to be recovered. In another embodiment, timing metrics may be utilized by the device for measuring the therapy output timing (e.g., frequency, pulse width, etc.), which may be compared to the expected/baseline settings. Responsive to detecting a difference and identifying that the therapy output setting is incorrect or violates a delta threshold, an example code path metrics analytics module of the device may notify the user of the issue and/or change the programming to what was intended. On the other hand, a conventional system would not be able to detect the incorrect output, thereby leading a patient/clinician to possibly misidentify the issue as insufficient therapy and/or needing a device replacement.

In yet another example scenario, an IMD device having patient posture feedback functionality may misinterpret input noise as postural changes, causing the device to adjust therapy inappropriately. In an example embodiment involving AI/ML modeling, the IMD device may be configured to learn, among others, the expected timing between postural adjustments for a user. This data may then be used to adjust the threshold for properly categorizing inputs as being due to a postural change distinguished from noise. Accordingly, the new threshold settings may allow the device to avoid changing the output therapy inappropriately. In conventional systems, the device has fixed thresholds and no adaptive metrics for modifying the functionality of the device in a customizable manner. As a consequence, the conventional device would continue to react in an inconsistent manner depending on what appears as noise on one patient versus as valid input on another patient, thereby providing incorrect and/or insufficient therapies to different patients.

Additional details with respect to foregoing example scenarios and embodiments of the present disclosure, including some representative methods and AI/ML-based modeling schemes, will be set forth below.

Figure 13:
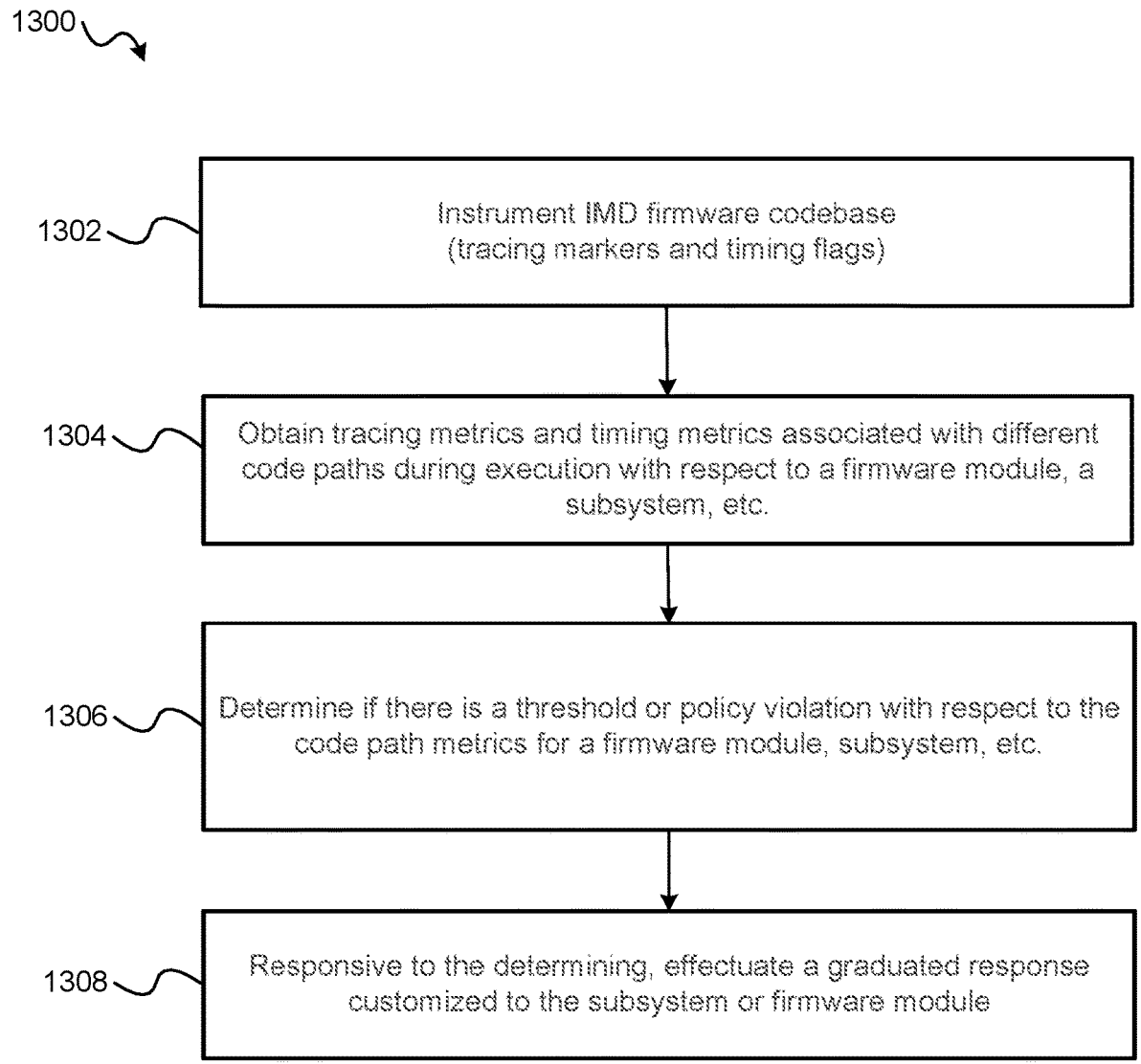
FIGS. 13-16 are flowcharts relating to some example methods of the present disclosure wherein the acts, blocks, functions and/or steps of a flowchart may (re)combined in one or more arrangements with or without other flowcharts for purposes of effectuating and managing IMD functions or subsystems based on code path metrics.

FIGS. 13-16 are flowcharts relating to one or more methods of the present disclosure wherein the acts, blocks, functions and/or steps of a flowchart may be (re)combined in one or more arrangements with or without other flowcharts for purposes of effectuating and managing IMD firmware modules or subsystems based on code flow metrics. Example process 1300 shown in FIG. 13 is illustrative of an instrumentation-based device state characterization scheme with respect to an A/IMD according to some embodiments herein. At block 1302, process 1300 may commence with instrumenting the IMD firmware codebase, which may include one or more firmware modules. Suitable tracing markers/identifiers and/or timing flags may be created or defined for specific points or code locations as described previously.

At block 1304, various tracing metrics and timing metrics associated with different code paths may be obtained with respect to a firmware module, a subsystem, etc. (e.g., during execution of firmware instructions). At block 1306, a determination may be made if there is a threshold or policy violation with respect to the code path metrics for a firmware module, subsystem, etc. As noted elsewhere in the present disclosure, the thresholds, policies, etc., may depend on the IMD mode, type and criticality of the functional module, subsystem, etc. Responsive to the determining, a graduated response may be effectuated, which may also depend on the IMD mode, type and criticality of the firmware module, subsystem, severity of the issue, etc., which may be customized on a per firmware module or subsystem basis (block 1308). As previously noted, various therapy modes, stimulation settings, etc., may also be modified or adjusted as part of a graduated response by the IMD in some implementations. The graduated responses may further include limiting the functionality of the firmware module, and/or the subsystem, changing the operating mode of the firmware module and/or the subsystem, changing the metadata (e.g., operating parameters) for the firmware module, and/or the subsystem in a given mode, and the like.

Figure 14:
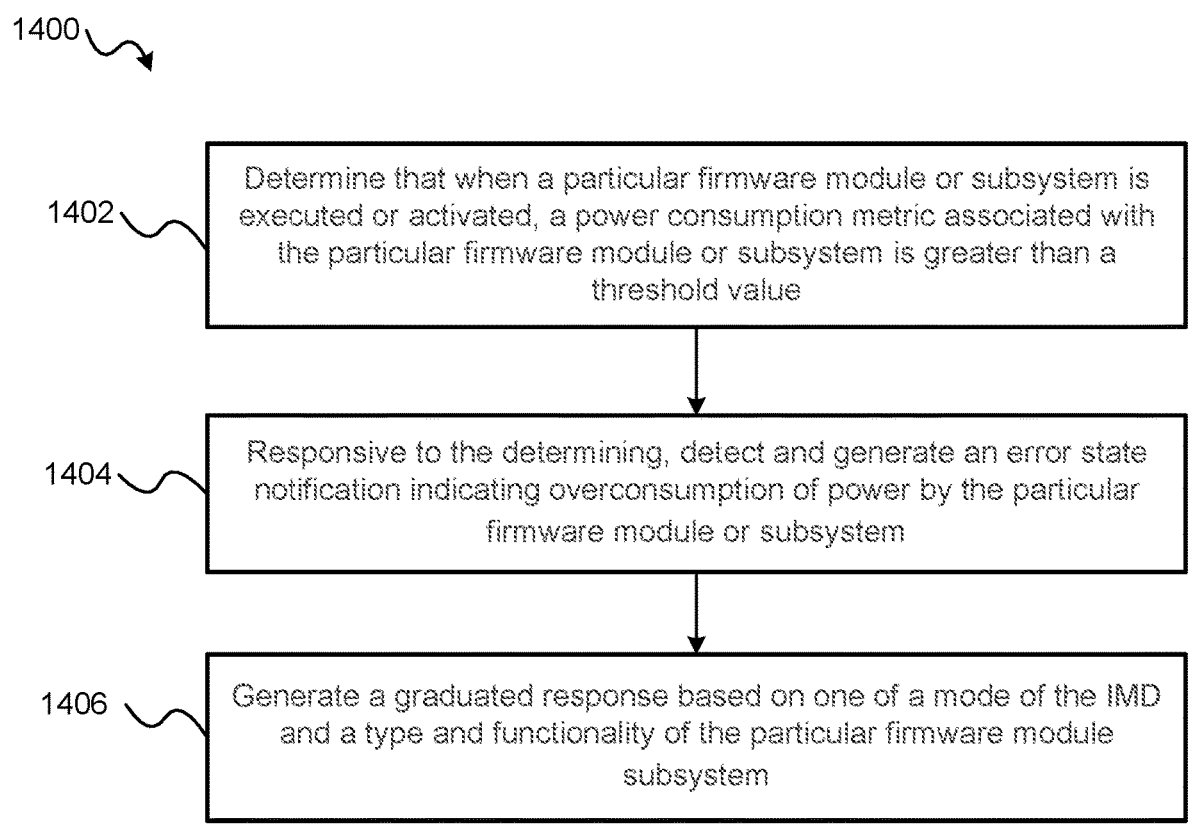

Example process 1400 shown in FIG. 14 includes operations for a consumption management scheme with respect to a firmware subsystem or firmware module of an IMD according to some embodiments herein. At block 1402, a determination may be made that when a particular firmware module or subsystem of the IMD is executed or activated, a power consumption metric corresponding to the particular firmware subsystem or module is greater than a threshold value. As described elsewhere in the present disclosure, an example power consumption metric may comprise a parameter or value derived from a plurality of weights associated with respective code paths that may be aggregated, wherein the weights represent the code path's impact on power (e.g., power consumption). In some examples, the power consumption metric may be determined based on respective code flow metrics associated with a plurality of code paths executed for effectuating or activating the particular firmware module or subsystem. In some arrangements, a power consumption metric may be determined based on a specific code path traversed. In further arrangements, a power consumption metric may be estimated or predicted based on the observed code path behavior (e.g., relative to expected or baseline code path behavior). Regardless of specific implementation, responsive to the determining, an error state may be detected and associated notification(s) may be generated (e.g., a code path metrics analytics module), indicating overconsumption of power by the particular firmware module or subsystem (block 1404). At block 1406, a graduated response (e.g., including therapy adjustments where appropriate) may be generated based on one of a mode of the IMD and a type and functionality of the particular firmware module or subsystem, which may be based on querying a preconfigured response database in some examples as noted above.

Figure 15:
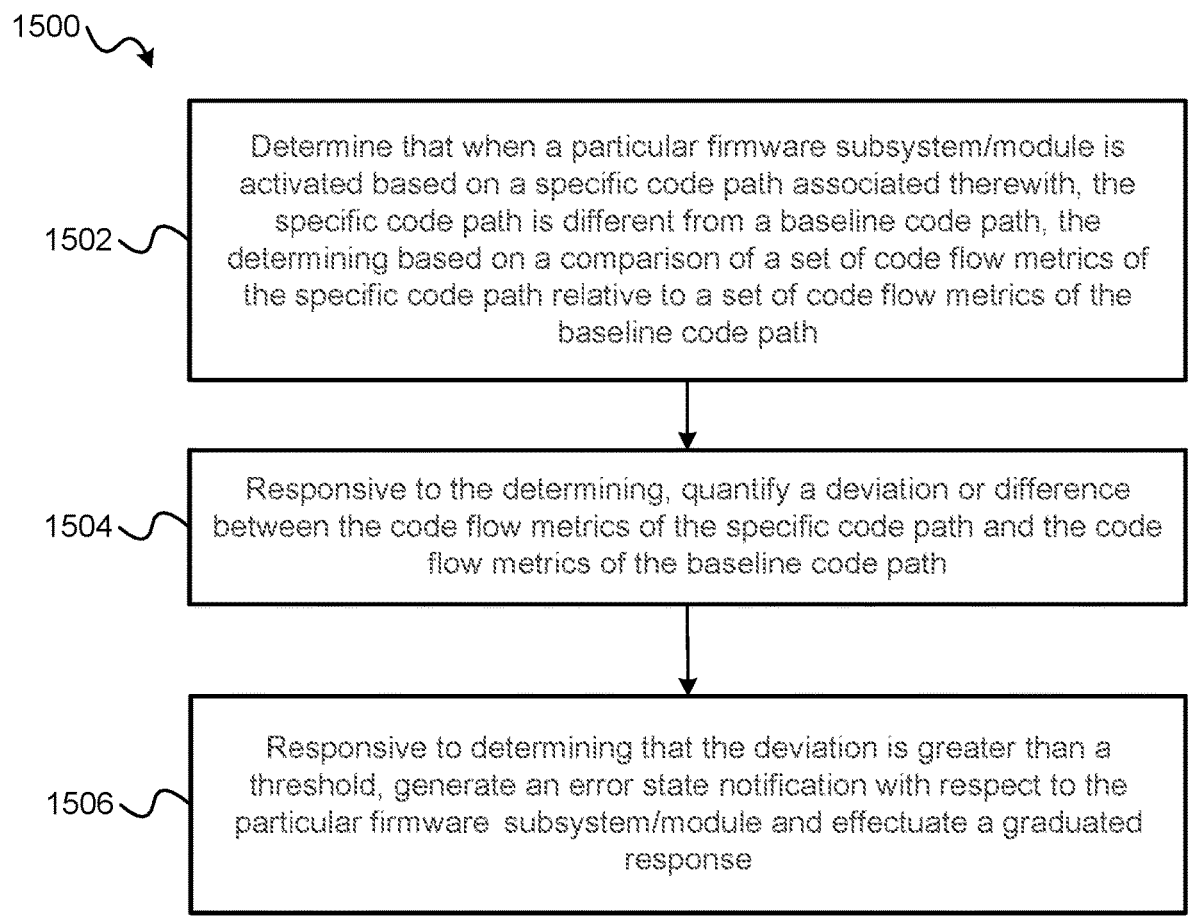

Example process 1500 shown in FIG. 15 is illustrative of a scheme for management of IMD operations based on deviations observed with respect to a baseline or expected code path of a firmware subsystem or module. At block 1502, a determination may be made that when a particular firmware subsystem/module is activated based on a specific code path associated therewith, the specific code path is different from a baseline code path. In an aspect, the determining may be based on a comparison of a set of code flow metrics of the specific code path relative to a set of code flow metrics of the baseline/expected code path. Responsive to the determining, a deviation or difference between the code flow metrics of the specific code path and the code flow metrics of the baseline code path may be obtained, quantified or otherwise determined (block 1504). Responsive to determining that the deviation is greater than a threshold, an error state may be detected and associated notification(s) may be generated with respect to the particular firmware subsystem/module (block 1506). Further, a graduated response may be generated based on one of a mode of the IMD and a type and functionality of the particular function or subsystem as previously noted.

Figure 16:
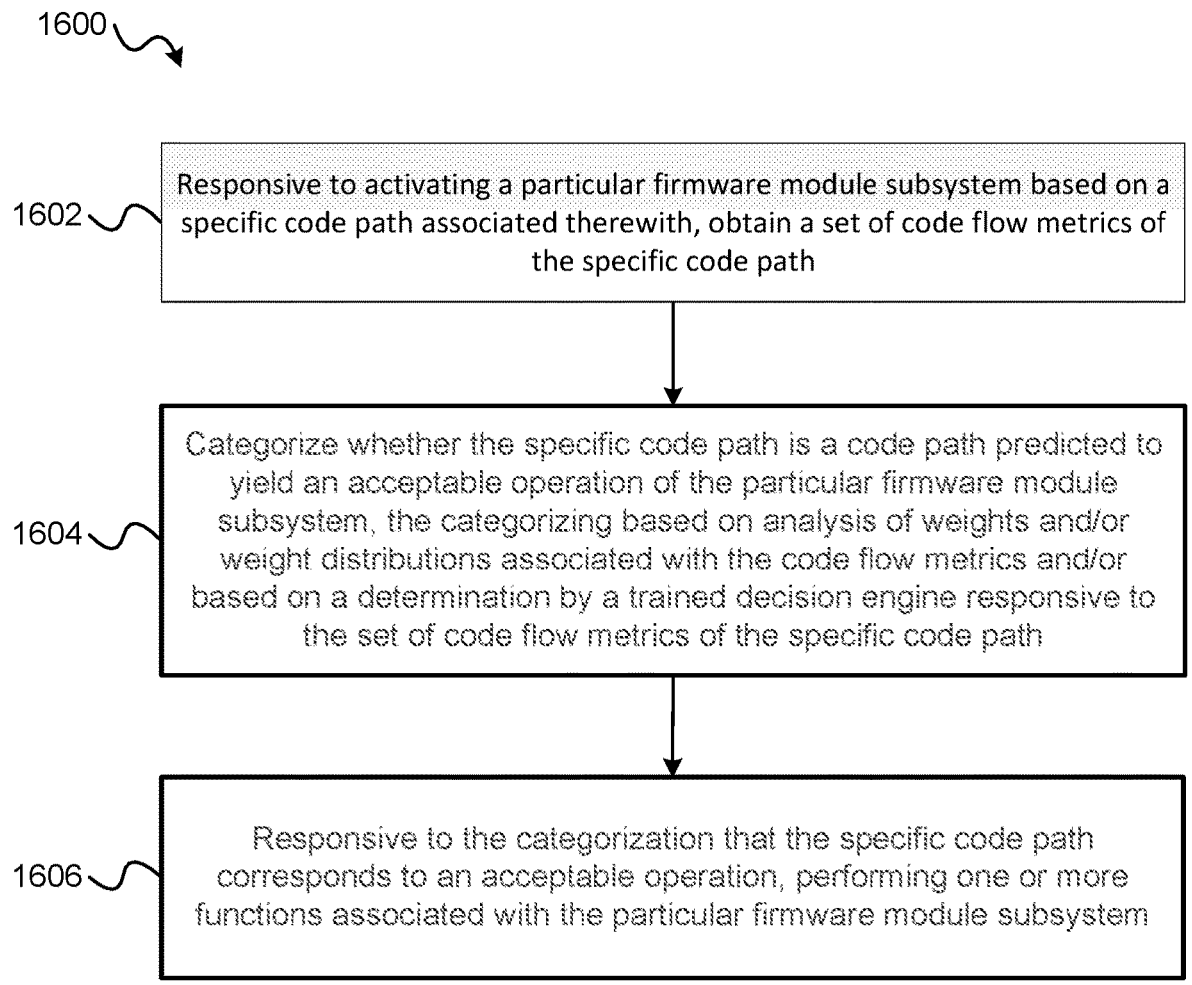

Example process 1600 shown in FIG. 16 is illustrative of a code path categorization scheme for managing IMD operations. Responsive to activating/accessing a particular firmware module or subsystem based on a specific code path associated therewith, example process 1600 is operative for obtaining a set of code flow metrics of the specific code path (block 1602). At block 1604, a categorization may be made as to whether the specific code path is a code path predicted to yield or correspond to an acceptable operation of the particular subsystem. In some arrangements, the categorization may be based on an analysis of the weights or weight distributions associated with the code flow metrics of the specific code path. In some additional and/or alternative arrangements, the categorization may be based on a determination by an AI/ML-based trained decision engine responsive to the set of code flow metrics of the specific code path, wherein the trained decision engine may be provided as part of the IMD. Depending on implementation, the trained decision engine may also be provided at a network node (e.g., as part of a device management system associated with a digital healthcare network), which may be based on training data obtained from a plurality of IMDs managed by the network. In some arrangements, the trained decision engine may be provided as part of an authorized external device such as, e.g., a patient controller device, a clinician programmer device, etc., as previously noted. Responsive to the categorization that the specific code path corresponds to an acceptable operation, one or more functions associated with the particular firmware module or subsystem may be performed (block 1606).

In some arrangements involving AI/ML-based decision-making, various pieces of code path metrics data, stimulation settings data, user input data, etc., may be stored in respective buffers and/or as part of a database that may be used as a labeled input dataset for training, validating and testing suitable AI/ML-based decision engines for performing or facilitating, inter alia, code path prediction, categorization of code paths or associated operations, error state detection and notification, graduated response generation, etc.

Figure 11:
FIG. 11 depicts an example database or storage structure including code path metrics data that may be provided as part of a training database for purposes of some embodiments of the present disclosure.

FIG. 11 depicts an example database or storage structure including code path metrics which may be provided as part of a training database for purposes of some embodiments of the present disclosure. Example database 1100 may include labeled records for each code path of codebase(s) corresponding to a firmware module, subsystem or a group of subsystems, where various pieces of patient/clinician input data, settings data, mode data, etc., collectively shown at reference numeral 1102, may be included in the individual records along with associated tracing metrics data 1106, timing metrics data 1108, performance/acceptability data 1110, etc., which may be cumulatively designated as code path metrics data 1104.

In some AI/ML methodologies of the present disclosure, at least a portion of such data may be broadly treated as attribute variables, wherein a suitable performance categorization variable (e.g., observed performance/categorization with respect to a particular code path) may be provided based on initial development, formal testing, trial deployment and/or in-patient settings. For example, an observed performance variable 1110 may comprise characterizing a code path or associated operation being acceptable or not acceptable. By way of illustration, data relating to code paths 1112-1 to 1112-N may be provided as an aggregated database that may include code path data across multiple firmware modules and/or subsystems in some arrangements as previously noted, although a module-by-module or subsystem-by-subsystem database may also be implemented in some implementations.

As an illustrative example, a record corresponding to Code Path-1 1112-1 may include stim set data as well as an ordered list of tracing markers [A1, A3, B4, C3, D3] that identifies various markers and associated codebase segments or modules traversed by the code path, and a timing data list corresponding to multiple inter-event windows or intervals (e.g., [TW1-1, TW1-2, . . . , TW1-N]) obtained responsive to a plurality of timing flags inserted in the codebase sequence(s), where the corresponding performance variable is observed or measured as "Acceptable". In similar fashion, a record corresponding to Code Path-3 1112-3 may include corresponding stim set data as well as an ordered list of tracing markers [A1, B3, A6, A7, C4, D6] that identifies various markers and associated codebase segments or modules traversed by the code path, and a timing data list corresponding to multiple inter-event windows (e.g., [TW3-1, TW3-2, . . . , TW1-M]), where the corresponding performance variable is identified as "Not Acceptable". As will be set forth below, some example embodiments involving AI/ML-based adaptive-predictive modeling may use at least a portion of a labeled database associated with a single IMD or collected respectively from a plurality of IMDs for training, validation and testing purposes.

In some example implementations, the code path metrics may be provided with different weights as noted previously, where the respective weights or weight distributions associated with the markers of a code path may be used in categorizing or classifying code paths based on the observed performance of a path. Accordingly, weights [W1, . . . , Wn], [W1, . . . , Wk] and [W1, . . . , Wm] are illustrative of the corresponding weights associated with the trace marker sequences provided in records 1112-1, 1112-2 and 1112-3, respectively. Likewise, weights [W'1, . . . , W'n], [W'1, . . . , W'k] and [W'1, . . . , W'm] are illustrative of the corresponding weights associated with the timing interval sequences provided in records 1112-1, 1112-2 and 1112-3, respectively. In addition to the observed performance variables, the code paths may also be categorized as baseline paths depending on the weight distributions associated with the corresponding metrics, which may provide data for comparison with respect to a new code path (e.g., a candidate path) requiring classification, as noted previously.

Figure 17:
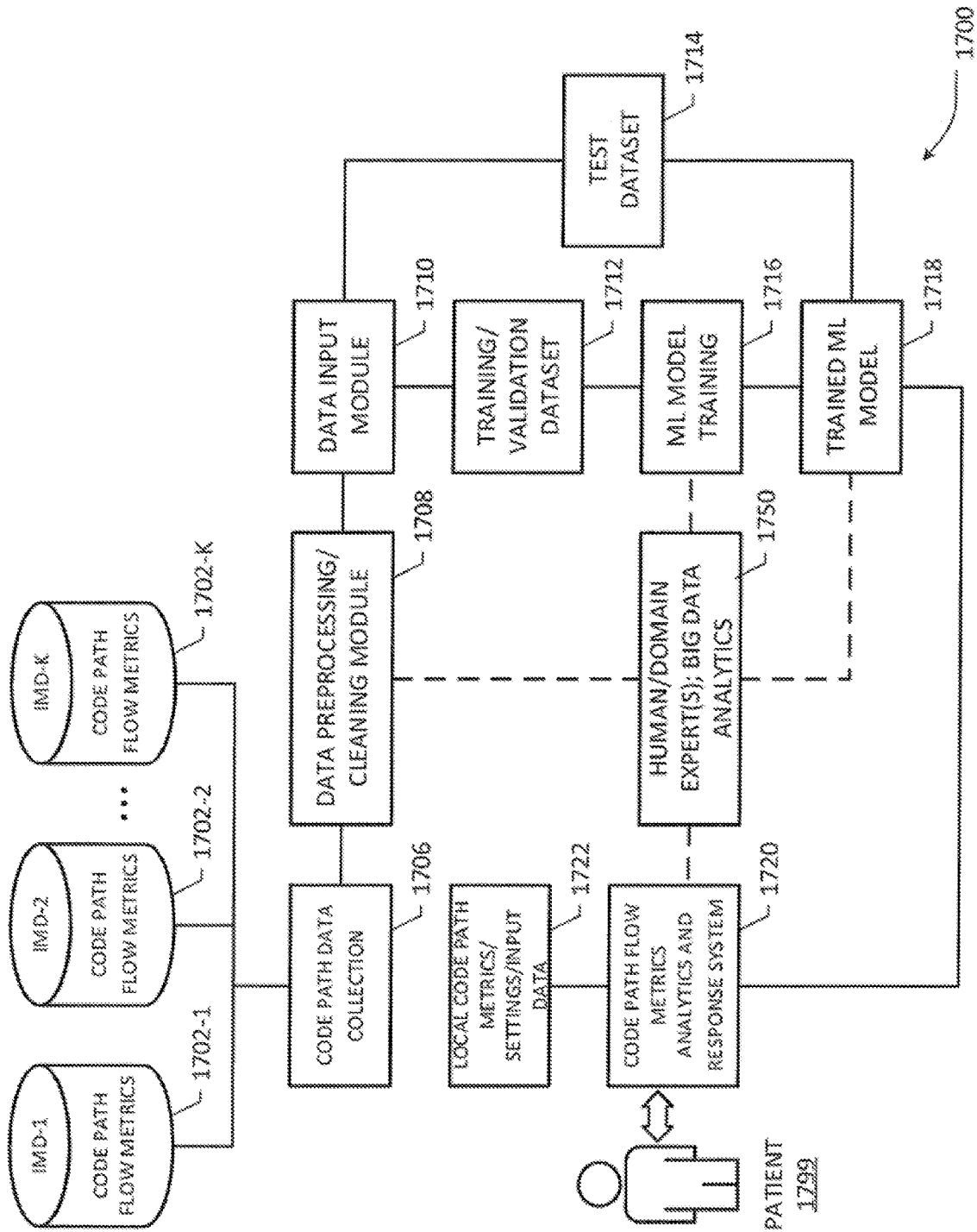
FIG. 17 depicts a scheme relating to a machine learning (ML)-based code path decision engine for purposes of some representative embodiments of the present disclosure.

Turning attention to FIG. 17, depicted therein is a block diagram of an apparatus, node, or computing device or platform 1700 for training, testing and/or generating a validated/tested AI/ML-based code path decision engine (e.g., based on a neural network or other deep leaning techniques) for purposes of some representative embodiments. Where implemented as part of a digital healthcare network environment, a data collection module 1706 is operative to obtain code path flow metrics data from one or more IMDs (e.g., associated with multiple patients or a class of patients) in addition to other pieces of data, such as patient input data, stim settings data, patient posture and/or activity data, etc., where the data may be warehoused in one or more databases 1702-1 to 1702-K.

Alternatively, if the AI/ML-based functionality is provided as part of an IMD, appropriate code path flow metrics data and patient data may be locally stored in an onboard storage module (e.g., module 1722) that may include at least a portion of a labeled database, such as database 1100 of FIG. 11, comprising trace data and timing interval metrics as described above with respect to FIG. 11. A data preprocessing module 1708 is operative to perform data cleaning operations and/or data augmentation processes, as may be necessary, depending on how the raw data is collected, sensed, or otherwise acquired. In some arrangements, the data cleaning/augmentation processes may be guided, supervised, or semi-supervised by human and/or AI-based domain experts 1750 during formal testing and development phases of the IMD as well as in the deployment stage of the IMD with respect to a patient 1799. Accordingly, a modified input dataset may be generated by the data preprocessing/cleaning module 1708, which may be partitioned by an input module 1710 as one or more training datasets, validation datasets and/or test datasets. For purposes of some embodiments herein, a training dataset may be a dataset of code path metrics data (processed, preprocessed or unprocessed) used during the learning process of an ML-based model for fitting the parameters of the ML-based model. In an aspect, the training dataset may include code path metrics and the reprocessing may involve generating code path metrics based on the code path data. A training dataset including such code path metrics may be utilized to train the AI model in accordance with the concepts described herein. Preprocessing may also include other types of operations, such as normalization of data, identification and removal (or correction) of invalid or incomplete data, labelling of data, and the like.

A validation dataset is a dataset that may be used to tune hyperparameters (i.e., the architecture) of a classifier scheme comprising the fitted model. In some arrangements, a test dataset is a dataset that may be independent of the training dataset but follows the same probability distribution as the training dataset depending on implementation. By way of illustration, a training/validation dataset 1712 is exemplified as a labeled dataset that may be provided to a training process 1716 with respect to training and validating an ML-based classifier scheme for predicting acceptability (e.g., performance) of test code paths, correct/incorrect operations, configuring or reconfiguring baseline paths and threshold ranges of the code path metrics, etc., that may be obtained at various stages of the device life cycle.

Depending on the particular ML implementation architecture, ML model training 1716 may involve one or more iterations, which in some instances may include (semi) supervised learning based on input from human/AI experts, such that a trained ML model 1718 that is appropriately fitted is obtained (i.e., resulting in a model without underfitting or overfitting). In one embodiment, the foregoing operations may be provided as part of the ML training stage or aspect of an example implementation. In a subsequent or separate phase, the fitted/trained ML model 1718 may be used in conjunction with additional or partitioned input datasets 1714 as test data (e.g., corresponding to or gathered from actual/specific code paths traversed for accessing a subsystem), whereby predictive output with respect to a performance variable may be generated. As one skilled in the art will recognize, at least a portion of the foregoing operations may be performed onboard, off-board, online, offline and/or by different computing modules of a distributed computing platform depending on implementation.

After training, validating and testing the ML model 1718, it may be executed in conjunction with a suitable code path metrics analytics module 1720, which may be onboard (e.g., module 113 shown in FIG. 1, or disposed at a device management network), for quantifying, maintaining and modulating the functional status of an IMD in addition to generating suitable error status notifications and graduated response protocol messages as described above. Further, as part of an adaptive/predictive modeling scheme, part of the data input into training and validating the ML model 1718 may also include error feedback data (e.g., deviations from baseline paths, misclassifying observed code paths, differences between expected/baseline paths and observed code paths, etc.) for adaptively redefining the fitted parameters of the ML model 1718, whereby baseline paths as well as applicable thresholds may be further (re)defined continually on an ongoing basis.

Figure 18:
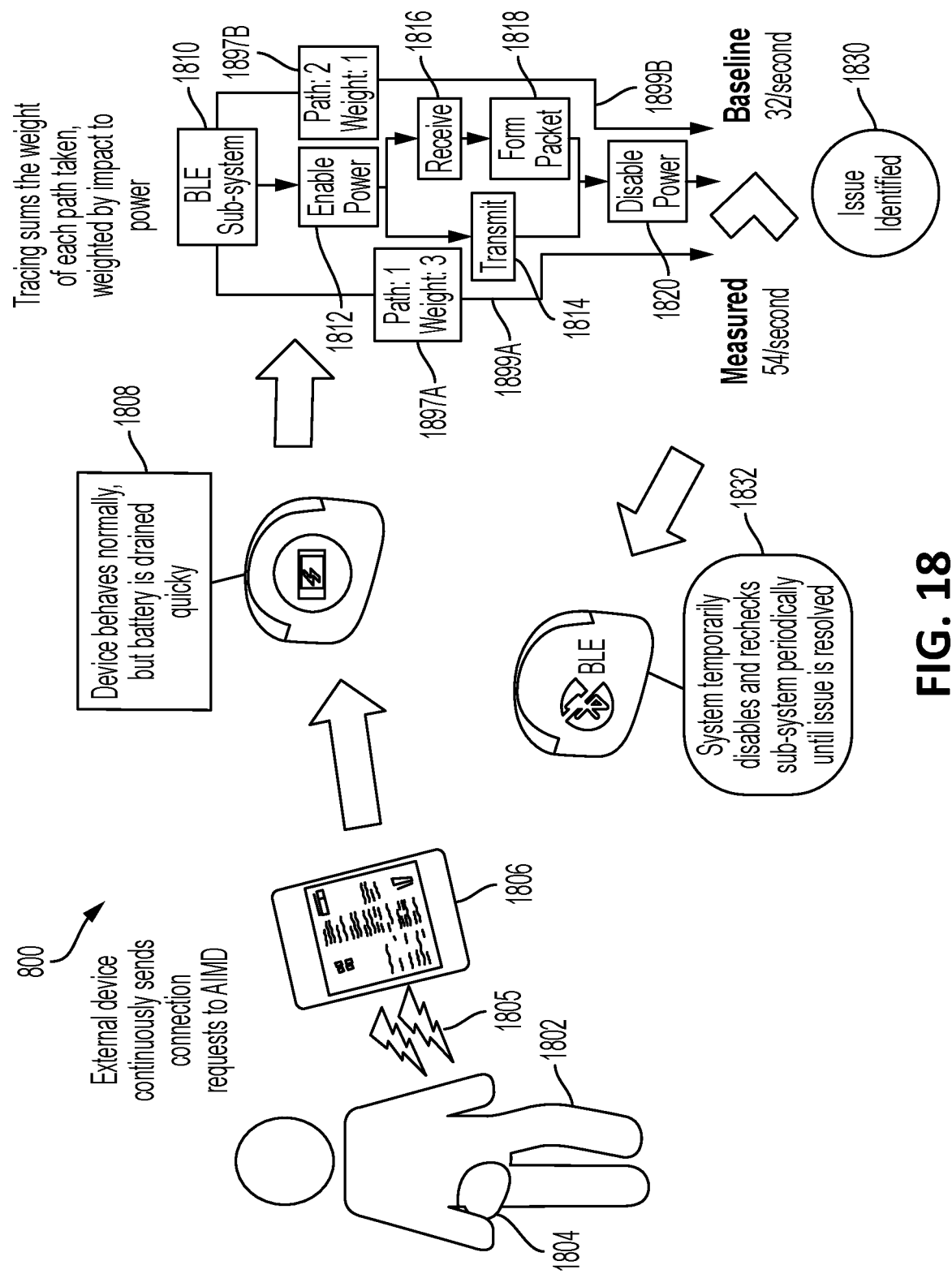
FIG. 18 depicts an IMD power consumption management scheme based on code path metrics according to some examples of the present disclosure.

FIG. 18 depicts an IMD power consumption management scheme 1800 based on code flow metrics according to some representative embodiments. As noted above with reference to an example use case scenario, an external device 1806, e.g., a patient controller device associated with patient 1802 or a clinician (not specifically shown in this FIG.), may be generating BLE connection requests 1805 to an IMD 1804, which can cause power drain on the device. As exemplified at block 1808, the device may continue to behave normally, although the battery may be drained quickly (e.g., relative to a baseline battery drain relationship over a period of time). Responsive to the connection request(s) 1805, a BLE subsystem 1810 may run different code paths traversing through various codebase sections configured to effectuate corresponding tasks, wherein the corresponding tracing metrics may be weighted differently depending on respective impacts on power consumption, e.g., as exemplified by path weights 1897A, 1897B.

By way of illustration, Enable Power module 1812, Transmit module 1814, Receive module 1816, Form Packets module 1818 and Disable Power module 1820 are exemplified, wherein one code path 1899A (or one set of code paths) may have a trace comprising markers associated with modules 1812, 1814 and 1820, the path 1899A having a total weight of 3 as exemplified by block 1897A. Likewise, another code path (or set of paths) 1899B may have a trace comprising markers associated with modules 1812, 1816, 1818 and 1820, that may be designated, categorized, defined or otherwise treated as a baseline set having a power impact weight of 1 as exemplified by block 1897B, which may be established in a device development phase and/or in the field.

In one arrangement, a tracing quantification process may be configured to sum the power impact weights of each path taken and averaged over a configurable amount of time or a number of connection requests. Where the power impact parameter (also referred to as a power consumption metric) of an actual path or an averaged value over a number of actual paths is greater than a baseline power impact metric (or where an actual path belongs to the path set having a measured power impact parameter greater than a threshold), a potential power overconsumption flag 1830 may be triggered.

By way of illustration, an aggregate sum of power impact weights of 54 obtained for a plurality of measured connection requests over one second is shown as greater than a baseline threshold of 32 per second, which may be deemed indicative of an overconsumption status. In some arrangements, both paths 1899A and 1899B may be executed over a designated time period, from which respective cumulative weights may be determined and compared. Accordingly, a graduated response protocol 1832 may be effectuated in response to the overconsumption flag 1830, in addition to generating appropriate status notifications and messages to a plurality of entities, e.g., the patient 1802, clinician, or a remote device management node, etc.

It should be appreciated that although the foregoing power consumption scenario is specifically set forth with respect to BLE communications, appropriate power consumption metrics may also be monitored relative to various subsystems/functionalities of an IMD based on respective code path metrics for generating suitable response protocols in a similar manner, including graduated responses and/or therapy adjustments as previously noted.

Figure 19:
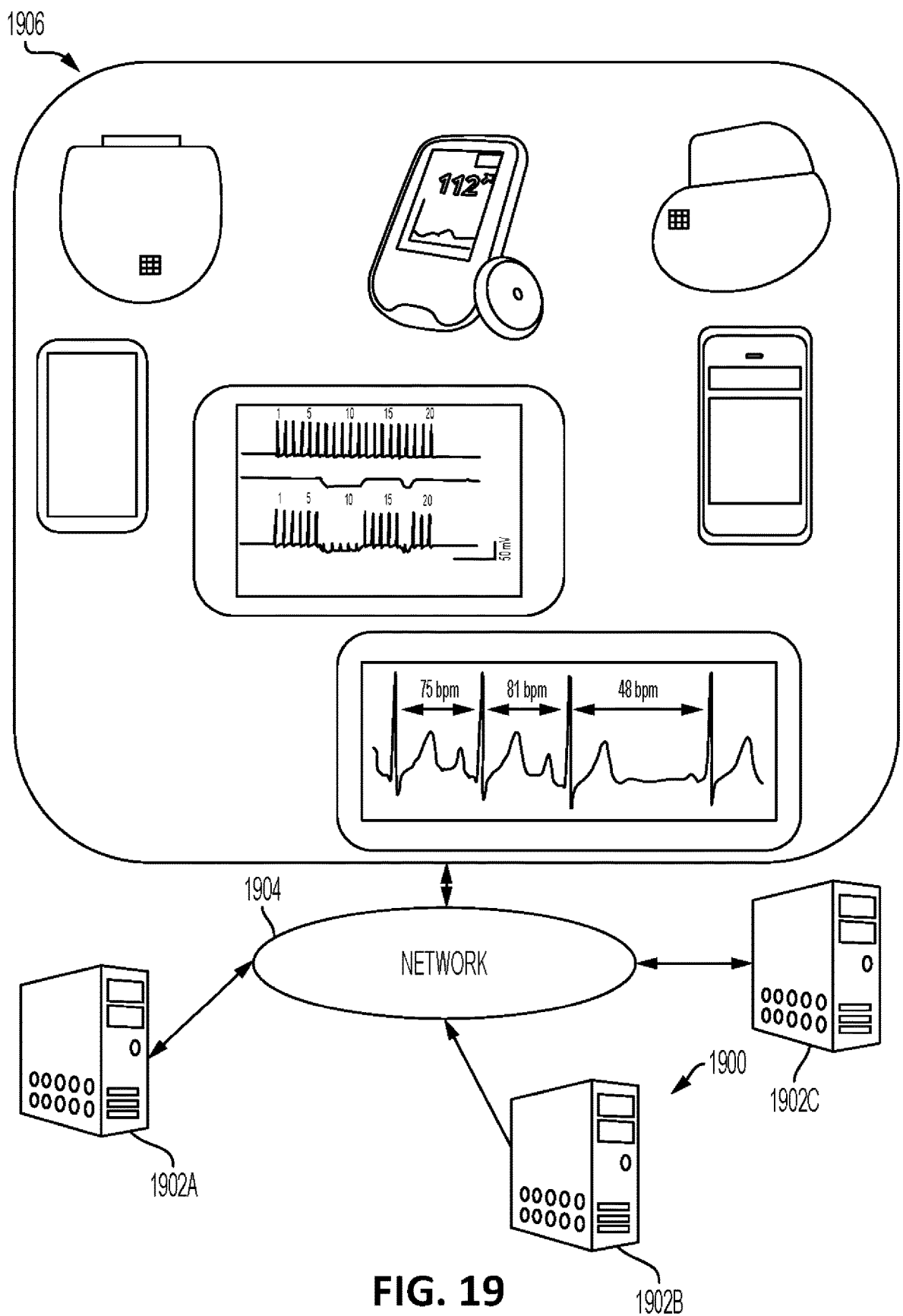
FIG. 19 depicts medical devices managed by a medical device management system that may be deployed as part of a healthcare network environment shown in FIG. 3 wherein code path metrics may be utilized for effectuating graduated responses in managing an IMD operation according to some examples of the present disclosure.

FIG. 19 depicts a plurality of medical devices 1906 managed by a medical device management system 1900 that may be deployed as part of a digital healthcare network environment shown in FIG. 3 wherein code flow data and/or metrics may be utilized. Example medical device management system 1900 may include a plurality of computer systems, servers, or platforms 1902A-1902C connected to network 1904 for management of devices 1906. Medical devices 1906 may include any number of devices and types of devices including neurostimulation devices, cardiac rhythm management devices, glucose monitoring devices, and medical agent infusion devices as examples. The devices may monitor and communicate patient data including code path data and/or metrics, etc. for communication to one or more server platforms 1902A-1902C. Depending on implementation, the patient data may also include any relevant physiological data such as cardiac activity, respiration data, glucose levels, neurological activity, physical activity data, posture data, and/or the like.

Figure 20:
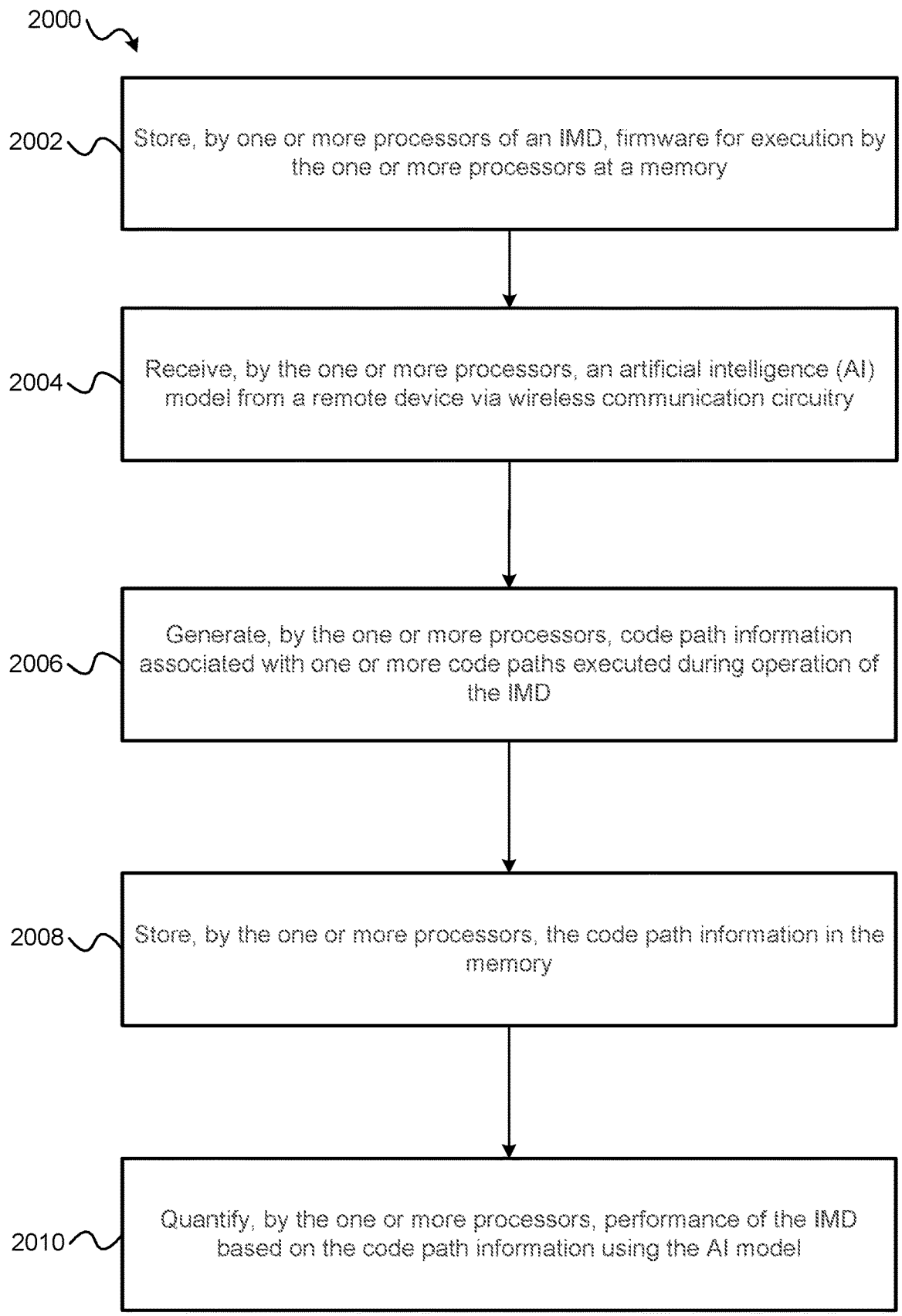
FIG. 20 is a flow diagram of an exemplary method for quantifying performance of an IMD in accordance with aspects of the present disclosure.

Referring to FIG. 20, a flow diagram of an exemplary method for quantifying performance of an IMD in accordance with aspects of the present disclosure is shown as a method 2000. In an aspect, the method 2000 may be performed by an IMD. For example, instructions may be stored in a memory of the IMD that, when executed by one or more processors of the IMD, cause the IMD to perform operations of the method 2000.

At step 2002, the method 200 includes storing, by one or more processors of the IMD, firmware for execution by the one or more processors at a memory. As explained above, the firmware may include a plurality of firmware modules controlling one or more corresponding hardware components of the IMD configured to support respective IMD functions. As explained above, the firmware code instructions may include one or more identifiers or markers corresponding to execution of particular firmware code instructions, and wherein the code path information comprises at least one of the one or more identifiers or markers corresponding to the executed one or more code paths of the IMD. Each of the plurality of firmware modules may be associated with multiple code paths traversing respective firmware code instructions, as explained above with reference to FIGS. 6-8.

At step 2004, the method 2000 includes receiving, by the one or more processors, an AI model from a remote device via wireless communication circuitry. For example, the AI model may be received from the data analytics platform 320 of FIG. 3. In an aspect, In an aspect, wherein the wireless circuitry may be configured to support BLUETOOTH™ communication. As explained above, the AI model may be trained based on a training dataset that includes code paths, code path metrics, or both associated with IMDs corresponding to a population of patients. In an aspect, the code paths, the code path metrics, or both included the training dataset include sets of code paths, sets of code path metrics, or both corresponding to different therapy configurations for the population of patients. The training dataset may include other types of information as well, such as timing information, therapy settings information, information associated with detecting deviations from one or more baseline code paths, information identifying one or more stimulation programs of the IMD(s), information identifying one or more stimulation parameters, information identifying one or more IMD component states, other types of information described herein, or a combination thereof. As explained above, in some implementations the training of the AI model may be performed iteratively until a stop criterion is satisfied. The training of the AI model may be configured to identify one or more baseline or expected code paths, code path metrics, or a combination thereof for each of the plurality of firmware modules. One or more hyperparameters of the AI model may be modified during at least one iteration of the training of the AI model.

At step 2006, the method 200 includes generating, by the one or more processors, code path information associated with one or more code paths executed during operation of the IMD. At step 2008, the method 2000 includes storing, by the one or more processors, the code path information in the memory. In an aspect, the code path information may be generated as described above, such as by storing markers or identifiers associated with the executed code path in a memory. The code path information may generated based on the firmware code instructions and may indicate execution of code corresponding to one or more code paths of the plurality of code paths. In an aspect, the code path information may also include timing data or other types of information described herein and may be generated as described above.

At step 2010, the method 200 include quantifying, by the one or more processors, performance of the IMD based on the code path information using the AI model. In an aspect, quantifying the performance of the IMD may include determining whether the code path information indicates normal operations of the IMD or abnormal operations of the IMD. The quantifying may also include other types of information indicative of the performance of the IMD, as described elsewhere herein. It is noted that while step 2010 is described as including quantification of the performance of the IMD, other types of information may also be determined by the AI model. For the example, outputs of the AI model may be used to maintain and manage the functional status and/or therapy settings of an IMD, as explained above.

Although not shown in FIG. 20, the method 2000 may include transmitting, via the wireless circuitry, feedback data to an analytics platform (e.g., the data analytics platform 320 of FIG. 3) and the training dataset may be updated based on the feedback data. In an aspect, the feedback may include information associated with deviations from one or more baseline code paths, information indicating one or more observed code paths that were misclassified by the AI model, differences between expected or baseline code paths and observed code paths, information identifying one or more stimulation programs of the IMD, information identifying one or more stimulation parameters, information identifying one or more IMD component states, or a combination thereof, and wherein the training dataset is updated based on the feedback. In an aspect, the analytics platform may be configured to perform additional training and/or update the training dataset based on feedback received from a plurality of IMDs. The updated training dataset may be used to perform additional training of the AI model to produce an updated trained AI model that may be distributed to one or more IMDs for use in quantifying, maintaining, and managing the functional status and/or therapy settings of an IMD in accordance with the concepts described herein.

In an aspect, the method 2000 may include determining a graduated response based on the one or more code metrics quantifying the performance of the IMD. As explained above, the graduated response may include adjustments to one or more therapy modes of the IMD, adjustments to one or more stimulation settings of a therapy program configured for the IMD, rebooting a particular firmware module of the IMD, updating firmware of the IMD, or a combination thereof. In an aspect, the graduated response may be determined based on a sequence of responses stored in memory. It is noted that while exemplary operations have been described with reference to the method 2000, it is to be understood that the method 200 may include other operations described herein for maintaining and managing the functional status and/or therapy settings of an IMD using any of the techniques and processes described herein.

It is noted that while FIG. 20 is described with reference to operations performed using an AI model local to an IMD, it is to be appreciated that other implementations are disclosed herein and may utilize similar processes. For example, the AI model may be maintained at a data analytics platform (e.g., the data analytics platform 320 of FIG. 3) and information associated with code paths of an IMD may be provided to the data analytics platform for analysis using the AI model. Graduated responses determined based on analysis of the IMD data using the AI model may then be communicated to the IMD to maintain and manage the IMD functional status and/or therapy settings. Similarly, the data analytics platform may periodically receive feedback from one or more IMDs and may update the AI model based on the received feedback. The updated AI models may then be distributed to one or more IMDs via one or more network communication links to provide updated AI models providing improved functionality and/or accuracy with respect to quantifying, maintaining, and/or managing the functional status and/or therapy settings of an IMD.

In one or more aspects, techniques for implantable medical devices configured to operate and/or provide therapy or medical diagnostic operations are described herein. In some examples, the techniques one or more aspects may be implemented in a method or process. In some other examples, the techniques of one or more aspects may be implemented in a device, such as an implantable medical device. In some examples, the implantable medical device may include at least one processing unit or system (which may include an application processor, a modem or other components) and at least one memory device coupled to the processing unit. The processing unit or system may be configured to perform operations, therapy, or medical diagnostic operations described herein with respect to the implantable medical device. In some examples, the memory device includes a non-transitory, computer-readable medium storing instructions or having program code stored thereon that, when executed by the processing unit or system, is configured to cause the implantable medical device to perform the operations described herein. Additionally, or alternatively, the implantable medical device may include one or more means configured to perform operations described herein.

Implementation examples are described in the following numbered clauses:

Clause 1: An implantable medical device (IMD) for implantation in a patient, comprising: one or more processors for controlling IMD operations; a battery for powering IMD operations; circuitry for controlling provision of a medical therapy to the patient or for conducting medical diagnostic operations; wireless communication circuitry for conducting communication with one or more devices external to the patient after implantation; and persistent memory for storing firmware for execution by the one or more processors, wherein the firmware includes a plurality of firmware modules controlling one or more corresponding hardware components of the IMD for respective IMD functions, and wherein multiple identified code paths traversing respective firmware code instructions are identified for each of the plurality of firmware modules; wherein the one or more processors, when executing firmware code for the plurality of firmware modules, are configured to: store identifiers corresponding to respective code paths of the multiple identified code paths in one or more memory buffers to indicate execution of code of each respective code path; process stored code path identifiers stored in the one or more buffers to generate respective code path metrics; calculate at least one power consumption metric using one or more respective calculated code path metrics; and reset at least one of the plurality of firmware modules upon determining that the power consumption metric indicates improper IMD operations.

Clause 2: The IMD of clause 1, wherein the at least one processor is further configured to calculate the at least one power consumption metric based on weights associated with one or more code paths of the identified code paths.

Clause 3: The IMD of clause 2, wherein the weights represent an impact of the one or more code paths on power consumption.

Clause 4: The IMD of clause 2, wherein the one or more processors are configured to aggregate information corresponding to one or more executed code paths of the identified code paths, wherein the at least one power consumption metric is calculated based at least in part on the aggregating.

Clause 5: The IMD of clause 1, wherein the at least one power consumption metric is calculated based on based on an observed code path behavior.

Clause 6: The IMD of clause 5, wherein the at least one power consumption metric comprises a difference between an expected or baseline code path and the observed code path behavior.

Clause 7: The IMD of clause 1, wherein the one or more processors are configured to generate a graduated response based on the calculated at least one power metric.

Clause 8: The IMD of clause 7, wherein the graduated response comprises a plurality of responses, and wherein the reset of the at least one of the plurality of firmware modules comprises one response of the plurality of responses.

Clause 9: The IMD of clause 7, wherein the graduated response is based on a plurality of responses, wherein the plurality of responses comprise a series of escalating responses, and wherein the series of escalating responses include a first response having a lower impact on resources of the IMD relative to a subsequent response in the series of escalating responses.

Clause 10: The IMD of clause 1, wherein the medical therapy comprises a therapy configured to treat pain of the patient, treat a movement disorder of the patient, treat a cardiac process of the patient, treat a respiratory process of the patient, treat a digestive process of the patient, or a combination thereof.

Clause 11: The IMD of clause 1, further comprising at least one sensor configured to sense signals associated with the patient, and wherein the at least one processor is configured to modify the medical therapy of the patient based at least in part on the signals sensed by the at least one sensor.

Clause 12: A method for quantifying, managing, and maintaining performance of an implantable medical device (IMD) providing a medical therapy to a patient, the method comprising: receiving, by at least one processor, code path information from the IMD, wherein the code path information comprises one or more identifiers corresponding to a code path executed by at least one firmware module of a plurality of firmware modules of the IMD to control one or more corresponding hardware components for respective IMD functions, and wherein multiple identified code paths traversing respective firmware code instructions are identified for each of the plurality of firmware modules; processing, by the at least one processor, the code path information to generate respective code path metrics; calculating, by the at least one processor, at least one power consumption metric using one or more respective calculated code path metrics; generating, by the at least one processor, instructions to reset at least one of the plurality of firmware modules upon determining that the power consumption metric indicates improper IMD operations; and transmitting, by the at least one processor, the instructions to the IMD via a wireless communication link.

Clause 13: The method of clause 12, wherein the at least one processor is further configured to calculate the at least one power consumption metrics based on weights associated with one or more code paths of the multiple identified code paths, and wherein the weights represent an impact of the one or more code paths on power consumption.

Clause 14: The method of clause 13, wherein the one or more processors are configured to aggregate information corresponding to one or more executed code paths of the multiple identified code paths, and wherein the at least one power consumption metric is calculated based at least in part on the aggregating.

Clause 15: The method of clause 12, wherein the at least one power consumption metric is calculated based on based on an observed code path behavior.

Clause 16: The method of clause 15, wherein the at least one power consumption metric comprises a difference between an expected or baseline code path and the observed code path behavior.

Clause 17: The method of clause 16, wherein the expected or baseline code path is determined using a trained artificial intelligence model.

Clause 18: The method of clause 12, wherein the one or more processors are configured to generate a graduated response based on the calculated at least one power metric, wherein the graduated response comprises a plurality of responses, and wherein the reset of the at least one of the plurality of firmware modules comprises one response of the plurality of responses.

Clause 19: The method of clause 18, wherein the plurality of responses comprise a series of escalating responses, and wherein the series of escalating responses include a first response having a lower impact on resources of the IMD relative to a subsequent response in the series of escalating responses.

Clause 20: The method of clause 12, wherein the medical therapy comprises a therapy configured to treat pain of the patient, treat a movement disorder of the patient, treat a cardiac process of the patient, treat a respiratory process of the patient, treat a digestive process of the patient, or a combination thereof.

Clause 21: The method of clause 12, wherein the code path information is received from the IMD with timing information, with sensor data captured by sensors of the IMD, or both, and wherein the one or more processors are configured to modify the medical therapy of the patient based at least in part on the timing information, the sensor data, or both.

Clause 22: An implantable pulse generator (IPG) for providing electrical pulses to neural tissue of a patient, the IPG comprising: at least one processor for controlling IPG operations; a battery for powering IPG operations; circuitry for generating electrical pulses to stimulate the neural tissue of the patient; wireless communication circuitry for conducting communication with one or more devices external to the patient after implantation; and persistent memory for storing firmware for execution by the at least one processor wherein the firmware includes a plurality of firmware modules for controlling corresponding subsystems of the IPG, each subsystem controlled by multiple identified code paths traversing firmware code for implementing each respective subsystem; wherein the at least one processor, when executing firmware code for the IPG subsystems, is configured to: receive code path information from the IMD, wherein the code path information comprises one or more identifiers corresponding to a code path executed by at least one firmware module of the plurality of firmware modules of the IMD to control one or more corresponding hardware components for respective IMD functions; process the code path information to generate respective code path metrics; calculate at least one power consumption metric using one or more respective calculated code path metrics; and generate instructions to reset at least one of the plurality of firmware modules upon determining that the power consumption metric indicates improper IMD operations.

Clause 23: The IPG of clause 22, wherein the at least one processor is further configured to calculate the at least one power consumption metrics based on weights associated with one or more code paths of the identified code paths, and wherein the weights represent an impact of the one or more code paths on power consumption.

Clause 24: The IPG of clause 23, wherein the one or more processors are configured to aggregate information corresponding to one or more executed code paths of the identified code paths, and wherein the at least one power consumption metric is calculated based at least in part on the aggregating.

Clause 25: The IPG of clause 22, wherein the at least one power consumption metric is calculated based on based on an observed code path behavior and comprises a difference between an expected or baseline code path and the observed code path behavior, wherein the expected or baseline code path is determined using a trained artificial intelligence model.

Clause 26: The IPG of clause 25, wherein the one or more processors are configured to generate a graduated response based on the calculated at least one power metric, wherein the graduated response comprises a plurality of responses, and wherein the reset of the at least one of the plurality of firmware modules comprises one response of the plurality of responses.

Clause 27: The IPG of clause 22, wherein the code path information is received with timing information, with sensor data captured by sensors, or both, and wherein the one or more processors are configured to modify a medical therapy of the patient based at least in part on the timing information, the sensor data, or both.

Clause 28: An implantable medical device (IMD) for implantation in a patient, comprising: one or more processors for controlling IMD operations; a battery for powering IMD operations; circuitry for controlling provision of a medical therapy to the patient or for conducting medical diagnostic operations; wireless communication circuitry for conducting communication with one or more devices external to the patient after implantation; and persistent memory for storing firmware for execution by the one or more processors, wherein the firmware includes a plurality of firmware modules controlling one or more corresponding hardware components of the IMD for respective IMD functions, and wherein multiple identified code paths traversing respective firmware code instructions are identified for each of the plurality of firmware modules; wherein the one or more processors, when executing firmware code for the plurality of firmware modules, are configured to: store identifiers corresponding to respective code paths of the multiple identified code paths in one or more memory buffers to indicate execution of code of each respective code path; process stored code path identifiers stored in the one or more buffers to generate respective code path metrics; calculate at least one power consumption metric using one or more respective calculated code path metrics; and generate a power overconsumption flag upon determining that the power consumption metric indicates improper IMD operations.

Clause 29: The IMD of clause 28, wherein the one or more processors are configured to analyze timing information stored in association with the code path identifiers during generation the code path metrics.

Clause 30: The IMD of clause 28, wherein the one or more processors are configured to generate a graduated response based on the calculated code path metrics, and wherein the graduated response comprises a plurality of responses that includes generating the power overconsumption flag.

Clause 31: The IMD of clause 30, wherein the graduated response comprises resetting a respective firmware module without interrupting executing of other firmware modules.

Clause 32: The IMD of clause 30, wherein the graduated response comprises resetting a respective hardware component of the IMD.

Clause 33: The IMD of clause 30, wherein the plurality of responses include performing a full system reset after performing at least one other response.

Clause 34: The IMD of clause 30, wherein the plurality of responses comprise modifying the medical therapy provided to the patient.

Clause 35: The IMD of clause 28, wherein the one or more processors are configured to determine a power impact of each code path taken by at least firmware module of the plurality of firmware modules over a period of time, and wherein the least one power consumption metric is determined based on the power impact of each code path taken by the at least one firmware module over the period of time.

Clause 36: The IMD of clause 35, wherein the least one power consumption metric is calculated based on an average power impact of code paths taken by the at least one firmware module over the period of time.

Clause 37: The IMD of clause 35, wherein the power consumption metric indicates improper IMD operations when the at least one power consumption metric is greater than a baseline power consumption metric.

Clause 38: The IMD of clause 37, wherein the IMD has different therapy modes, and wherein the baseline power consumption metric is different for at least a first therapy mode of the IMD and a second therapy mode of the IMD.

Clause 39: The IMD of clause 28, wherein the one or more processors are configured to store one or more timing flags, wherein the at least one power consumption metric is calculated based at least in part on the one or more timing flags.

Clause 40: A method for controlling an implantable medical device (IMD) for implantation in a patient, comprising: storing, in a persistent memory of the IMD, firmware for execution by one or more processors of the IMD, wherein the firmware includes a plurality of firmware modules controlling one or more corresponding hardware components of the IMD for respective IMD functions, and wherein multiple identified code paths traversing respective firmware code instructions are identified for each of the plurality of firmware modules; storing, by the one or more processors, code path identifiers when executing firmware code for the plurality of firmware modules, the identifiers corresponding to respective code paths of the multiple identified code paths in one or more memory buffers to indicate execution of code of each respective code path; processing, by the one or more processors, stored code path identifiers stored in the one or more buffers to generate respective code path metrics; calculating, by the one or more processors, at least one power consumption metric using one or more respective calculated code path metrics; and generate, by the one or more processors, a power overconsumption flag upon determining that the power consumption metric indicates improper IMD operations.

Clause 41: The method of clause 40, further comprising analyzing timing information stored in association with the code path identifiers during generation the code path metrics.

Clause 42: The method of clause 40, further comprising generating a graduated response based on the calculated code path metrics, wherein the graduated response comprises a plurality of responses, and wherein the plurality of responses includes generating the power overconsumption flag.

Clause 43: The method of clause 42, wherein the plurality of responses comprise performing a full system reset after performing at least one other response.

Clause 44: The method of clause 42, wherein the plurality of responses comprise modifying a medical therapy provided to the patient via the IMD.

Clause 45: The method of clause 40, further comprising determining a power impact of each code path taken by at least firmware module of the plurality of firmware modules over a period of time, wherein the least one power consumption metric is determined based on the power impact of each code path taken by the at least one firmware module over the period of time.

Clause 46: The method of clause 45, wherein the least one power consumption metric is calculated based on an average power impact of code paths taken by the at least one firmware module over the period of time.

Clause 47: The method of clause 45, wherein the power consumption metric indicates improper IMD operations when the at least one power consumption metric is greater than a baseline power consumption metric.

Clause 48: The method of clause 47, wherein the IMD has different therapy modes, and wherein the baseline power consumption metric is different for at least a first therapy mode of the IMD and a second therapy mode of the IMD.

Clause 49: The method of clause 48, further comprising storing one or more timing flags, wherein the at least one power consumption metric is calculated based at least in part on the one or more timing flags.

Clause 50: An implantable pulse generator (IPG) for providing electrical pulses to neural tissue of a patient, the IPG comprising: at least one processor for controlling IPG operations; a battery for powering the IPG operations; circuitry for generating electrical pulses to stimulate the neural tissue of the patient; wireless communication circuitry for conducting communication with one or more devices external to the patient after implantation; and persistent memory for storing firmware for execution by the at least one processor wherein the firmware includes a plurality of firmware modules for controlling corresponding subsystems of the IPG, each subsystem controlled by multiple identified code paths traversing firmware code for implementing each respective subsystem; wherein the at least one processor, when executing firmware code for the IPG subsystems, is configured to: store code path identifiers corresponding to respective code paths of the multiple identified code paths in one or more memory buffers to indicate execution of code of each respective code path; process stored code path identifiers stored in the one or more buffers to generate respective code path metrics; calculate at least one power consumption metric using one or more respective calculated code path metrics; and generate a power overconsumption flag upon determining that the power consumption metric indicates improper IMD operations.

Clause 51: The IPG of clause 50, wherein the at least one processor is configured to analyze timing information stored in association with the code path identifiers during generation the code path metrics.

Clause 52: The IPG of clause 50, wherein the at least one processor is configured to generate a graduated response based on the calculated code path metrics, wherein the graduated response comprises a plurality of responses, and wherein the plurality of responses includes generating the power overconsumption flag.

Clause 53: The IPG of clause 52, wherein the plurality of responses comprise performing a full system reset after performing at least one other response, modifying a medical therapy provided to the patient via the IPG, or both.

Clause 54: The IPG of clause 50, wherein the at least one processor is configured to determine a power impact of each code path taken by at least firmware module of the plurality of firmware modules over a period of time, wherein the least one power consumption metric is determined based on the power impact of each code path taken by the at least one firmware module over the period of time.

Clause 55: An implantable medical device (IMD) for implantation in a patient, comprising: one or more processors for controlling IMD operations; a battery for powering the IMD operations; circuitry for controlling provision of a medical therapy to the patient or for conducting medical diagnostic operations; wireless communication circuitry for conducting communication with one or more devices external to the patient after implantation; and persistent memory for storing firmware for execution by the one or more processors, wherein the firmware includes a plurality of firmware modules controlling one or more corresponding hardware components of the IMD for respective IMD functions and wherein multiple identified code paths traversing respective firmware code instructions are identified for each of the plurality of firmware modules; wherein the one or more processors, when executing firmware code for the IMD subsystems, are configured to: store an identifier corresponding to a respective code path of the multiple identified code paths in one or more memory buffers to indicate execution of code of the respective code path; calculate a deviation metric representing a difference between an observed firmware execution for a respective firmware module and baseline code execution defined for the respective firmware module; and responsive to determining that the deviation metric is greater than or equal to a threshold value, generate an error state notification with respect to the respective firmware module.

Clause 56: The IMD of clause 55, wherein the one or more processors are configured to generate a graduated response based on the deviation metric.

Clause 57: The IMD of clause 56, wherein the graduated response is selected from a plurality of pre-determined responses stored in the persistent memory of the IMD.

Clause 58: The IMD of clause 56, wherein the graduated response is generated based at least in part on a mode of the IMD, a type of functionality provided by the respective firmware module, or a combination thereof.

Clause 59: The IMD of clause 55, wherein the deviation metric is calculated using a trained artificial intelligence model.

Clause 60: The IMD of clause 55, wherein the deviation metric is calculated based on the stored identifiers.

Clause 61: The IMD of clause 55, wherein the deviation metric is calculated periodically according to a determined frequency.

Clause 62: The IMD of clause 61, wherein the frequency varies according to a function provided by the respective firmware module.

Clause 63: The IMD of clause 55, wherein the deviation metric is calculated prior to code path completion.

Clause 64: The IMD of clause 55, wherein the one or more processors are configured to provide the deviation metric to an external device as feedback.

Clause 65: The IMD of claim 64, wherein the external device comprises an analytics platform configured to train one or more artificial intelligence (AI) models using a training dataset, and wherein the training dataset is updated based on the feedback.

Clause 66: A system for managing an implantable medical device (IMD), the system comprising: a memory; and one or more processors communicatively coupled to the memory and configured to: receive an identifier corresponding to a respective code path of multiple identified code paths, each of the identified code paths corresponding to execution of one or more firmware modules a plurality of firmware modules of the IMD configured to control respective IMD functions for providing a therapy to a patient; calculate a deviation metric representing a difference between an observed firmware execution for a respective firmware module and baseline code execution defined for a firmware module of the one or more firmware modules corresponding to the respective code path; and responsive to determining that the deviation metric is greater than or equal to a threshold value, generate an error state notification with respect to the respective firmware module.

Clause 67: The system of clause 66, wherein the one or more processors are configured to generate a graduated response based on the deviation metric, wherein the graduated response is configured to modify operations of the IMD.

Clause 68: The system of clause 67, wherein the graduated response is selected from a plurality of pre-determined responses stored in the persistent memory of the IMD.

Clause 69: The system of clause 67, wherein the graduated response is generated based at least in part on a mode of the IMD, a type of functionality provided by the respective firmware module, or a combination thereof.

Clause 70: The system of clause 66, wherein the deviation metric is calculated using a trained artificial intelligence (AI) model.

Clause 71: The system of clause 70, wherein the one or more processors are configured to update a training dataset used to train the AI model based on at least the received identifier.

Clause 72: The system of clause 66, wherein the identifier is received from a device external to the IMD.

Clause 73: The system of clause 66, wherein the deviation metric is calculated periodically according to a determined frequency.

Clause 74: The system of clause 73, wherein the frequency varies according to a function provided by the respective firmware module.

Clause 75: The system of clause 66, wherein the deviation metric is calculated prior to code path completion.

Clause 76: The system of clause 66, wherein the therapy provided to the patient is modified based at least in part on the deviation metric.

Clause 77: A method for monitoring an implantable pulse generator (IPG) for delivering a medical therapy to a patient, the method comprising: storing, by one or more processors, firmware for execution by the one or more processors, wherein the firmware includes a plurality of firmware modules controlling one or more corresponding hardware components of the IPG for respective IPG functions and wherein multiple identified code paths traversing respective firmware code instructions are identified for each of the plurality of firmware modules; storing, by the one or more processors when executing firmware code for the IPG subsystems, an identifier corresponding to a respective code path of multiple identified code paths in one or more memory buffers to indicate execution of code of the respective code path; calculating, by the one or more processors, a deviation metric representing a difference between an observed firmware execution for a respective firmware module and baseline code execution defined for the respective firmware module; and responsive to determining that the deviation metric is greater than or equal to a threshold value, generating, by the one or more processors, an error state notification with respect to the respective firmware module.

Clause 78: The method of clause 77, wherein the one or more processors are configured to generate a graduated response based on the deviation metric, wherein the graduated response is selected from a plurality of pre-determined responses stored in the persistent memory of the IMD.

Clause 79: The method of clause 77, wherein the deviation metric is calculated using a trained artificial intelligence model.

Clause 80: The method of clause 77, wherein the one or more processors are configured to provide the deviation metric to an external device as feedback.

Clause 81: The method of clause 80, wherein the external device comprises an analytics platform configured to train one or more artificial intelligence (AI) models using a training dataset, and wherein the training dataset is updated based on the feedback.

Clause 82: A method for conducting diagnostic analysis of firmware code of an implantable medical device (IMD) of a patient, the method comprising: storing, by one or more processors of the IMD, firmware for execution by the one or more processors at a memory, wherein the firmware includes a plurality of firmware modules controlling one or more corresponding hardware components of the IMD configured to support respective IMD functions, and wherein each of the plurality of firmware modules is associated with multiple code paths traversing respective firmware code instructions; receiving, by the one or more processors, an artificial intelligence (AI) model from a remote device via wireless communication circuitry, wherein the AI model is trained based on a training dataset comprising code paths, code path metrics, or both associated with IMDs corresponding to a population of patients; generating, by the one or more processors, code path information associated with one or more code paths executed during operation of the IMD, wherein the code path information is generated based on the firmware code instructions and indicates execution of code corresponding to one or more code paths of the plurality of code paths; storing, by the one or more processors, the code path information in the memory; quantifying, by the one or more processors, performance of the IMD based on the code path information using the AI model.

Clause 83: The method of clause 82, wherein the code paths, the code path metrics, or both included in the training dataset include sets of code paths, sets of code path metrics, or both corresponding to different therapy configurations for the population of patients.

Clause 84: The method of clause 82, wherein the training of the AI model is performed iteratively until a stop criterion is satisfied.

Clause 85: The method of clause 84, wherein the training of the AI model is configured to identify one or more baseline or expected code paths, code path metrics, or a combination thereof for each of the plurality of firmware modules.

Clause 86: The method of clause 84, wherein one or more hyperparameters of the AI model are modified during at least one iteration of the training of the AI model.

Clause 87: The method of clause 82, further comprising transmitting, via the wireless circuitry, feedback data to an analytics platform, wherein the training dataset is updated based on the feedback data.

Clause 88: The method of clause 87, wherein the feedback comprises information associated with deviations from one or more baseline code paths, information indicating one or more observed code paths that were misclassified by the AI model, differences between expected or baseline code paths and observed code paths, information identifying one or more stimulation programs of the IMD, information identifying one or more stimulation parameters, information identifying one or more IMD component states, or a combination thereof, and wherein the training dataset is updated based on the feedback.

Clause 89: The method of clause 87, wherein the wireless circuitry is configured to support Bluetooth communication.

Clause 90: The method of clause 82, wherein performance of the IMD is quantified as one or more code metrics generated by the AI model, the method comprising: determining a graduated response based on the one or more code metrics quantifying the performance of the IMD.

Clause 91: The method of clause 90, wherein the graduated response comprises adjustments to one or more therapy modes of the IMD, adjustments to one or more stimulation settings of a therapy program configured for the IMD, rebooting a particular firmware module of the IMD, updating firmware of the IMD, or a combination thereof.

Clause 92: The method of clause 90, wherein the graduated response is determined based on a sequence of responses stored in memory.

Clause 93: The method of clause 82, wherein the firmware code instructions comprise one or more identifiers or markers corresponding to execution of particular firmware code instructions, and wherein the code path information comprises at least one of the one or more identifiers or markers corresponding to the executed one or more code paths of the IMD.

Clause 94: The method of clause 82, wherein quantifying the performance of the IMD comprises determining whether the code path information indicates normal operations of the IMD or abnormal operations of the IMD.

Clause 95: A method for conducting diagnostic analysis of firmware code of an implantable medical device (IMD) of a patient, the method comprising: training, by one or more processors, an AI model to quantify performance of an IMD using an artificial intelligence (AI) model to produce a trained AI model, wherein the training of the AI model is based on a training dataset comprising code paths, code path metrics, or both associated with IMDs corresponding to a population of patients; transmitting, by the one or more processors, the trained AI model to at least one IMD, wherein the at least one IMD comprises firmware for execution by one or more processors of the IMD, wherein the firmware of the IMD includes a plurality of firmware modules controlling one or more corresponding hardware components of the IMD configured to support respective IMD functions, and wherein each of the plurality of firmware modules is associated with multiple code paths traversing respective firmware code instructions; receiving, by the one or more processors, feedback from the at least one IMD, wherein the feedback comprises code path metrics generated based on execution of one or more code paths traversed during operations of the at least on IMD, information identifying one or more stimulation programs of the at least one IMD, information identifying one or more stimulation parameters of the one or more stimulation programs, information identifying one or more component states for the at least one IMD, or a combination thereof; updating, by the one or more processors, the trained AI model based on the feedback to produce an updated trained AI model; and transmitting, by the one or more processors, the updated trained AI model to the at least one IMD.

Clause 96: The method of clause 95, further comprising aggregating feedback received from a plurality of IMDs to produce an updated training dataset.

Clause 97: The method of clause 95, wherein the aggregating comprises determining one or more average values associated with the feedback, one or more maximum values associated with the feedback, one or more minimum values associated with the feedback, one or more mean values associated with the feedback, or a combination thereof.

Clause 98: The method of clause 95, wherein the AI model is trained over a plurality of iterations until a stop criterion is satisfied, and wherein hyperparameters of the AI model are tuned after at least one iteration of the plurality of iterations.

Clause 99: The method of clause 98, wherein the stop criterion comprises a threshold performance level of the AI model.

Clause 100: The method of clause 99, wherein the threshold performance level corresponds to an accuracy of the AI model with respect to quantifying the performance of an IMD.

Clause 101: The method of clause 95, wherein the IMDs corresponding to the population of patients are configured to provide different therapies to respective patients of the population of patients.

Clause 102: The method of clause 95, further comprising establishing one or more baseline or expected code paths during the training of the AI model.

Clause 103: The method of clause 95, further comprises determining one or more graduated responses for different outputs of the AI model, wherein the one or more graduated responses are updated periodically based on additional training of the A1 model.

Clause 104: The method of clause 103, wherein the one or more graduated responses comprise adjustments to one or more therapy modes of a particular IMD, adjustments to one or more stimulation settings of a therapy program configured for the particular IMD, rebooting a particular firmware module of the particular IMD, updating firmware of the particular IMD, or a combination thereof.

Clause 104: The method of clause 95, wherein the trained AI model comprises a classifier configured to classify one or more code paths observed at a particular IMD as normal or abnormal.

Clause 105: A method of controlling operations of implantable medical devices (IMDs) using an artificial intelligence (AI) model of IMD operation based on firmware code path execution in respective IMDs, comprising: receiving, by one or more servers for IMD management, code path data from a plurality of IMDs after implantation in respective patients, the code path data representing firmware code instructions executed by one or more firmware modules of a plurality of firmware modules corresponding to firmware executable by one or more processors of each of the plurality of IMDs to control corresponding hardware components of the IMDs for respective IMD functions, and wherein multiple identified code paths traversing respective firmware code instructions are identified for each of the plurality of firmware modules; training, using one or more servers, the AI model using the received code path data to generate a model of IMD operations representing proper operation of an IMD; distributing the trained AI model from one or more servers for IMD management to a set of IMDs; operating IMDs to perform IMD-diagnostic operations based on the distributed, trained AI model to control IMD operations.

Clause 106: The method of clause 105, wherein training the AI model using the received code path data to generate the model of IMD operations representing proper operation of an IMD comprises preprocessing the code path data prior to training the AI model.

Clause 107: The method of clause 106, wherein the preprocessing comprises generating code path metrics based on the code path data, wherein the code path metrics are utilized to train the AI model.

Clause 108: The method of clause 105, further comprising: preprocessing additional code path data prior to training the AI model.

Clause 109: The method of clause 105, wherein the set of IMDs is: different from the plurality of IMDs; the same as the plurality of IMDs; or includes at least one IMD included in the plurality of IMDs and at least one IMD not included in the plurality of IMDs.

Clause 110: The method of clause 105, wherein one or more baseline or expected code paths are learned by the AI model during the training, the one or more baseline or expected code paths corresponding to proper operation of the IMD.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or non-volatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import (e.g., "A and/or B") are recited or described, such a phrase should be understood to mean "only A, only B, or both A and B." Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. An implantable medical device (IMD) for implantation in a patient, comprising:
   one or more processors for controlling IMD operations;
   a battery for powering the IMD operations;
   circuitry for controlling provision of a medical therapy to the patient or for conducting medical diagnostic operations;

wireless communication circuitry for conducting communication with one or more devices external to the patient after implantation; and persistent memory for storing firmware for execution by the one or more processors, wherein the firmware includes a plurality of firmware modules controlling one or more corresponding hardware components of the IMD for respective IMD functions and wherein multiple identified code paths traversing respective firmware code instructions are identified for each of the plurality of firmware modules;

wherein the one or more processors, when executing firmware code for the IMD subsystems, are configured to:

store an identifier corresponding to a respective code path of the multiple identified code paths in one or more memory buffers to indicate execution of code of the respective code path;

calculate a deviation metric representing a difference between an observed firmware execution for a respective firmware module and baseline code execution defined for the respective firmware module; and responsive to determining that the deviation metric is greater than or equal to a threshold value, generate an error state notification with respect to the respective firmware module.

2. The IMD of claim 1, wherein the one or more processors are configured to generate a graduated response based on the deviation metric.

3. The IMD of claim 2, wherein the graduated response is selected from a plurality of pre-determined responses stored in the persistent memory of the IMD.

4. The IMD of claim 2, wherein the graduated response is generated based at least in part on a mode of the IMD, a type of functionality provided by the respective firmware module, or a combination thereof.

5. The IMD of claim 1, wherein the deviation metric is calculated using a trained artificial intelligence model.

6. The IMD of claim 1, wherein the deviation metric is calculated based on the stored identifiers.

7. The IMD of claim 1, wherein the deviation metric is calculated periodically according to a determined frequency.

8. The IMD of claim 7, wherein the frequency varies according to a function provided by the respective firmware module.

9. The IMD of claim 1, wherein the deviation metric is calculated prior to code path completion.

10. The IMD of claim 1, wherein the one or more processors are configured to provide the deviation metric to an external device as feedback.

11. The IMD of claim 10, wherein the external device comprises an analytics platform configured to train one or more artificial intelligence (AI) models using a training dataset, and wherein the training dataset is updated based on the feedback.

12. A system for managing an implantable medical device (IMD), the system comprising:

a memory; and one or more processors communicatively coupled to the memory and configured to:

receive an identifier corresponding to a respective code path of multiple identified code paths, each of the identified code paths corresponding to execution of one or more firmware modules a plurality of firmware modules of the IMD configured to control respective IMD functions for providing a therapy to a patient;

calculate a deviation metric representing a difference between an observed firmware execution for a respective firmware module and baseline code execution defined for a firmware module of the one or more firmware modules corresponding to the respective code path; and responsive to determining that the deviation metric is greater than or equal to a threshold value, generate an error state notification with respect to the respective firmware module.

13. The system of claim 12, wherein the one or more processors are configured to generate a graduated response based on the deviation metric, wherein the graduated response is configured to modify operations of the IMD.

14. The system of claim 13, wherein the graduated response is selected from a plurality of pre-determined responses stored in the persistent memory of the IMD.

15. The system of claim 13, wherein the graduated response is generated based at least in part on a mode of the IMD, a type of functionality provided by the respective firmware module, or a combination thereof.

16. The system of claim 12, wherein the deviation metric is calculated using a trained artificial intelligence (AI) model.

17. The system of claim 16, wherein the one or more processors are configured to update a training dataset used to train the AI model based on at least the received identifier.

18. The system of claim 12, wherein the identifier is received from a device external to the IMD.

19. The system of claim 12, wherein the deviation metric is calculated periodically according to a determined frequency.

20. The system of claim 19, wherein the frequency varies according to a function provided by the respective firmware module.

21. The system of claim 12, wherein the deviation metric is calculated prior to code path completion.

22. The system of claim 12, wherein the therapy provided to the patient is modified based at least in part on the deviation metric.

23. A method for monitoring an implantable pulse generator (IPG) for delivering a medical therapy to a patient, the method comprising:

storing, by one or more processors, firmware for execution by the one or more processors, wherein the firmware includes a plurality of firmware modules controlling one or more corresponding hardware components of the IPG for respective IPG functions and wherein multiple identified code paths traversing respective firmware code instructions are identified for each of the plurality of firmware modules;

storing, by the one or more processors when executing firmware code for the IPG subsystems, an identifier corresponding to a respective code path of multiple identified code paths in one or more memory buffers to indicate execution of code of the respective code path;

calculating, by the one or more processors, a deviation metric representing a difference between an observed firmware execution for a respective firmware module and baseline code execution defined for the respective firmware module; and responsive to determining that the deviation metric is greater than or equal to a threshold value, generating, by the one or more processors, an error state notification with respect to the respective firmware module.

24. The method of claim 23, wherein the one or more processors are configured to generate a graduated response based on the deviation metric, wherein the graduated response is selected from a plurality of pre-determined responses stored in the persistent memory of the IMD.

25. The method of claim 23, wherein the deviation metric is calculated using a trained artificial intelligence model.

26. The method of claim 23, wherein the one or more processors are configured to provide the deviation metric to an external device as feedback.

27. The method of claim 26, wherein the external device comprises an analytics platform configured to train one or more artificial intelligence (AI) models using a training dataset, and wherein the training dataset is updated based on the feedback.

* * * * *